(12) United States Patent
Caroff et al.

(10) Patent No.: US 7,727,979 B2
(45) Date of Patent: Jun. 1, 2010

(54) GUANIDINE DERIVATIVES AND THEIR USE AS NEUROPEPTIDE FF RECEPTOR ANTAGONISTS

(75) Inventors: Eva Caroff, Ranspach-le-Haut (FR);
Matthias Steger, St. Gallen (CH);
Oliver Valdenaire, Allschwil (CH);
Anja Fecher, Allschwil (CH); Volker Breu, Schliengen (DE); Kurt Hilpert, Hofstetten (CH); Heinz Fretz, Riehen (CH); Thomas Giller, Wintersingen (CH)

(73) Assignee: Actelion Pharmaceuticals Ltd., Allschwil (CH)

( * ) Notice: Subject to any disclaimer, the term of this patent is extended or adjusted under 35 U.S.C. 154(b) by 854 days.

(21) Appl. No.: 10/549,685

(22) PCT Filed: Mar. 22, 2004

(86) PCT No.: PCT/CH2004/000175

§ 371 (c)(1),
(2), (4) Date: Sep. 19, 2005

(87) PCT Pub. No.: WO2004/083218

PCT Pub. Date: Sep. 30, 2004

(65) Prior Publication Data

US 2006/0194788 A1 Aug. 31, 2006

(30) Foreign Application Priority Data

Mar. 20, 2003 (CH) .................................. 466/03

(51) Int. Cl.
| | |
|---|---|
| *A01N 43/00* | (2006.01) |
| *A01N 43/46* | (2006.01) |
| *A61K 31/55* | (2006.01) |
| *A01N 43/42* | (2006.01) |
| *A61K 31/44* | (2006.01) |
| *A01N 43/78* | (2006.01) |
| *A61K 31/425* | (2006.01) |
| *A01N 37/52* | (2006.01) |
| *A61K 31/155* | (2006.01) |
| *C07D 277/60* | (2006.01) |
| *C07D 277/62* | (2006.01) |
| *C07D 277/82* | (2006.01) |

(52) U.S. Cl. ...................... 514/215; 514/634; 514/301; 514/366; 548/152; 548/161

(58) Field of Classification Search ................ 514/772, 514/215, 301, 366, 634; 548/152, 161
See application file for complete search history.

(56) References Cited

U.S. PATENT DOCUMENTS 4,624,956 A * 11/1986 Lazzarini et al. ............ 514/301
4,716,228 A    12/1987 Scarponi et al.

FOREIGN PATENT DOCUMENTS

| | | |
|---|---|---|
| DE | 2206385 C2 | 8/1973 |
| EP | 0 321 191 | 6/1989 |
| GB | 1140387 | 1/1969 |
| JP | 09-059258 * | 4/1997 |
| WO | WO 02/24192 A1 | 3/2002 |
| WO | WO 2004/083218 A1 | 9/2004 |

OTHER PUBLICATIONS

Marinko P, Kastelic J, Krbavcic A and Kikelj. A convenient sysnthesis of 4-aminomethyl-4,5,67-tetrahydro-1,3-benzothiazole arginine side-chain memetics. Tetrahedron Letters 42 (2001) 8911-8913.*
Minault M, Lecron JC, Labrouche S, Simonnet G, and Gombert. characterization of binding sites for neuropeptide FF on T lymphocytes of the jurkat cell line. Peptide 16 (1995) 105-111.*
West, Anthony R., Solid State Chemistry and its Applications, Wiley, New York, 1988, pp. 358 & 365.*

(Continued)

*Primary Examiner*—Sreeni Padmanabhan
*Assistant Examiner*—Sarah Pihonak
(74) *Attorney, Agent, or Firm*—Hunton & Williams LLP

(57) ABSTRACT

The invention relates to guanidine derivatives of formula (I) where: A represents a chain of 3-6 carbon atoms, one of which can be replaced by —N(R')— or —O— and R' is H or a substituent; the ring skeleton only contains both double bonds of the thiazole component; the pharmaceutically-acceptable acid addition salts of basic compounds of formula (I), the pharmaceutically-acceptable salts of compounds of formula (I), comprising acid groups, with bases, the pharmaceutically-acceptable esters of hydroxy or carboxyl group containing compounds of formula (I) and the solvates or hydrates thereof, which exhibit a neuropeptide FF receptor antagonist effect. The above are suitable for the treatment of pain and hyperalgesia, withdrawal symptoms in alcohol, psychotropic and nicotine dependencies, for improvement or cure of said dependencies, for regulation of insulin excretion, food intake, memory functions, blood pressure, electrolyte and energy management and for treatment of urinary incontinence. The above can be produced using generally used methods and processed to give medicaments.

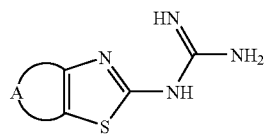

18 Claims, No Drawings

OTHER PUBLICATIONS

Marinko et al 'Tetrahedron letters' 42 (2001) 8911-8913.*
Yoshiro Usi, Annual Reports Takeda Research Laboratory, 1968, Research & Development Division Chemical Industries Ltd., vol. 27, Abstract.*
Yang, et al., "Isolation, Sequencing, Synthesis, and Pharmacological Characterization of Two Brain Neuropeptides that Modulate the Action of Morphine", PNAS, vol. 82, pp. 7757-7761, 1985.
Roumy, et al., "Neuropeptide FF, Pain and Analgesia", European Journal of Pharmacology, vol. 345, pp. 1-11, 1998.
Panula, et al., "Neuropeptide FF, A Mammalian Neuropeptide with Multiple Functions", Progress in Neurobiology, vol. 48, pp. 461-487, 1996.
Lake, et al., "IgG from Neuropeptide FF Antiserum Reverses Morphine Tolerance in the Rat", Neuroscience Letters, vol. 132, pp. 29-32, 1991.
Elshourbagy, et al., "Receptor for the Pain Modulatory Neuropeptides FF and AF is an Orpahn G Protein-coupled Receptor", The Journal of Biological Chemistry, vol. 275, No. 34, pp. 25965-25971, 2000.
Sundblom, et al., "Pulsatile Secretion of Neuropeptide FF into Human Blood", Peptides, vol. 19, No. 7, pp. 1165-1170, 1998.
Bonini, et al., "Identification and Characterization of Two G Protein-coupled Receptors for Neuropeptide FF", The Journal of Biological Chemistry, vol. 275, No. 50, pp. 39324-39331, 2000.
Kotani, et al., "Functional Characterization of a Human Receptor for Neuropeptide FF and Related Peptides", British Journal of Pharmacology, vol. 133, pp. 138-144, 2001.
Allard, et al., "Characterization of Rat Spinal Cord Receptors to FLFQPQRFamide, a Mammalian Morphine Modulating Peptide: A Binding Study", Brain Research, vol. 500, pp. 169-176, 1989.
Allard, et al., "Autoradiographic Distribution of Receptors to FLFQPQRFamide, a Morphine-Modulating Peptide, in Rat Central Nervous System", Neuroscience, vol. 49, No. 1, pp. 101-116, 1992.
Gouarderes, et al., "Quantitative Autoradiographic Distribution of $NPFF_1$ Neuropeptide FF Receptor in the Rat Brain and Comparison with $NPFF_2$ Receptor by Using $[^{125}I]YVP$ and $[^{125}I]EYF$ as Selective Radioligands", Neuroscience, vol. 115, No. 2, pp. 349-361, 2002.
Liu, et al., "Identification and Characterization of Novel Mammalian Neuropeptide FF-like Peptides that Attenuate Morphine-Induced Antinociception", The Journal of Biological Chemistry, vol. 276, No. 40, pp. 36961-36969, 2001.
Lefrere, et al., "Neuropeptide AF and FF Modulation of Adipocyte Metabolism", The Journal of Biological Chemistry, vol. 277, No. 42, pp. 39169-39178, 2002.
Malin, et al., "Analog of Neuropeptide FF Attenuates Morphine Abstinence Syndrome", Peptides, vol. 12, pp. 1011-1014, 1991.
Prokai, et al., "Combinatorial Lead Optimization of a Neuropeptide FF Antagonist", J. Med. Chem., vol. 44, pp. 1623-1626, 2001.
Mollereau, et al., "Pharmacological Characterization of Human $NPFF_1$ and $NPFF_2$ Receptors Expressed in CHO Cells by Using NPY $Y_1$ Receptor Antagonists", European Journal of Pharmacology, vol. 451, pp. 245-256, 2002.
Quelven, et al., "Dissociation of Pharmacological Pro- and Anti-opioid Effects by Neuropeptide FF Analogs", European Journal of Pharmacology, vol. 449, pp. 91-98, 2002.
Schnur, et al., "N-(5-Fluorobenzothiazol-2yl)-2-guanidinothiazole-4-carboxamide. A Novel, Systemically Active Antitumor Agent Effective Against 3LL Lewis Lung Carcinoma", J. Med. Chem., vol. 34, pp. 914-918, 1991.
Tanaka, et al., "Antiplatelet Agents Based on Cyclooxygenase Inhibition without Ulcerogenesis. Evaluation and Synthesis of 4,5-Bis(4-methoxyphenyl)-2-substituted-thiazoles", J. Med. Chem., vol. 37, pp. 1189-1199, 1994.
Yokoo, et al., "Synthesis of 1-Azacycloheptan-4-one Hydrochloride", Studies on Seven-membered Heterocyclic Compounds Containing Nitrogen. I., vol. 29, No. 5, pp. 631-632, 1956.
Bertz, et al., "Organocopper Reagents in Dimethyl Sulfide", Tetrahedron, vol. 45, No. 2, pp. 425-434, 1989.
Brummond, et al., "α-Chlorination of Ketones Using p-Toluenesulfonyl Chloride", Tetrahedron Letters, vol. 40, pp. 2231-2234, 1999.
Mihovilovic, et al., "Asymmetric Baeyer-Villiger Oxidations of 4-Mono- and 4,4-Disubstituted Cyclohexanones by Whole Cells of Engineered *Escherichia coli*", J. Org. Chem. vol. 66, pp. 733-738, 2001.
Baigrie, et al., "Stereospecific Formation of Enolates from Reaction of Unsymmetrical Ketenes and Organolithium Reagents", J. Am. Chem. Soc., vol. 107, No. 19, pp. 5391-5396, 1985.
De Jongh, et al., "Synthesis of Polyspiro Compounds Consisting of Cyclohexane Rings", Tetrahedron, vol. 20, pp. 2553-2573, 1964.
Radivoy, et al., "Reduction of Sulfonates and Aromatic Compounds with the $NiCl_2*2H_2O$-Li-Arene (cat.) Combination", Tetrahedron, vol. 55, pp. 14479-14490, 1999.
Ritter, "Synthetic Transformations of Vinyl and Aryl Triflates", Synthesis, pp. 735-762, 1993.
Magnus, et al., "Application of the β-Azidonation Reaction to the Synthesis of the Antitumor Alkaloid (+)- Pancratistatin", Tetrahedron, vol. 54, pp. 15509-15524, 1998.
Reetz, et al., "The Kharasch Reaction Revisited: $CuX_3Li_2$-catalyzed Conjugate Addition Reactions of Grinard Reagents", Journal of Organometallic Chemistry, vol. 502, pp. C5-C7, 1995.
Parker, et al., "Enantioselective Synthesis of the Enyne A-Ring Synthon of the lα-Hydroxy Vitamins D", J. Org. Chem., vol. 62, No. 19, pp. 6692-6696, 1997.
Cazaeu, et al., "A New Practical Synthesis of Silyl Enol Ethers. Part. I. From Simple Aldehydes and Ketones", Tetrahedron, vol. 43, No. 9, pp. 2075-2088, 1987.
Reetz, et al., "tert-Alkylation of Ketones and Aldehydes", Angew. Chem. Int: Ed. Engl. vol. 17, No. 1, pp. 48-49, 1978.
Sit, et al., "Novel Dihydropyrazine Analogues as NPY Antagonists", Bioorganic & Medicinal Chemistry Letters, vol. 12, pp. 337-340, 2002.
Vilim, et al., "Gene for Pain Modulatory Neuropeptide NPFF: Induction in Spinal Cord by Noxious Stimuli", Molecular Pharmacology, vol. 55, p. 804-811, pp. 1999.
Perry, et al., "A Human Gene Encoding Morphine Modulating Peptides Related to NPFF and FMRFamide", FEBS Letters, vol. 409, pp. 426-430, 1997.
Kontinen, et al., "Differential Modulation of $α_2$-Adrenergic and μ-Opioid Spinal Antinociception by Neuropeptide FF", Peptides, vol. 16, No. 5, pp. 973-977, 1995.
Gouarderes, et al., "Antinociceptive Effects of Intrathecally Administered F8Famide and FMRFamide in the Rat", European Journal of Pharmacology, vol. 237, pp. 73-81, 1993.
Singh, et al., "Synthesis & Mass Spectra of Some Substituted 2-(2'-Benzazolylamino) Pyrimidines", Indian Journal of Chemistry, vol. 228, pp. 37-42, Jan. 1983.
Peterlin-Masic, et al., "A General Synthetic Approach to Novel Conformationally Restricted Arginine Side Chain Mimetics", Tetrahedron, vol. 58, pp. 1557-1563, 2002.
Scarponi, et al., "Byciclic Compounds with Potential Antiulcer and/or Antisecretory Activity", Il Farmaco, vol. 43, No. 7-8, pp. 575-596, 1988.
Marinko, et al., "A Convenient Synthesis of 4-aminomethyl-4, 5, 6, 7-tetrahydro-1, 3-benzothiazole Arginine Side-Chain Mimetics", Tetrahedron Letters, vol. 42, No. 50, pp. 8911-8913, 2001.
Database Caplus 'Online! Chemical Abstracts Service, Columbus, Ohio, retrieved from STN Database Accession No. 1986:168468 XP002249435, RN 92715-48-5, 101242-99-3, 101243-00-9, 101243-32-7 and 101701-49-9 & JP 60 226810 A, Ikeda Mohando Co., Ltd., Nov. 12, 1985.
Database Caplus 'Online! Chemical Abstracts Service, Columbus, Ohio, retrieved from STN Database Accession No. 1987:176383 XP002249436, RN 107880-36-4 and 10788-37-5 & JP 62 033158 A, Shionogi and Co., Ltd.,. Feb. 13, 1987.
Database Caplus 'Online! Chemical Abstracts Service, Columbus, Ohio, retrieved from STN Database Accession No. 1986:168468 XP002249437, RN 188611-98-5 & JP 90 059258 A, Ono Pharmaceutical Co., Mar. 4, 1997.

* cited by examiner

GUANIDINE DERIVATIVES AND THEIR USE AS NEUROPEPTIDE FF RECEPTOR ANTAGONISTS

CROSS-REFERENCE TO RELATED APPLICATIONS

This application is a U.S. national phase application of PCT International Application No. PCT/CH2004/000175, filed on Mar. 22, 2004, which claims the benefit of Swiss Application No. 0466/03, filed Mar. 20, 2003, the disclosures of each of which are herein incorporated by reference in their entireties.

BACKGROUND OF THE INVENTION (i) Field of the Invention

The present invention relates to guanidine derivatives of the general formula

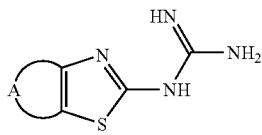

I in which A represents a chain of 3-6 optionally substituted C atoms, one of which can be replaced by —N(R')— or —O—; and R' represents hydrogen or a substituent; the ring skeleton containing only the two double bonds of the thiazole component; pharmaceutically applicable acid addition salts of basic compounds of formula I, pharmaceutically applicable salts of acid group-containing compounds of formula I with bases, pharmaceutically applicable esters of hydroxy or carboxy group-containing compounds of formula I as well as hydrates or solvates thereof.

Guanidine derivatives of formula I which contain one or more asymmetric center can be present as optically pure enantiomers, as mixtures of enantiomers, such as for example racemates, or optionally as optically pure diastereomers, as mixtures of diastereomers, as diastereomeric racemates or as mixtures of diastereomeric racemates.

The products defined at the outset are partly known and partly novel, and they are characterized by valuable pharmacodynamic properties, acting as neuropeptide FF receptor antagonists.

In a first aspect the present invention relates to the use of the compounds described at the outset of Formula I as well as the salts, esters, hydrates and solvates likewise defined at the outset as neuropeptide FF receptor antagonists or for the preparation of corresponding medicinal products, in particular for the treatment of pain and hyperalgesia, withdrawal syndromes in the case of alcohol, psychotropic and nicotine dependences and for the improvement or elimination of these dependences, for the regulation of insulin secretion, food intake, memory functions, blood pressure, and of the electrolyte and energy balance and for the treatment of urinary incontinence or for the preparation of corresponding medicinal products.

The pains to be treated according to the invention can be chronic, acute, long-lasting or temporary, these pains being able to be of operative, traumatic, or pathological origin; an advantage achieved according to the invention consists in the prevention of opioid tolerance and/or opioid dependence.

(ii) Description of the Related Art

Back in 1985 neuropeptide FF (NPFF; H-Phe-Leu-Phe-Gln-Pro-Gln-Arg-Phe-NH$_2$ [99566-27-5]), an octapeptide, and neuropeptide AF (NPAF; H-Ala-Gly-Glu-Gly-Leu-Ser-Ser-Pro-Phe-Trp-Ser-Leu-Ala-Ala-Pro-Gln-Arg-Phe-NH$_2$ [99588-52-0]), a related octadecapeptide, were discovered as neurotransmitters of the central nervous system in cattle brains (Yang et al., Proc. Natl. Acad. Sci. USA 1985, 82(22), 7757-61) and originally characterized as anti-opioid peptides. The carboxy-terminal amidated neuropeptides were, because of their reactivity with anti-Phe-Met-Arg-Phe-NH$_2$ antiserum, included among the FMRF-amide-like peptides. Both peptides have pain-modulating properties, the octapeptide having greater effectiveness. Both peptides play an important role both in opioid-dependent analgesia and in the development of tolerance to opioids (review article: Roumy and Zajac, Europ. J. Pharm. 1998, 345, 1-11; Panula et al., Prog. Neurobiol. 1996, 48, 461-87). Interestingly, in animal tests, NPFF shows, depending on the nature of the administration, both anti-opioid and pro-opioid actions. Thus NPFF can reverse the acute effects of opioids and an increased concentration in the brain is possibly responsible for the development of opioid tolerance and dependence. In rats, for example, the intracerebroventricular (i.c.v.) administration of NPFF lowers the nociceptive threshold and reduces the analgesia induced by morphine. Administration of NPFF to morphine-tolerant rats causes symptoms of withdrawal phenomena. The analgesic effect of morphine in morphine-tolerant rats was reproduced after i.c.v. injection of anti-NPFF IgG (Lake et al., Neurosci. Lett. 1991, 132, 29-32). Immunoneutralization of NPFF by intrathecally (i.t.) administered anti-NPFF antibodies increase the analgesia caused by endogenous and exogenous opioids. By direct injection of NPFF or NPFF-analogues into the spinal cord (i.t.) a pro-opioid effect with a long-lasting opioid-like analgesia and an increased pain-relieving effect of morphine was obtained (Gouardères et al., Eur. J. Pharmacol. 1993, 237, 73-81; Kontinen and Kaso, Peptides 1995, 16, 973-977).

According to other reports NPFF also appears to play a role in physiological processes such as insulin secretion, regulation of food intake, memory functions, regulation of blood pressure and electrolyte balance (Panula et. al., Prog. Neurobiol. 1996, 48, 461-487).

In various types of mammal, such as humans, rats, mice and cattle, the discovery was reported of a gene, which codes NPFF and NPAF as a common precursor protein, from which the two active peptides are finally split off (Perry et al., FEBS Lett. 1997, 409, 426-30; Vilim et al., Mol. Pharmacol. 1999, 55, 804-11). In humans the gene for this precursor is expressed both peripherally in various organs and in regions of the central nervous system, in particular in the cerebellum (Elshourbagy et al., J. Biol. Chem. 2000, 275 (34), 25965-71), while the expression in rats is restricted exclusively to specific regions of the central nervous system such as the hypothalamus, medulla, and dorsal horn of the spinal cord. On the basis of the demonstration of NPFF in human blood plasma it is presumed, that the peptides are peripherally also responsible for hormone-like effects (Sandblom et al., Peptides 1998, 19, 1165-70).

In tissue samples from humans and rats two G-protein coupled receptors (GPCR), NPFF1 and NPFF2 were identified (Bonini et al., J. Biol. Chem. 2000, 275 (50), 39324-31; Kotani et al., Br. J. Pharmacol. 2001, 133, 138-44), NPFF2 being identical to the receptor HLWAR77 originally described as an orphan (Elshourbagy et al., J. Biol. Chem. 2000, 275 (34), 25965-71). NPFF1 and NPFF2 were able to be characterized as specific receptors with affinities in the nanomolar and subnanomolar regions for the two neuropeptides FF and AF. NPFF binds to NPFF1 with a binding constant Kd=1.13 nM and to NPFF2 with Kd=0.37 nM. The identity of NPFF1 and NPFF2 is around 50%. The comparison of the amino acid sequences with known GPCRs shows a 30-40% similarity with human orexin-1, orexin-2, neuropeptide Y(NPY) Y2, cholecystokinin A, NPY Y1, prolactin-releasing hormone receptor and NPY Y4. The distribution of NPFF1 and NPFF2 in various tissue samples from humans and rats was determined by demonstrating the m-RNA using RT-PCR (reverse transcription-polymerase chain reaction). NPFF1 was demonstrated predominantly in the central nervous system (CNS). By contrast, NPFF2 was found predominantly in the spinal cord. These findings are supported by autoradiographic methods using selective NPFF1 and NPFF2 radioligands (Allard et al., Brain Res. 1989, 500, 169-176; Neuroscience 1992, 49, 106-116; Gouardères et al., Neuroscience 2002 115:2 349-61).

The neuropeptides SF (NPSF, 37 amino acids) and neuropeptide VF (NPVF, octapeptide) described as NPFF-related peptides, both located on the so-called NPVF-gene, bind with comparatively greater affinity and selectivity to the NPFF1 receptor than NPFF and NPAV. The NPVF peptides also block the morphine-induced analgesia in acute and inflammatory pain models more markedly than NPFF and emphasize the importance of the NPVF/FF1 system as part of an endogenous anti-opioid mechanism (Q. Liu et al., J. Biol. Chem. 2002, 276 (40), 36961).

The incidence of functional NPFF1 and NPFF2 receptors in adipocytes and the effect of NPFF and NPAF on key sites of signal transmission in the adipose metabolism suggest that the two peptides, alongside their original pain-modulating effects, could also have an influence on the storage and use of body energy (I. Lefrère et al., J. Biol. Chem. 2002, 277 (42), 39169).

The desamino-Tyr-Phe-Leu-Phe-Gln-Pro-Gln-Arg-NH$_2$ peptide was described as the first NPFF-receptor antagonist counteracting the NPFF effects. After i.c.v. injection this peptide reduced the withdrawal syndromes in the case of morphine dependence (Malin et al., Peptides 1991, 12, 1011-1014). However, this peptide showed no bioavailability whatever in the central nervous system. Optimization of the tripeptide Pro-Gln-Arg-NH$_2$ in a combinative approach led to dansyl-Pro-Gln-Arg-NH$_2$, or dansyl-Pro-Ser-Arg-NH$_2$, both with improved properties for passing through the blood-brain barrier, which, after systemic administration in rats led to an improved antagonistic effect of the anti-opioid symptoms caused by NPFF (Prokai et al. J. Med. Chem. 2001, 44, 1623-1626). The Arg-Tyr-amide peptoid BIBP3226 originally described as an NPY Y1 selective receptor antagonist showed a 10-60 times higher affinity to the human and rat-NPFF1 receptor than to the corresponding NPFF2 receptors (Bonini et al., J. Biol. Chem. 2000, 275 (50), 39324-31). From a series of compounds which originate from the NPY Y1 selective antagonist BIP3226, selective hNPFF1 receptor antagonists were obtained which showed affinities of 40-80 nM (Mollereau et al., Europ. J. Pharmacol. 2002, 45, 245-56).

The two neuropeptide FF analogues 1DME ([D-Tyr$^1$, (Nme)Phe$^3$]NPFF) and Nic-1DME (nicotinoyl-pro-1Dme) showed different pharmacological properties in the mouse tail-flick test, although both compounds bind to NPFF1 and NPFF2 with comparable affinity and selectivity. Both 1DME and Nic-1DME reinforce the morphine analgesia after i.t. and i.p. administration, but Nic-1DME cannot suppress morphine-induced analgesia after i.c.v. and i.p. administration (Quelven et al., Europ. J. Pharmacol. 2002, 449, 91-98).

In WO 02/24192 A1 synthetic NPFF ligands with a peptide structure, based on arginine as the central component, are described.

SUMMARY AND OBJECTS OF THE INVENTION

The products defined at the outset are potent and specific, low-molecular antagonists of neuropeptide FF1 receptors with non-peptide or non-peptoid structures.

The current options for treatment of chronic pain are based on NSAIDs (non-steroidal anti-inflammatory drugs), canabinoids and opioids. Thus, for example, morphine derivatives bind to the μ-opioid receptor and thereby have an analgesic effect. Opioid binding to the μ-opioid receptor involves the release of neuropeptide FF. Based on the animal experiments mentioned above it is presumed that the released NPFF reduces the analgesic effect of the administered opioids and leads to tolerance to opioids. In order to obtain a constant analgesic effect with longer treatments, increasingly higher opioid doses must be administered as a result of this tolerance, which can finally lead to serious side effects. As already mentioned at the outset, as of today two neuropeptide FF receptors are known, the NPFF1 receptor being located mainly in the central nervous system and the NPFF2 receptor in the spinal cord in particular. Activation of the NPFF2 receptors shows an opioid-like analgesic effect. Blocking of the NPPF1 receptors by an antagonist prevents the development of tolerance to opioids and also increases their effect.

As mentioned at the outset, the products defined there are partly known and partly novel, and they are characterized by the valuable pharmacological property of blocking the interaction of neuropeptide FF with the neuropeptide FF1 receptor subtype.

If one or more of the C atoms in the chain A in formula I is/are substituted, then
  one of the C atoms can carry one or two (i.e. geminal) identical or different substituents; or
  several of the C atoms can each carry one or two (i.e. geminal) identical or different substituents.

In Formula I, A together with the thiazole ring can form a cyclopentathiazole, benzothiazole, cycloheptathiazole, pyranothiazole, thiazolopyridine, thiazoloazepine or thiazolooxepane skeleton which contains only the two double bonds of the thiazole component, such as for example a 4,5,6,7-tetrahydrobenzothiazole, 5,6,7,8-tetrahydro-4H-cycloheptathiazole, 5,6-dihydro-4H-cyclopentathiazole, 6,7-dihydro-4H-pyrano[4,3-d]thiazole, or 5,6,7,8-tetrahydro-4H-thiazolo[4,5-c]azepine skeleton.

A subgroup of the compounds of Formula I can be represented by the general formula

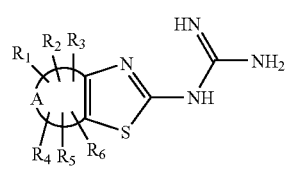

II in which R$_1$-R$_6$ mean hydrogen, alkyl, alkanoyl, alkenyl, alkoxy, alkoxyalkyl, alkoxyalkanoyl, alkoxyalkylcarbamoyl, alkoxyalkylthiocarbamoyl, alkoxycarbonyl, alkoxycarbonylalkyl, alkoxycarbonylalkanoyl, alkylamido, alkylaminocarbonyl, alkylarylamino, alkylcarbamoyl, alkylthiocarbamoyl, alkylcarbonyl, alkylcarbonyloxy, alkylenedioxy, alkylsulphinyl, alkylsulphinylalkyl, alkylsulphonyl, alkylsulphonylalkyl, alkylthio, alkylsulphonamido, alkylthioalkyl, alkynyl, amino, aminoalkyl, aminoalkanoyl, aminoacyl, alkylamino, alkylaminoalkyl, alkylaminoalkanoyl, aminocarbonyl, aminocarbonylalkyl, aminocarbonylalkanoyl, alkylaminocarbonylamino, alkoxycarbonylamino, aryl, arylalkenyl, arylalkyloxy, arylalkyl, arylalkylamido, arylalkanoyl, arylamido, arylamino, aryl-aminocarbonyl, arylcarbamoyl, arylthiocarbamoyl, aryloxy, aryloxyalkyl, aryloxyalkanoyl, aryloxyalkylamino, aryloxyalkylcarbamoyl, aryloxyalkylthiocarbamoyl, aryloxycarbonyl, aryloxycarbonylalkyl, aryloxycarbonylalkanoyl, aryloxycarbonylalkylamino, aryloxycarbonylalkylcarbamoyl, aryloxycarbonylalkylthiocarbamoyl, arylsulphinyl, arylsulphinylalkyl, arylsulphonyl, arylsulphonylalkyl, arylsulphonylalkanoyl, arylsulphonamido, arylthio, arylthioalkyl, arylthioalkanoyl, carboxy, carboxyl, carboxyalkyl, carboxyalkylamido, cyano, cyanoalkyl, cyanoalkylamido, cyanoalkanoyl, cycloalkyl, cycloalkylamido, cycloalkanoyl, cycloalkylamino, cycloalkylaminocarbonyl, cycloalkyloxycarbonyl, cycloalkyloxycarbonylalkyl, cycloalkyloxy-carbonylalkylamido, cycloalkyloxycarbonylalkanoyl, dialkylaminocarbonyl, dialkylaminoalkyl, dialkylaminoalkylamido, dialkylaminoalkanoyl, diarylamino, formyl, formylalkyl, halogen, haloalkoxy, haloalkyl, haloalkylamido, haloalkanoyl, halo-alkylamino, heteroarylamino, heteroarylamido, heterocyclylalkylamido, heteroarylaminocarbonyl, heteroaryloxycarbonylalkyl, heteroaryloxycarbonylalkylamido, heteroaryloxycarbonylalkanoyl, heterocyclyl, heterocyclylamino, heterocyclylamido, heterocyclylalkyl, heterocyclylalkanoyl, heterocyclylalkylamino, heterocyclylalkylamido, heteroarylalkyl, heteroarylalkanoyl, heteroarylalkylamino, heteroarylalkylamido, heteroyclylalkylaminocarbonyl, heterocyclylalkoxycarbonylalkyl, heterocyclylalkoxy-carbonylalkanoyl, heterocyclylalkoxycarbonylalkylamino, heterocyclylalkoxycarbonylalkylamido, hydroxy, hydroxyalkyl, hydroxyalkanoyl, mercapto or nitro.

Preferred possible meanings for $R_1$ are methyl, ethyl, n-propyl, isopropyl, n-butyl, isobutyl, tert-butyl, 1,1-dimethylpropyl, or phenyl. If $R_2$-$R_6$ are different from hydrogen, then they preferably mean methyl or another low alkyl radical. Another subgroup of the compounds of Formula I can be represented by the general Formula

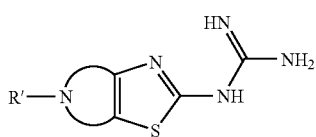

III in which R' means alkyl, alkanoyl, alkenyl, alkinyl, alkoxycarbonylalkyl, alkoxycarbonylaminoalkanoyl, alkylcarbamoyl, alkoxycarbonylalkylcarbamoyl, alkoxycarbonylalkylthiocarbamoyl, alkylthiocarbamoyl, mono- or disubstituted aminoalkanoyl, aryl, arylalkyl, arylalkoxycarbonyl, arylalkanoyl, arylcarbamoyl, alkoxyalkanoyl, alkylsulphonyl, arylthiocarbamoyl, aryloxycarbonylalkyl, aryloxycarbonylalkanoyl, aryloxycarbonylalkylcarbamoyl, aryloxycarbonylalkylthio-carbamoyl, arylsulphonyl, cycloalkyl, cycloalkanoyl, cycloalkylcarbamoyl, cycloalkylthiocarbamoyl, cycloalkylcarbonyl, cycloalkyloxycarbonylalkyl, cycloalkyloxycarbonylalkanoyl, cycloalkyloxycarbonylalkylcarbamoyl, cycloalkyloxycarbonylalkyl-thiocarbamoyl, heteroarylalkyl, heterocyclylalkyl, heterocyclylalkoxycarbonylalkyl, heterocyclylalkoxycarbonylalkanoyl, heterocyclylalkoxycarbonylalkylcarbamoyl, heterocyclylalkoxycarbonylalkylthiocarbamoyl, heteroaryloxycarbonylalkyl, heteroaryloxycarbonylalkylcarbamoyl or heteroaryloxycarbonylalkylthiocarbamoyl.

R' preferably means methyl, ethyl, propyl, hexyl, 2,2-dimethylpropionyl, cyclopropylmethyl, 2-cyclohexylethyl, propinyl, ethyloxycarbonylethyl, benzyl, n-butyloxycarbonyl, tert-butyloxycarbonyl, benzyloxy-carbonyl, 3-methylbutyryl, pentanoyl, phenylacetyl, 2-propyl-pentanoyl, cyclopropanecarbonyl, isobutyryl, but-3-enoyl, 2-methoxy-acetyl, propane-2-sulphonyl, butane-1-sulphonyl, methanesulphonyl, tert-butyloxycarbonyl-aminopropionyl or 4-dimethylamino-butyryl.

The use according to the invention of the following compounds of Formula III is preferred:
2-guanidino-6,7-dihydro-4H-thiazolo[5,4-c]pyridine-5-carboxylic acid tert-butyl ester;
N-(5-hexyl-4,5,6,7-tetrahydro-thiazolo[5,4-c]pyridine-2-yl)-guanidine;
N-[5-(2-cyclohexyl-ethyl)-4,5,6,7-tetrahydro-thiazolo[5,4-c]pyridine-2-yl]-guanidine;
N-(5-ethyl-4,5,6,7-tetrahydro-thiazolo[5,4-c]pyridine-2-yl)-guanidine;
2-guanidino-6,7-dihydro-4H-thiazolo[5,4-c]pyridine-5-carboxylic acid butyl ester;
N-[5-(propane-2-sulphonyl)-4,5,6,7-tetrahydro-thiazolo[5,4-c]pyridine-2-yl]-guanidine;
N-(5-phenylacetyl-4,5,6,7-tetrahydro-thiazolo[5,4-c]pyridine-2-yl)-guanidine;
2-guanidino-6,7-dihydro-4H-thiazolo[5,4-c]pyridine-5-carboxylic acid benzyl ester;
N-(5-pentanoyl-4,5,6,7-tetrahydro-thiazolo[5,4-c]pyridine-2-yl)-guanidine;
2-guanidino-6,7-dihydro-4H-thiazolo[5,4-c]pyridine-5-thiocarboxylic acid propyl amide;
N-[5-(2-propyl-pentanoyl)-4,5,6,7-tetrahydro-thiazolo[5,4-c]pyridine-2-yl]-guanidine;
N-(5-benzyl-4,5,6,7-tetrahydro-thiazolo[5,4-c]pyridine-2-yl)-guanidine;
N-(5-prop-2-ynyl-4,5,6,7-tetrahydro-thiazolo[5,4-c]pyridine-2-yl)-guanidine;
N-(5-cyclopropanecarbonyl-4,5,6,7-tetrahydro-thiazolo[5,4-c]pyridine-2-yl)-guanidine;
N-[5-(butane-1-sulphonyl)-4,5,6,7-tetrahydro-thiazolo[5,4-c]pyridine-2-yl]-guanidine;
N-(5-isobutyryl-4,5,6,7-tetrahydro-thiazolo[5,4-c]pyridine-2-yl)-guanidine;
N-[5-(2,2-dimethyl-propionyl)-4,5,6,7-tetrahydro-thiazolo[5,4-c]pyridine-2-yl]-guanidine;
2-guanidino-6,7-dihydro-4H-thiazolo[5,4-c]pyridine-5-thiocarboxylic acid benzyl amide;
2-guanidino-6,7-dihydro-4H-thiazolo[5,4-c]pyridine-5-carboxylic acid tert-butyl amide;
N-(5-but-3-enoyl-4,5,6,7-tetrahydro-thiazolo[5,4-c]pyridine-2-yl)-guanidine;
N-(5-benzyl-5,6,7,8-tetrahydro-4H-thiazolo[4,5-c]azepine-2-yl)-guanidine;
3-(2-guanidino-6,7-dihydro-4H-thiazolo[5,4-c]pyridine-5-yl)-propionic acid ethyl ester;
2-guanidino-6,7-dihydro-4H-thiazolo[5,4-c]pyridine-5-carboxylic acid pentyl amide;
N-[5-(2-methoxy-acetyl)-4,5,6,7-tetrahydro-thiazolo[5,4-c]pyridine-2-yl]-guanidine;
N-(5-cyclopropylmethyl-4,5,6,7-tetrahydro-thiazolo[5,4-c]pyridine-2-yl)-guanidine;

N-(5-methanesulphonyl-4,5,6,7-tetrahydro-thiazolo[5,4-c]pyridine-2-yl)-guanidine;
N-[5-(3-methyl-butyryl)-4,5,6,7-tetrahydro-thiazolo[5,4-c]pyridine-2-yl]-guanidine;
2-guanidino-6,7-dihydro-4H-thiazolo[5,4-c]pyridine-5-thiocarboxylic acid-(2-methoxy-1-methyl-ethyl)-amide;
2-guanidino-6,7-dihydro-4H-thiazolo[5,4-c]pyridine-5-carboxylic acid phenyl amide;
[3-(2-guanidino-6,7-dihydro-4H-thiazolo[5,4-c]pyridine-5-yl)-3-oxo-propyl]-carbamic acid tert-butyl ester;
N-[5-(4-dimethylamino-butyryl)-4,5,6,7-tetrahydro-thiazolo[5,4-c]pyridine-2-yl]-guanidine;
N-(5-propyl-4,5,6,7-tetrahydro-thiazolo[5,4-c]pyridine-2-yl)-guanidine; and
2-guanidino-6,7-dihydro-4H-thiazolo[5,4-c]pyridine-5-thiocarboxylic acid isopropyl amide.

Compounds of the Formula I defined at the outset in which A means a chain of 3-6 optionally substituted C atoms, one of which can be replaced by —O—, the ring skeleton containing only the two double bonds of the thiazole component;

pharmaceutically applicable acid addition salts of basic compounds, pharmaceutically applicable salts of acid group-containing compounds with bases, pharmaceutically applicable esters of hydroxy or carboxy group-containing compounds as well as hydrates or solvates thereof;

with the exception of
N-(4,5,6,7-tetrahydro-benzothiazole-2-yl)-guanidine;
(2-guanidino-4,5,6,7-tetrahydro-benzothiazole-4-yl)-ethyl acetate ethyl ester;
N-(4-hydroxymethyl-4,5,6,7-tetrahydro-benzothiazole-2-yl)-guanidine;
N-(4-tosyloxymethyl-4,5,6,7-tetrahydro-benzothiazole-2-yl)-guanidine;
N-(4-azidomethyl-4,5,6,7-tetrahydro-benzothiazole-2-yl)-guanidine;
N-(4-aminomethyl-4,5,6,7-tetrahydro-benzothiazole-2-yl)-guanidine; and
N-(6-acetylaminomethyl-4,5,6,7-tetrahydro-benzothiazole-2-yl)-guanidine;

are novel.

In a further aspect the present invention thus comprises these novel substances as such and as therapeutic active ingredients; methods for their preparation; medicinal products, containing one of the above novel substances; the preparation of such medicinal products; and the use of these novel substances as neuropeptide FF receptor antagonists or for the preparation of corresponding medicinal products according to the first aspect described above of the present invention.

In the novel compounds defined above of Formula I, in chain A
one of the C atoms can carry one or two (i.e. geminal), identical or different substituents; or
several of the C atoms can each carry one or two (i.e. geminal), identical or different substituents.
The substituent(s) can be selected from alkyl, alkenyl, cycloalkenyl, aryl, heteroaryl, aralkyl, alkoxycarbonyl, carboxamido, cyano or cyanolakyl groups and/or from polymethyl groups linked with one and the same C atom.
In particular the substituent(s) can be selected from
methyl, ethyl, n-propyl, isopropyl, n-butyl, isobutyl, sec-butyl, tert-butyl, 1,1-dimethylpropyl, allyl and cyclohex-1-enyl groups; and/or
phenyl, o-tolyl, m-tolyl, p-tolyl, 2-ethylphenyl, 3-fluorophenyl, 4-fluorophenyl, 4-chlorophenyl, 4-cyanophenyl, 4-benzyloxyphenyl, 3-methoxyphenyl, 4-methoxyphenyl, 3,4-dimethoxyphenyl, 3,4-methylenedioxyphenyl and bis-3,5-trifluoromethylphenyl groups; and/or
thiophene-2-yl and benzyl groups; and/or
ethoxycarbonyl groups; and/or
n-propylamino, benzylamino, N-methyl-N-phenethylamino, 3-methylbutylamino, phenylamino, N-butyl-N-ethylamino, di-n-propylamino, allylamino, piperidine-1 and morpholine-4-carbonyl groups; and/or
cyano and cyanoethyl groups; and/or
pentamethylene groups linked with one and the same C atom.

Novel compounds are preferred in which there is located on one and the same C atom on the one hand a phenyl group and on the other hand an ethoxycarbonyl, cyano or phenyl group.

Quite particularly preferred novel substances are:
N-(5-ethyl-5-methyl-4,5,6,7-tetrahydro-benzothiazole-2-yl)-guanidine and its formate;
N-(5,5-dimethyl-4,5,6,7-tetrahydro-benzothiazole-2-yl)-guanidine and its formate;
N-(5,5-dimethyl-6-phenyl-4,5,6,7-tetrahydro-benzothiazole-2-yl)-guanidine and its formate;
N-(4-tert-butyl-4,5,6,7-tetrahydro-benzothiazole-2-yl)-guanidine;
N-(6-isopropyl-4,5,6,7-tetrahydro-benzothiazole-2-yl)-guanidine;
N-(5,5,7-trimethyl-4,5,6,7-tetrahydro-benzothiazole-2-yl)-guanidine;
N-(6,6-dimethyl-4,5,6,7-tetrahydro-benzothiazole-2-yl)-guanidine;
N-(5-butyl-5,6,7,8-tetrahydro-4H-cycloheptathiazol-2-yl)-guanidine;
N-(4-ethyl-4-methyl-4,5,6,7-tetrahydro-benzothiazole-2-yl)-guanidine;
N-[6-(3,4-dimethoxyphenyl)-4,5,6,7-tetrahydro-benzothiazole-2-yl]-guanidine and its formate;
N-(5-butyl-4,5,6,7-tetrahydro-benzothiazole-2-yl)-guanidine;
N-(6-phenyl-4,5,6,7-tetrahydro-benzothiazole-2-yl)-guanidine;
N-(5-methyl-4,5,6,7-tetrahydro-benzothiazole-2-yl)-guanidine;
N-(4-methyl-4-propyl-4,5,6,7-tetrahydro-benzothiazole-2-yl)-guanidine;
N-(6-propyl-4,5,6,7-tetrahydro-benzothiazole-2-yl)-guanidine;
N-(4-cyclohex-1-enyl-4,5,6,7-tetrahydro-benzothiazole-2-yl)-guanidine and its formate;
N-(4-sec-butyl-4,5,6,7-tetrahydro-benzothiazole-2-yl)-guanidine and its formate; and
N-(4-isobutyl-4-methyl-4,5,6,7-tetrahydro-benzothiazole-2-yl)-guanidine.

Other particularly preferred novel substances are:
N-(6-tert-butyl-4,5,6,7-tetrahydro-benzothiazole-2-yl)-guanidine;
2-guanidino-6-phenyl-4,5,6,7-tetrahydro-benzothiazole-6-carboxylic acid ethyl ester and its formate;
N-[6-(1,1-dimethyl-propyl)-4,5,6,7-tetrahydro-benzothiazole-2-yl]-guanidine;
N-(7-methyl-4,5,6,7-tetrahydro-benzothiazole-2-yl)-guanidine and its formate;
N-[6-(3-methoxy-phenyl)-4,5,6,7-tetrahydro-benzothiazole-2-yl]-guanidine and its formate;
N-(6-thiophene-2-yl-4,5,6,7-tetrahydro-benzothiazole-2-yl)-guanidine and its formate;

N-(5,5,7,7-tetramethyl-4,5,6,7-tetrahydro-benzothiazole-2-yl)-guanidine;
N-[6-(4-fluorophenyl)-4,5,6,7-tetrahydro-benzothiazole-2-yl]-guanidine and its hydrobromide;
2-guanidino-4,5,6,7-tetrahydro-benzothiazole-6-carboxylic acid ethyl ester and its hydrobromide;
N-(4,4-dimethyl-4,5,6,7-tetrahydro-benzothiazole-2-yl)-guanidine;
N-(4-methyl-4,5,6,7-tetrahydro-benzothiazole-2-yl)-guanidine and its formate;
N-(4,5,6,7-tetrahydro-benzothiazole-2-yl-4-spiro-cyclohexane)-guanidine and its formate;
N-(5,6,7,8-tetrahydro-4H-cycloheptathiazol-2-yl)-guanidine;
N-(4-allyl-4,5,6,7-tetrahydro-benzothiazole-2-yl)-guanidine and its formate;
N-(6-methyl-4,5,6,7-tetrahydro-benzothiazole-2-yl)-guanidine;
N-[6-(3-fluorophenyl)-4,5,6,7-tetrahydro-benzothiazole-2-yl]-guanidine and its formate;
N-(6-cyano-6-phenyl-4,5,6,7-tetrahydro-benzothiazole-2-yl)-guanidine and its hydrobromide;
N-(4-phenyl-4,5,6,7-tetrahydro-benzothiazole-2-yl)-guanidine and its formate; and
N-(6,6-diphenyl-4,5,6,7-tetrahydro-benzothiazole-2-yl)-guanidine and its formate.

Novel substances which are also preferred are:
N-[6-(4-methoxy-phenyl)-4,5,6,7-tetrahydro-benzothiazole-2-yl]-guanidine and its hydrobromide;
N-(5-phenyl-5,6,7,8-tetrahydro-4H-cycloheptathiazol-2-yl)-guanidine and its hydrobromide;
N-(6,7-dihydro-4H-pyrano[4,3-d]thiazol-2-yl)-guanidine;
N-(6-benzo[1,3]dioxol-5-yl-4,5,6,7-tetrahydro-benzothiazole-2-yl)-guanidine and its formate;
2-guanidino-4,5,6,7-tetrahydro-benzothiazole-6-carboxylic acid propyl amide and its formate;
N-[6-(4-cyanophenyl)-4,5,6,7-tetrahydro-benzothiazole-2-yl]-guanidine and its formate;
N-(4-benzyl-4,5,6,7-tetrahydro-benzothiazole-2-yl)-guanidine and its formate;
N-(5-methyl-5-phenyl-4,5,6,7-tetrahydro-benzothiazole-2-yl)-guanidine and its formate;
N-[6-(3,5-to-trifluoromethylphenyl)-4,5,6,7-tetrahydro-benzothiazole-2-yl]-guanidine and its formate;
N-(6-o-tolyl-4,5,6,7-tetrahydro-benzothiazole-2-yl)-guanidine and its formate;
N-(6-m-tolyl-4,5,6,7-tetrahydro-benzothiazole-2-yl)-guanidine and its formate;
N-[6-(2-ethyl-phenyl)-4,5,6,7-tetrahydro-benzothiazole-2-yl]-guanidine and its formate;
N-[6-(4-chlorophenyl)-4,5,6,7-tetrahydro-benzothiazole-2-yl]-guanidine and its formate;
2-guanidino-4,5,6,7-tetrahydro-benzothiazole-4-carboxylic acid benzyl amide and its formate;
N-(5,6-dihydro-4H-cyclopentathiazol-2-yl)-guanidine;
N-[6-(4-benzyloxy-phenyl)-4,5,6,7-tetrahydro-benzothiazole-2-yl]-guanidine and its hydrobromide;
2-guanidino-4,5,6,7-tetrahydro-benzothiazole-4-carboxylic acid methyl phenethyl amide and its formate;
N-(6-phenyl-4,5,6,7-tetrahydro-benzothiazole-2-yl-4-spiro-cyclohexane)-guanidine and its hydrobromide;
N-(6-p-tolyl-4,5,6,7-tetrahydro-benzothiazole-2-yl)-guanidine and its formate
2-guanidino-4,5,6,7-tetrahydro-benzothiazole-4-carboxylic acid-(3-methyl-butyl)-amide and its formate; and
N-(4-tert-butyl-6-phenyl-4,5,6,7-tetrahydro-benzothiazole-2-yl)-guanidine.

Other representative examples of the novel substances are:
2-guanidino-4,5,6,7-tetrahydro-benzothiazole-6-carboxylic acid phenyl amide and its formate;
2-guanidino-4,5,6,7-tetrahydro-benzothiazole-4-carboxylic acid butyl ethyl amide and its formate;
N-[4-(2-cyano-ethyl)-4,5,6,7-tetrahydro-benzothiazole-2-yl]-guanidine and its formate;
2-guanidino-4,5,6,7-tetrahydro-benzothiazole-4-carboxylic acid ethyl ester and its hydrobromide;
2-guanidino-4,5,6,7-tetrahydro-benzothiazole-4-carboxylic acid dipropyl amide and its formate;
2-guanidino-4,5,6,7-tetrahydro-benzothiazole-4-carboxylic acid phenyl amide and its formate;
2-guanidino-4,5,6,7-tetrahydro-benzothiazole-6-carboxylic acid allyl amide and its formate;
2-guanidino-4,5,6,7-tetrahydro-benzothiazole-4-carboxylic acid propyl amide and its formate;
N-[4-(piperidine-1-carbonyl)-4,5,6,7-tetrahydro-benzothiazole-2-yl]-guanidine and its formate;
2-guanidino-4,5,6,7-tetrahydro-benzothiazole-4-carboxylic acid allyl amide and its formate;
2-guanidino-4,5,6,7-tetrahydro-benzothiazole-6-carboxylic acid-(3-methyl-butyl)-amide and its formate;
N-[4-(morpholine-4-carbonyl)-4,5,6,7-tetrahydro-benzothiazole-2-yl]-guanidine and its formate; and
2-guanidino-4,5,6,7-tetrahydro-benzothiazole-4-carboxylic acid diisopropyl amide and its formate.

DETAILED DESCRIPTION OF PREFERRED EMBODIMENTS

The term "alkyl", alone or in combination, describes a linear or branched hydrocarbon radical with 1-8 C atoms. Representative, but not limitative, examples of alkyl are methyl, ethyl, n-propyl, isopropyl, n-butyl, tert-butyl, isobutyl (or 2-methylpropyl), n-pentyl (or n-amyl), isopentyl (or isoamyl), n-hexyl n-heptyl, n-octyl and the like. The alkyl radical can carry one or more substituents which are selected independently of each other from alkenyl, alkoxy, alkoxyalkyl, alkoxycarbonyl, alkoxycarbonylalkyl, alkylcarbonyl, alkylcarbonylalkyl, alkylcarbonyloxy, alkylenedioxy, alkylsulphinyl, alkylsulphinylalkyl, alkylsulphonyl, alkylsulphonylalkyl, alkylthio, alkylthioalkyl, alkynyl, amino, aminoalkyl, aminocarbonyl, aminocarbonylalkyl, aryl, arylalkenyl, arylalkyloxy, arylalkyl, aryloxy, aryloxycarbonyl, aryloxycarbonylalkyl, arylsulphinyl, arylsulphinylalkyl, arylsulphonyl, arylsulphonylalkyl, arylthio, arylthioalkyl, carboxy, carboxyalkyl, cyano, cyanoalkyl, formyl, formylalkyl, halogen, haloalkoxy, haloalkyl, heterocyclyl, hydroxy, hydroxyalkyl, mercapto, nitro and the like, and which can be linked with any C atom of the alkyl group.

The term "low alkyl", alone or in combination, describes alkyl groups with 1-4 C atoms. Representative, but not limitative, examples of low alkyl are methyl, ethyl, n-propyl, isopropyl, n-butyl, tert-butyl and the like.

The term "alkenyl", alone or in combination, describes a linear or branched hydrocarbon radical of 2-8 C atoms in which at least one carbon-carbon double bond ($R_aR_bC=CR_cR_d$) is present. $R_a$-$R_d$ describe substituents which are chosen independently of each other from hydrogen, alkyl, alkoxy, alkoxyalkyl, and the like. Representative, but not limitative, examples of alkenyl are ethenyl, 2-propenyl, 2-methyl-2-propenyl, 3-butenyl, 4-pentenyl, 5-hexenyl and the like.

The term "alkylenedioxy", alone or in combination, describes a —O(CH$_2$)$_n$O group, in which n means 1 or 2, the O-atoms being bound to two neighbouring C atoms of the main molecule skeleton. Representative, but not limitative, examples of alkylenedioxy are methylenedioxy, ethylenedioxy and the like.

The term "alkynyl", alone or in combination, describes a linear or branched hydrocarbon radical with 2-8 C atoms, in which at least one carbon-carbon triple bond ($R_a$—C≡C—$R_b$) is present. $R_a$ and $R_b$ describe substituents which are chosen independently of each other from hydrogen, alkenyl, alkoxy, alkoxyalkyl, and the like. Representative, but not limitative, examples of alkynyl are acetylenyl, 1-propynyl, 2-propynyl, 1-butynyl, 3-butynyl, 2-pentynyl and the like.

The term "alkoxy", alone or in combination, describes an alkyl group which is linked via an oxygen bridge. Representative, but not limitative, examples of alkoxy are methoxy, ethoxy, propoxy, 2-propoxy, butoxy, tert-butoxy, pentyloxy, and hexyloxy.

The term "alkoxyalkyl", alone or in combination, describes an alkoxy group which is linked via an alkyl radical. Representative, but not limitative, examples of alkoxyalkyl are tert-butoxymethyl, 2-ethoxyethyl, 2-methoxyethyl, and methoxymethyl.

The term "alkoxycarbonyl", alone or in combination, describes an alkoxy group which is linked via a carbonyl group. Representative, but not limitative, examples of alkoxycarbonyl are methoxycarbonyl, ethoxycarbonyl, tert-butoxycarbonyl and the like.

The term "alkoxycarbonylalkyl", alone or in combination, describes an alkoxycarbonyl group which is linked via an alkyl radical. Representative, but not limitative, examples of alkoxycarbonylalkyl are methoxycarbonylpropyl, ethoxycarbonylbutyl, 2-tert-butoxycarbonylethyl and the like.

The term "alkylcarbonyl", alone or in combination, describes an alkyl group which is linked via a carbonyl group. Representative, but not limitative, examples of alkylcarbonyl are acetyl, 1-oxopropyl, 2,2-dimethyl-1-oxopropyl, 1-oxobutyl, 1-oxopentyl and the like.

The term "alkylcarbonylalkyl", alone or in combination, describes an alkylcarbonyl group which is linked via an alkyl group. Representative, but not limitative, examples of alkylcarbonylalkyl are 2-oxopropyl, 3,3-dimethyl-2-oxopropyl, 3-oxobutyl, 3-oxopentyl and the like.

The term "alkylcarbonyloxy", alone or in combination, describes an alkylcarbonyl group which is linked via an oxygen bridge. Representative, but not limitative, examples of alkylcarbonyloxy are acetyloxy, ethylcarbonyloxy, tert-butylcarbonyloxy and the like.

The term "alkylsulphinyl", alone or in combination, describes an alkyl group which is linked via a sulphinyl group. Representative, but not limitative, examples of alkylsulphinyl are methylsulphinyl, ethylsulphinyl and the like.

The term "alkylsulphinylalkyl", alone or in combination, describes an alkylsulphinyl group which is linked via an alkyl group. Representative, but not limitative, examples of alkylsulphinylalkyl are methylsulphinylmethyl, ethylsulphinylmethyl and the like.

The term "alkylsulphonyl", alone or in combination, describes an alkyl group which is linked via a sulphonyl group. Representative, but not limitative, examples of alkylsulphonyl are methylsulphonyl, ethylsulphonyl and the like.

The term "alkylsulphonylalkyl", alone or in combination, refers to an alkylsulphonyl group which is linked via an alkyl group. Representative, but not limitative, examples of alkylsulphonylalkyl are methylsulphonylmethyl, ethylsulphonylmethyl and the like.

The term "alkylthio", alone or in combination, describes an alkyl group which is linked via a thio group. Representative, but not limitative, examples of alkylthio are methylsulphanyl, ethylsulphanyl, tert-butylsulphanyl, hexylsulphanyl and the like.

The term "alkylthioalkyl", alone or in combination, describes an alkylthio group which is linked via an alkyl group. Representative, but not limitative, examples of alkylthioalkyl are methylsulphanyl-methyl, 2-(ethylsulphanyl)ethyl and the like.

The term "amino", alone or in combination, describes a —$NR_eR_f$ group, in which $R_e$ and $R_f$ are chosen independently from hydrogen, alkyl, aryl, arylalkyl, acyl, alkylcarbonyl, arylcarbonyl, carbamoyl, ureido, formyl, alkylsulphonyl, arylsulphonyl and the like.

The term "aminoalkyl", alone or in combination, describes an amino group which is linked via an alkyl group. Representative, but not limitative, examples of aminoalkyl are aminomethyl, 2-aminoethyl, N-benzyl-N-methyl-aminomethyl, dimethylamino-methyl and the like.

The term "aminocarbonyl", alone or in combination, describes an amino group which is linked via a carbonyl group. Representative, but not limitative, examples of aminocarbonyl are dimethylaminocarbonyl, benzylaminocarbonyl, ethylaminocarbonyl and the like.

The term "aminocarbonylalkyl", alone or in combination, describes an aminocarbonyl group which is linked via an alkyl group. Representative, but not limitative, examples of aminocarbonylalkyl are 2-amino-2-oxoethyl, 2-(benzylamino)-2-oxoethyl, 2-(methylamino)-2-oxoethyl, 4-amino-4-oxobutyl, 4-(dimethylamino)-4-oxobutyl and the like.

The term "aryl", alone or in combination, describes an aromatic carbocyclic group containing at least one aromatic ring, for example phenyl or biphenyl, or condensed ring systems in which at least one ring is aromatic, for example 1,2,3,4-tetrahydronaphthyl, naphthyl, anthryl, phenanthryl, fluorenyl and the like. The aryl group can carry one or more substituents which are chosen independently of each other from alkenyl, alkoxy, alkoxyalkyl, alkoxycarbonyl, alkoxycarbonylalkyl, alkyl, alkylcarbonyl, alkylcarbonylalkyl, alkylcarbonyloxy, alkylenedioxy, alkylsulphinyl, alkylsulphinylalkyl, alkylsulphonyl, alkylsulphonylalkyl, alkylthio, alkylthioalkyl, alkynyl, amino, aminoalkyl, aminocarbonyl, aminocarbonylalkyl, arylalkenyl, arylalkyloxy, arylalkyl, aryloxy, aryloxycarbonyl, aryloxycarbonylalkyl, arylsulphinyl, arylsulphinylalkyl, arylsulphonyl, arylsulphonylalkyl, arylthio, arylthioalkyl, carboxy, carboxyalkyl, cyano, cyanoalkyl, formyl, formylalkyl, halogen, haloalkoxy, haloalkyl, heterocyclyl, hydroxy, hydroxyalkyl, mercapto, nitro and the like.

The term "arylalkenyl", alone or in combination, describes an aryl group which is linked via an alkenyl group. Representative, but not limitative, examples of arylalkenyl are 2-phenylethenyl, 3-phenylpropen-2-yl, 2-naphth-2-ylethenyl and the like.

The term "arylalkoxy", alone or in combination, describes an aryl group which is linked via an alkoxy group. Representative, but not limitative, examples of arylalkoxy are 2-phenylethoxy, 5-phenylpentyloxy, 3-naphth-2-ylpropoxy and the like.

The term "arylalkyl", alone or in combination, describes an aryl group which is linked via an alkyl group. The aryl group can be unsubstituted or substituted. Representative, but not limitative, examples of arylalkyl are benzyl, 2-phenylethyl, 3-phenylpropyl, 2-naphth-2-ylethyl and the like.

The term "aryloxy", alone or in combination, describes an aryl group which is linked via an oxygen bridge. The aryl group can be unsubstituted or substituted. Representative, but not limitative, examples of aryloxy are phenoxy, naphthyloxy, 3-bromophenoxy, 4-chlorophenoxy, 4-methylphenoxy, 3,4-dimethoxyphenoxy and the like. The aryl group can be unsubstituted or substituted as defined.

The term "carbamoyl", alone or in combination, describes a —C(O)NR$_e$R$_f$ group.

The term "thiocarbamoyl", alone or in combination, describes a —C(S)NR$_e$R$_f$ group.

The term "carbonyl", alone or in combination, describes a —C(O)— group.

The term "carboxy", alone or in combination, describes a —CO$_2$H group.

The term "carboxyalkyl", alone or in combination, describes a carboxy group which is linked via an alkyl group. Representative, but not limitative, examples of carboxyalkyl are carboxymethyl, 2-carboxyethyl, 3-carboxypropyl and the like.

The term "cyano", alone or in combination, describes a —C≡N— group.

The term "cyanoalkyl", alone or in combination, describes a cyano group which is linked via an alkyl group. Representative, but not limitative, examples of cyanoalkyl are cyanomethyl, 2-cyanoethyl, 3-cyanopropyl and the like.

The term "cycloalkyl", alone or in combination, describes a saturated cyclic hydrocarbon radical with 3-15 C atoms which can carry one or more substituents. The substituents are independently selected from alkenyl, alkoxy, alkoxyalkyl, alkoxycarbonyl, alkoxycarbonylalkyl, alkyl, alkylcarbonyl, alkylcarbonylalkyl, alkylcarbonyloxy, alkylenedioxy, alkylsulphinyl, alkylsulphinylalkyl, alkylsulphonyl, alkylsulphonylalkyl, alkylthio, alkylthioalkyl, alkynyl, amino, aminoalkyl, aminocarbonyl, aminocarbonylalkyl, aryl, arylalkenyl, arylalkyloxy, arylalkyl, aryloxy, aryloxycarbonyl, aryloxycarbonylalkyl, arylsulphinyl, arylsulphinylalkyl, arylsulphonyl, arylsulphonylalkyl, arylthio, arylthioalkyl, carboxy, carboxyalkyl, cyano, cyanoalkyl, formyl, formylalkyl, halogen, haloalkoxy, haloalkyl, heterocyclyl, hydroxy, hydroxyalkyl, mercapto, nitro and the like. Representative, but not limitative, examples of cycloalkyl are cyclopropyl, cyclobutyl, cyclopentyl, cyclohexyl, cycloheptyl, cyclooctyl. In polycyclic cycloalkyl radicals one of the fused rings can be aromatic, such as for example 1-indanyl, 2-indanyl, tetrahydronaphthyl and the like.

The terms "cycloalkenyl" and "cycloalkinyl" describe cyclic hydrocarbon radicals which contain at least one carbon-carbon double or triple bond. Like the cycloalkyl radicals, these radicals can carry one or more substituents.

The term "formyl", alone or in combination, describes a —C(O)H group.

The term "formylalkyl", alone or in combination, describes a formyl group which is linked via an alkyl group. Representative, but not limitative, examples of formylalkyl are formylmethyl, 2-formylethyl, and the like.

The term "halo" or "halogen", alone or in combination, describes fluorine, bromine, chlorine, and iodine.

The term "haloalkyl", alone or in combination, describes an alkyl group in which at least one hydrogen atom is replaced by halogen. Representative, but not limitative, examples of haloalkyl are chloromethyl, 2-fluoroethyl, trifluoromethyl, pentafluoroethyl, 2-chloro-3-fluoropentyl and the like.

The term "haloalkoxy", alone or in combination, describes an alkoxy group in which at least one hydrogen atom is replaced by halogen. Representative, but not limitative, examples of haloalkoxy are chloromethoxy, 2-fluorethoxy, trifluoromethoxy, pentafluoroethoxy and the like.

The term "heterocyclyl", alone or in combination, describes a monocyclic, bicyclic or polycyclic ring system with up to 15 ring atoms, containing at least one heteroatom independently chosen from nitrogen, oxygen, or sulphur, the ring(s) being able to be saturated, partially unsaturated or unsaturated or aromatic. Representative, but not limitative, examples of heterocyclyl are furyl, imidazolyl, imidazolinyl, imidazolidinyl, isothiazolyl, isoxazolyl, morpholinyl, oxadiazolyl, oxazolyl, oxazolinyl, oxazolidinyl, piperazinyl, piperidinyl, pyranyl, pyrazinyl, pyrazolyl, pyridyl, pyrimidinyl, pyridazinyl, pyrrolyl, pyrrolinyl, pyrrolidinyl, tetrahydrofuranyl, tetrahydrothienyl, thiadiazolyl, thiazolyl, thiazolinyl, thiazolidinyl, thienyl, thiomorpholinyl, 1,1-dioxothiomorpholinyl, benzimidazolyl, benzothiazolyl, benzothienyl, benzoxazolyl, benzofuranyl, indolyl, indolinyl, isobenzofuranyl, isobenzothienyl, isoindolyl, isoindolinyl, isoquinolinyl, quinolinyl and the like. The heterocylyl radicals can carry one or more substituents, these being independently selected from alkenyl, alkoxy, alkoxyalkyl, alkoxycarbonyl, alkoxycarbonylalkyl, alkyl, alkylcarbonyl, alkylcarbonylalkyl, alkylcarbonyloxy, alkylenedioxy, alkylsulphinyl, alkylsulphinylalkyl, alkylsulphonyl, alkylsulphonylalkyl, alkylthio, alkylthioalkyl, alkynyl, amino, aminoalkyl, aminocarbonyl, aminocarbonylalkyl, aryl, arylalkenyl, arylalkyloxy, arylalkyl, aryloxy, aryloxycarbonyl, aryloxycarbonylalkyl, arylsulphinyl, arylsulphinylalkyl, arylsulphonyl, arylsulphonylalkyl, arylthio, arylthioalkyl, carboxy, carboxyalkyl, cyano, cyanoalkyl, cycloalkyl, formyl, formylalkyl, halogen, haloalkoxy, haloalkyl, hydroxy, hydroxyalkyl, mercapto, nitro and the like.

The term "heteroaryl", alone or in combination, is a special case of heterocyclyl and describes a monocyclic, bicyclic or polycylic ring system, in which the or at least one ring is heteroaromatic.

The term "heterocyclylalkenyl", alone or in combination, describes a heterocyclyl group which is linked via an alkenyl group. Representative, but not limitative, examples of heterocyclylalkenyl are 2-pyrido-3-ylethenyl, 3-quinoline-3-ylpropen-2-yl, 5-pyrido-4-ylpentylen-4-yl and the like.

The term "heterocyclylalkoxy", alone or in combination, describes a heterocyclyl group which is linked via an alkoxy group. Representative, but not limitative, examples of heterocyclylalkoxy are 2-pyrido-3-ylethoxy, 3-quinoline-3-ylpropoxy, 5-pyrido-4-ylpentyloxy and the like.

The term "heterocyclylalkyl", alone or in combination, describes a heterocyclyl group which is linked via an alkyl group as defined. Representative, but not limitative, examples of heterocyclylalkyl are 2-pyrido-3-ylmethyl, 2-pyrimidine-2-ylpropyl and the like.

The term "heterocyclyloxy", alone or in combination, describes a heterocyclyl group which is linked via an oxygen bridge. Representative, but not limitative, examples of heterocyclyloxy are pyrido-3-yloxy, quinoline-3-yloxy and the like.

The terms "hydroxy" or "hydroxyl", alone or in combination, describe a —OH group.

The term "hydroxyalkyl", alone or in combination, describes an alkyl group in which at least one hydrogen atom is replaced by a hydroxyl group. Representative, but not limitative, examples of hydroxyalkyl are hydroxymethyl, 2-hydroxyethyl, 3-hydroxypropyl, 2-ethyl-4-hydroxyheptyl and the like.

The term "nitro", alone or in combination, describes a —NO$_2$— group.

The term "oxo", alone or in combination, describes a =O— group.

The term "oxy", alone or in combination, describes a —O— group.

The terms "mercapto" and "thiol" describe a —SH— group.

The terms "thio", "sulphinyl" and "sulphonyl" describe a —S(O)$_n$— group with n=0, 1 and 2.

The compounds defined at the outset of Formula I can be present in free form, as pharmaceutically applicable acid addition salts, as pharmaceutically applicable salts of acid compounds of Formula I with bases, as pharmaceutically applicable esters of hydroxy or carboxy group-containing compounds of Formula I and as hydrates or solvates thereof. The term "pharmaceutically applicable salts" refers to salts which do not reduce the biological effect and properties of the free bases and which are not biologically or otherwise undesirable.

The acid addition salts are formed from the free bases using inorganic acids, such as hydrochloric acid, hydrobromic acid, sulphuric acid, nitric acid, phosphoric acid and the like, preferably hydrochloric acid or hydrobromic acid, or using organic acids, such as acetic acid, propionic acid, glycolic acid, pyruvic acid, oxalic acid, maleic acid, malonic acid, succinic acid, tartaric acid, salicylic acid, citric acid, benzoic acid, mandelic acid, methanesulphonic acid, p-toluenesulphonic acid and the like.

Compounds of Formula I which contain acid groups can form salts with inorganic bases or with organic bases. Preferred salts with inorganic bases are, but not exclusively, sodium, potassium, lithium, ammonium, calcium, magnesium salts and the like. Preferred salts with organic bases are, but not exclusively, salts with primary, secondary and tertiary, optionally substituted amines including all naturally occurring substituted amines, with cyclic amines and with basic ion-exchange resins, such as isopropylamine, trimethylamine, diethylamine, triethylamine, tripropylamine, ethanolamine, lysine, arginine, N-ethylpiperidine, piperidine, polyamine resins and the like. Compounds of Formula I which contain an acid group can also be present as zwitterions.

Pharmaceutically applicable esters of hydroxy or carboxy group-containing compounds of Formula I are also mentioned at the outset. "Pharmaceutically applicable esters" means that in compounds of Formula I corresponding functional groups are derivated to ester groups in such a way that they are transformed back to their active form again in vivo. On the one hand COOH groups can be esterified. Examples of suitable esters of this type are alkyl and aralkylesters. Preferred esters of this type are methyl, ethyl, propyl, butyl and benzylesters and (R/S)-1-[(isopropoxycarbonyl)oxy]ethyl esters. Ethyl esters and the isomeric butylesters are particularly preferred. On the other hand OH— groups can be esterified. Examples of such compounds contain physiologically acceptable and metabolically labile ester groups, such as methoxymethyl esters, methylthiomethyl esters, pivaloyloxymethyl esters and similar ester groups.

Compounds of Formula I were examined in the following test for their affinity to the NPFF receptors:

Hamster cells suitable for neuropeptide FF receptor-binding studies (Chinese Hamster Ovary cells, CHOSP10) which in each case produce the NPFF1 or NPFF2 receptor, were multiplied in standard cell-culture conditions. The cell-culture medium was sucked out and 5 ml of buffer A (5 mM Tris pH=7.4, 1 mM MgCl$_2$) added per 17 cm Petri dish. The cells were scraped off the cell-culture plate and transferred into a 50 ml Falcon vessel. The cells were then centrifuged for 5 minutes at 450 g, resuspended in buffer A once again and mixed for 30 seconds on a Polytron vortex. After centrifugation at 30,000 g for 20 minutes the supernatant was discarded and the membrane pellet taken up in 500 µl buffer C (75 mM Tris pH=7.4, 25 mM MgCl$_2$, 250 mM sucrose, 0.1 mM PMSF, 0.1 mM phenanthroline). The membrane-buffer mixture was then divided into aliquots and deep-frozen. The protein content of an aliquot was determined by the Lowry method.

The binding test was carried out in a final volume of 250 µl. 100 µl membrane-buffer mixture corresponding to 35 µg protein content was mixed with 95 µl binding buffer (50 mM Tris pH 7.4, 60 mM NaCl, 0.1% protease-free BSA, 0.01% NaN$_3$). After addition of 5 µl each of a concentration of test substance per measurement point, 0.2 nM $^{125}$I-Tyr1-NPFF (NEN, NEX381) per measurement point was added in 50 µl. After 90 minutes' incubation at room temperature the samples were sucked out through a GF/C filter (Millipore (MAHFC1H60)) and the filter was washed with ice cold binding buffer with 3 times 300 µl (Packard Filtermate). After addition of 55 µl Microscint 40 (Packard 6013641) scintillation fluid the measurement points were quantified in the gamma counter (Packard, Top Count NXT).

Non-specific binding was ascertained in the presence of 1 µM unmarked neuropeptide FF. Specific binding is defined as the difference between total and non-specific binding. IC$_{50}$ values are defined as that concentration of the antagonist which displaces 50% of the $^{125}$-marked neuropeptide FF. This concentration is ascertained by linear regression analysis after logit/log-transformation of the binding values.

Preferred compounds according to the invention show, in the receptor binding study described above, IC$_{50}$ values below 1000 nM, particularly preferred compounds show IC$_{50}$ values below 100 nM, quite particularly preferred ones, below 50 nM.

The results of the representative compounds of Formula I measured in the biological test described above are summarized in Table 1 below.

TABLE 1

| NPFF1 receptor binding | |
|---|---|
| Compound | Binding NPFF-1 IC50 [□M] |
| N-(5-ethyl-5-methyl-4,5,6,7-tetrahydro-benzothiazole-2-yl)-guanidine | 0.0002 |
| N-(5,5-dimethyl-4,5,6,7-tetrahydro-benzothiazole-2-yl)-guanidine | 0.002 |
| N-(4-tert-butyl-4,5,6,7-tetrahydro-benzothiazole-2-yl)-guanidine | 0.002 |
| N-(5,5-dimethyl-6-phenyl-4,5,6,7-tetrahydro-benzothiazole-2-yl)-guanidine | 0.002 |
| N-(6-isopropyl-4,5,6,7-tetrahydro-benzothiazole-2-yl)-guanidine | 0.004 |
| N-(6,6-dimethyl-4,5,6,7-tetrahydro-benzothiazole-2-yl)-guanidine | 0.004 |
| N-(5,5,7-trimethyl-4,5,6,7-tetrahydro-benzothiazole-2-yl)-guanidine | 0.004 |
| N-(5-butyl-5,6,7,8-tetrahydro-4H-cycloheptathiazol-2-yl)-guanidine | 0.005 |
| N-(5-butyl-4,5,6,7-tetrahydro-benzothiazole-2-yl)-guanidine | 0.005 |
| N-(4-ethyl-4-methyl-4,5,6,7-tetrahydro-benzothiazole-2-yl)-guanidine | 0.005 |
| N-[6-(3,4-dimethoxyphenyl)-4,5,6,7-tetrahydro-benzothiazole-2-yl]-guanidine | 0.005 |
| N-(5-Methyl-4,5,6,7-tetrahydro-benzothiazole-2-yl)-guanidine | 0.006 |
| N-(6-phenyl-4,5,6,7-tetrahydro-benzothiazole-2-yl)-guanidine | 0.006 |

TABLE 1-continued

NPFF1 receptor binding

| Compound | Binding NPFF-1 IC50 [□M] |
|---|---|
| N-(6-propyl-4,5,6,7-tetrahydro-benzothiazole-2-yl)-guanidine | 0.007 |
| N-(4-methyl-4-propyl-4,5,6,7-tetrahydro-benzothiazole-2-yl)-guanidine | 0.007 |
| N-(4-cyclohex-1-enyl-4,5,6,7-tetrahydro-benzothiazole-2-yl)-guanidine | 0.008 |
| N-(4-sec-butyl-4,5,6,7-tetrahydro-benzothiazole-2-yl)-guanidine | 0.009 |
| N-(4-isobutyl-4-methyl-4,5,6,7-tetrahydro-benzothiazole-2-yl)-guanidine | 0.009 |
| N-(6-tert-butyl-4,5,6,7-tetrahydro-benzothiazole-2-yl)-guanidine | 0.010 |

As mentioned at the outset, the substances defined there, because of their capacity to block the neuropeptide FF receptors, are valuable in the treatment of pain, hypersensitivity to pain (hyperalgesia) and chronic, acute, long-lasting or temporary pain, which pain be of operative, traumatic, or pathological origin. Above all they supplement the current treatment methods for chronic pain with the advantage of preventing undesirable opioid tolerance and/or opioid dependence. The compounds can also be used for the regulation of insulin secretion, food intake, memory functions, blood pressure, and electrolyte and energy balance and for the treatment of urinary incontinence.

The substances defined at the outset can be transformed into suitable galenic dosage forms using methods which are generally known and familiar to every person skilled in the art. Such dosage forms are for example tablets, coated tablets, dragées, capsules, injection solutions etc. Suitable excipients and adjuvants are also generally known and familiar to every person skilled in the art for the preparation of such galenic dosage forms. In addition to one or more of the substances defined at the outset these dosage forms can also contain further pharmacologically active compounds.

The dosage of the substances defined at the outset or of the dosage forms containing them is to be matched by the doctor in attendance to the respective needs of the patient. In general a daily dose of 0.1-20 mg, preferably 0.5-5 mg of one of the substances defined at the outset per kg body weight of the patient should be appropriate.

The guanidine derivatives of general Formula I, and the corresponding starting and intermediate products, can be produced using methods known in organic synthesis and isolated and purified using known techniques such as precipitation, chromatography, crystallization, preparative reversed-phase HPLC, etc. Stereoisomer mixtures which may be obtained, such as racemates, can be separated by generally customary methods, preferably by chiral-phase chromatography.

The preparation of the guanidine derivatives of general Formula I takes place according to Diagram 1 below:

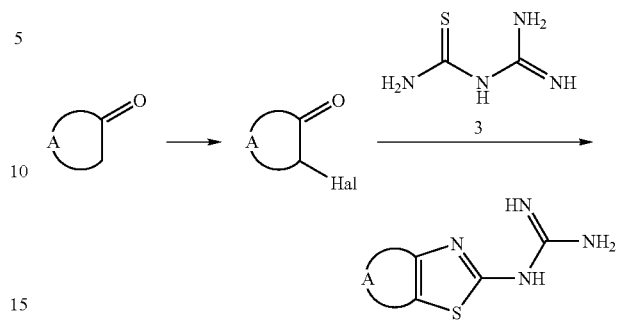

Diagram 1

A compound of Formula 1, in which the nitrogen atom which may be present in A is protected, is halogenated in α-position to form the carbonyl group, whereupon the obtained compound of Formula 2, is subjected to a cyclocondensation with a thiourea derivate such as 2-imino-4-thiobiuret of Formula 3, optionally the protective group located on the nitrogen atom which may be present is split off from the compound obtained, optionally this nitrogen atom is correspondingly substituted with an agent releasing a radical R' and optionally an obtained basic compound is converted into a pharmaceutically applicable acid addition salt, or an obtained compound, containing an acid group, into a pharmaceutically applicable salt with a base, or an obtained hydroxy or carboxy group-containing compound into a pharmaceutically applicable ester and optionally the obtained product is converted into a hydrate or solvate.

Because, in the novel compounds of Formula I, the chain A cannot contain a nitrogen atom, the above remarks concerning a N-protective group, its splitting-off and optional N-substitution of the end-product are irrelevant for the preparation of these novel compounds. Accordingly the novel products according to the invention can be produced by simply halogenating a compound of the above Formula 1 in α-position to form the carbonyl group, subjecting the obtained compound of the above Formula 2 to a cyclocondensation with 2-imino-4-thiobiuret of the above Formula 3 and optionally converting an obtained basic compound into a pharmaceutically applicable acid addition salt, or an obtained compound, containing an acid group, into a pharmaceutically applicable salt with a base, or an obtained hydroxy or carboxy group-containing compound into a pharmaceutically applicable ester and optionally the obtained product into a hydrate or solvate.

Typically the synthesis both of the guanidine derivatives of Formula I and of the corresponding intermediate products is carried out in solution using an organic solvent. The introduction and removal of protective groups takes place with typical methods known to a person skilled in the art (T. W. Greene & P. G. M. Wuts in Protective Groups in Organic Synthesis, Third Edition, John Wiley & Sons, 1999). Generally cycloalkanones (1) can be halogenated with known methods in position α to form the carbonyl group. The following cyclocondensation of α-halo-oxo compounds (2) with a thiourea derivate, such as e.g. 2-imino-4-thiobiuret (3) takes place in known manner and leads to the desired guanidine derivatives of Formula I (J. Med. Chem. 1991, 34(3), 914-918; J. Med. Chem. 1994, 37(8), 1189-1199). Generally, heterocyclic oxo compounds (1) can be converted analogously to the corresponding target compounds of Formula I. It is to be borne in mind that an —NH-group present in A of the starting product (see Formula 4 below) is to be provided with a common protective group (PG), see Diagram 2 below:

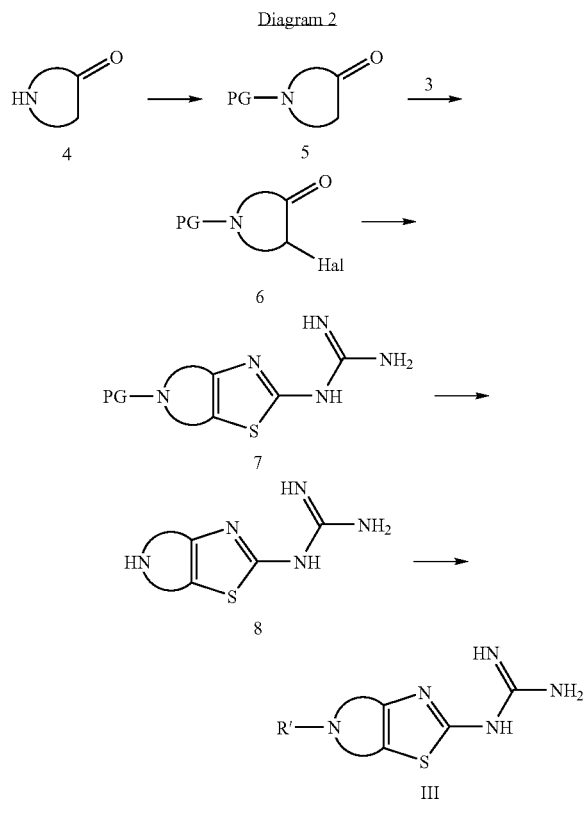

The required cyclic azaketones of Formula 4 are partly known from the literature (Yokoo et al., Bull. Chem. Soc. Japan 1959, 29, 631; Griss et al., DE 2206385, published 10th Feb. 1972) or can be produced analogously to the precursor stage for Example N-07.

The halogenation of 5 and cyclocondensation of 6 with 2-imino-4-thiobiuret (3) to the correspondingly N-protected bicyclic guanidinothiazole 7 takes place under known conditions. After splitting-off of the protective group, which leads to 8, the R'-radicals defined at the outset are converted under known conditions by means of the corresponding R'-releasing reagents in each case, such as e.g. alkylhalides, carboxylic acid halides or anhydrides, or also carboxylic acids in the presence of coupling reagents and with bases as auxiliary reagent, chloroformates, sulphonyl halides, isocyanates, isothiocyanates and the like to the corresponding compound of Formula III.

Suitable organic solvents are those which behave inertly under the chosen reaction conditions. These are preferably ethers, such as diethyl ether, dioxan, tetrahydrofuran or glycoldimethylether; or alcohols, such as for example methanol, ethanol, propanol, isopropanol, butanol, isobutanol or tert-butanol; or hydrocarbons, such as benzene, toluene, xylene, hexane, cyclohexane or petroleum fractions; or halogenated hydrocarbons, such as dichloromethane, trichloromethane, tetrachloromethane, dichloroethylene, trichloroethylene or chlorobenzene; or also ethyl acetate, triethylamine, pyridine, dimethylsulphoxide, dimethylformamide, hexamethylphosphoramide, acetonitrile, acetone or nitromethane. Mixtures of the solvents mentioned can also be used.

Bases which can be used for the described processes, are generally inorganic or organic bases. Preferred are alkali hydroxides, for example sodium or potassium hydroxide, alkaline-earth metal hydroxides, for example barium hydroxide, alkali carbonates such as sodium carbonate or potassium carbonate, alkaline-earth metal carbonates, such as calcium carbonate, or alkali or alkaline-earth metal alkoxides such as sodium or potassium methoxide, sodium or potassium methoxide or potassium-tert-butoxide, or organic amines, e.g. trialkyl-($C_1$-$C_6$)-amines, such as triethylamine, or heterocyclic amines, such as 1,4-diazabicyclo[2.2.2]octane (DABCO), 1,8-diazabicyclo[5.4.0]undec-7-ene (DBU), pyridine, 4-dimethylaminopyridine, N-methyl-piperidine or N-methylmorpholine. It is also possible to use alkali metals, such as sodium, or its hydrides, such as sodium hydride. The bases mentioned can, where expedient, be used as an acid-binding auxiliary.

Dehydrating reagents, for example carbodiimides, such as diisopropylcarbodiimide, dicyclohexylcarbodiimide or N-(3-dimethylaminopropyl)-N'-ethylcarbodiimide-hydrochloride, or carbonyl compounds, such as carbonyldiimidazole, or 1,2-oxazolium compounds, such as 2-ethyl-5-phenyl-isoxazolium-3-sulphonate, or also propane phosphonic acid anhydride or isobutyl chloroformate or benzotriazolyloxy-tris-(dimethylamino)phosphonium-hexafluorophosphate (BOP) or diphenylphosphoramidate or methanesulphonyl chloride, if expedient in the presence of bases, such as triethylamine or N-ethylmorpholine or N-methylpiperidine or diisopropylethylamine, can serve as coupling reagents.

The examples below serve to explain the present invention, but in no way limit it. The products obtained are given in Tables 3 and 4 below.

Example C-01 rac. N-(6-isopropyl-4,5,6,7-tetrahydro-benzothiazole-2-yl)-guanidine 2-imino-4-thiobiuret (5 mmol) is added accompanied by stirring to a solution of 2-bromo-4-isopropyl-cyclohexanone (5 mmol) in ethanol (10 ml) and the reaction mixture is then refluxed for 16 hours. After evaporating-off of the solvent ethyl acetate is added to the residue and the precipitated-out product is isolated by filtering off: $t_R$ 2.75 min (LC-1, one peak); ESI-MS (+/−): m/z 239.25 [M+H]$^+$/237.24 [M−H]$^-$.

2-bromo-4-isopropyl-cyclohexanone (Starting Product for Example C-01)

Bromine (5 mmol) is added dropwise at room temperature to a solution of 4-isopropyl-cyclohexanone (5 mmol) in diethyl ether (10 ml). When the addition is complete the reaction mixture is stirred for another 30 min. After the addition of saturated aqueous sodium sulphite solution. (5 ml) extraction is carried out with diethyl ether, the combined organic phases are concentrated by evaporation after drying over sodium sulphate. The bromoketone obtained as crude product is reacted directly in the next step with 2-imino-4-thiobiuret without further purification.

Analogously to the preparation of Example C-01, the compounds according to Examples C-02 to C-73 in Table 3 are prepared starting from the corresponding α-bromo- or α-chloroketones.

The bromination of the ketones used in Examples C-02 to C-17 takes place in a manner similar to that described above for the preparation of 2-bromo-4-isopropyl-cyclohexanone.

The α-bromoketones are generally reacted as crude products without further characterization.

3-butylcyclohexanone (Precursor-Product for Example C-05)

A solution of copper iodide (6.3 mmol) in dimethyl sulphide (12 ml) is cooled to 50° C. A solution of butyl lithium (6.2 mmol) is added dropwise accompanied by stirring and stirred for a further 5 to 15 mins. The reaction mixture is cooled to −78° C. and then a solution precooled to −78° C. of cyclohex-2-enone (6 mmol), dissolved in dimethyl sulphide (1 ml), is slowly added dropwise. After stirring for one hour at −78° C. the mixture is quenched with saturated aqueous ammonium chloride solution. The reaction mixture which has been heated to room temperature is extracted with diethyl ether. The combined ether phases are washed with saturated aqueous ammonium chloride solution and dried over sodium sulphate. After evaporating-off of the solvent the residue obtained is taken up in hexane, the solution is filtered and concentrated by evaporation. After chromatography of the residue on silica gel with ethyl acetate/hexane 1:4 pure 3-butylcyclohexanone is obtained (Tetrahedron 1989, 45 (2), 425-434).

2-bromo-5-butyl-cyclohexanone (Starting Product for Example C-05)

The bromination of 3-butylcyclohexanone takes place in a manner similar to that described above for the preparation of 2-bromo-4-isopropyl-cyclohexanone. The title compound is reacted as a crude product without further characterization.

2-tert-butyl-6-chlorocyclohexanone (Starting Product for Example C-07)

N-butyl lithium is added dropwise to a solution, cooled to 0° C., of diisopropylamine (5.5 mmol) in dry tetrahydrofuran. After the addition is complete the mixture is cooled to −78° C., and a solution of 2-tert-butylcyclohexanone (5 mmol) in dry tetrahydrofuran (50 ml) is introduced, followed by the addition of p-toluenesulphonyl chloride (5 mmol), also dissolved in dry tetrahydrofuran (50 ml). The reaction mixture is heated to room temperature and after stirring for 30 mins over silica gel filtered with ether as eluant. After concentration by evaporation in a vacuum 2-tert-butyl-6-chlorcyclohexanone (760 mg) is obtained in a yield of 81% (Tet. Lett. 1999, 40(12), 2231-2234).

4,4-dimethylcyclohexanone (Precursor-Product for Example C-1)

A solution of 4,4-dimethyl-cyclohex-2-enone (3 mmol) in ethyl acetate is hydrogenated overnight at room temperature using Pd/C (0.05 mmol) with hydrogen under normal pressure. Filtration over celite and then concentration by evaporation produces 4,4-dimethyl-cyclohexanone (355 mg) in a yield of 94% (J. Org. Chem. 2001, 66 (3), 733-738).

2-bromo-4,4-dimethylcyclohexanone (Starting Product for Example C-11)

The bromination of 4,4-dimethylcyclohexanone takes place in a manner similar to that described above for the preparation of 2-bromo-4-isopropyl-cyclohexanone. The title compound is reacted as a crude product without further characterization.

2-sec-butyl-6-chloro-cyclohexanone (Starting Product for Example C-18)

The chlorination of 2-sec-butylcyclohexanone takes place in a manner similar to that described above for the preparation of 2-tert-butyl-6-chloro-cyclohexanone. The title compound is reacted as a crude product without further characterization.

3-chloro-bicyclohexyl-1'-en-2-one (Starting Product for Example C-19)

The chlorination of 2-(1-cyclohexenyl)cyclohexanone takes place in a manner similar to that described above for the preparation of 2-tert-butyl-6-chloro-cyclohexanone. The title compound is reacted as a crude product without further characterization.

2-benzyl-6-chloro-cyclohexanone (Starting Product for Example C-20)

The chlorination of 2-benzylcyclohexanone takes place in a manner similar to that described above for the preparation of 2-tert-butyl-6-chloro-cyclohexanone. The title compound is reacted as a crude product without further characterization.

2-allyl-6-chloro-cyclohexanone (Starting Product for Example C-21)

The chlorination of 2-allylcyclohexanone takes place in a manner similar to that described above for the preparation of 2-tert-butyl-6-chloro-cyclohexanone. The title compound is reacted as a crude product without further characterization.

2-chloro-6-phenyl-cyclohexanone (Starting Product for Example C-22)

The chlorination of 2-phenylcyclohexanone takes place in a manner similar to that described above for the preparation of 2-tert-butyl-6-chloro-cyclohexanone. The title compound is reacted as a crude product without further characterization.

Ethyl(3-chloro-2-oxo-cyclohexyl)-acetate (Starting Product for Example C-23)

The chlorination of ethyl(2-oxo-cyclohexyl)-acetate takes place in a manner similar to that described above for the preparation of 2-tert-butyl-6-chloro-cyclohexanone. The title compound is reacted as a crude product without further characterization.

3-(3-chloro-2-oxo-cyclohexyl)-propionitrile (Starting Product for Example C-24)

The chlorination of 2-oxo-1-cyclohexanepropionitrile takes place in a manner similar to that described above for the preparation of 2-tert-butyl-6-chloro-cyclohexanone. The title compound is reacted as a crude product without further characterization.

2-chloro-6-methyl-cyclohexanone (Starting Product for Example C-25)

The chlorination of 2-methylcyclohexanone takes place in a manner similar to that described above for the preparation of 2-tert-butyl-6-chloro-cyclohexanone. The title compound is reacted as a crude product without further characterization.

2,2-dimethyl-cyclohexanone (Precursor-Product for Example C-26)

A suspension of potassium hydride (5.5 mmol) and 2-methylcyclohexanone (5 mmol) in dry tetrahydrofuran (10 ml) is stirred for 30 mins at room temperature. Triethylborane (6.25 mmol) is slowly added dropwise and the mixture is stirred for 16 hours at room temperature. After addition of methyl iodide stirring is continued for another 8 hours, the reaction is then quenched with saturated aqueous ammonium chloride solution and twice extracted with diethyl ether. The combined organic phases are dried over sodium sulphate and concentrated to dryness in a vacuum and produce the title compound, which can be reacted without [without] purification (*JACS* 1985, 107, 19, 5391-5396).

6-bromo-2,2-dimethyl-cyclohexanone (Starting Product for Example C-26)

The bromination of 2,2-dimethyl-cyclohexanone takes place in a manner similar to that described above for the preparation of 2-bromo-4-isopropyl-cyclohexanone. The title compound is reacted as a crude product without further characterization.

2-ethyl-2-methyl-cyclohexanone (Precursor-Product for Example C-27)

The alkylation of 2-methylcyclohexanone with ethyl iodide takes place in a manner similar to that described above for the preparation of 2,2-dimethyl-cyclohexanone.

6-bromo-2-ethyl-2-methyl-cyclohexanone (Starting Product for Example C-27)

The bromination of 2-ethyl-2-methyl-cyclohexanone takes place in a manner similar to that described above for the preparation of 2-bromo-4-isopropyl-cyclohexanone. The title compound is reacted as a crude product without further characterization.

2-isobutyl-2-methyl-cyclohexanone (Precursor-Product for Example C-28)

The alkylation of 2-methylcyclohexanone with 1-iodo-2-methyl-propane takes place in a manner similar to that described above for the preparation of 2,2-dimethyl-cyclohexanone.

6-bromo-2-isobutyl-2-methyl-cyclohexanone (Starting Product for Example C-28)

The bromination of 2-isobutyl-2-methyl-cyclohexanone takes place in a manner similar to that described above for the preparation of 2-bromo-4-isopropyl-cyclohexanone. The title compound is reacted as a crude product without further characterization.

2-methyl-2-propyl-cyclohexanone (Precursor-Product for Example C-29)

The alkylation of 2-methylcyclohexanone with 1-iodopropane takes place in a manner similar to that described above for the preparation of 2,2-dimethyl-cyclohexanone.

6-bromo-2-methyl-2-propyl-cyclohexanone (Starting Product for Example C-29)

The bromination of 2-methyl-2-propyl-cyclohexanone takes place in a manner similar to that described above for the preparation of 2-bromo-4-isopropyl-cyclohexanone. The title compound is reacted as a crude product without further characterization.

Example C-30

2-guanidino-4,5,6,7-tetrahydro-benzothiazole-4-carboxylic acid ethyl ester

Analogously to the preparation of Example C-01, 3-bromo-2-oxo-cyclohexane carboxylic acid ethyl ester is reacted with 2-imino-4-thiobiuret to produce the title compound.

3-bromo-2-oxo-cyclohexane carboxylic acid ethyl ester (Starting Product for Example C-30)

The bromination of 2-oxo-cyclohexane carboxylic acid ethyl ester takes place in a manner similar to that described above for the preparation of 2-bromo-4-isopropyl-cyclohexanone. The title compound is reacted as a crude product without further characterization.

Guanidino-4,5,6,7-tetrahydro-benzothiazole-4-carboxylic acid

A suspension of 2-guanidino-4,5,6,7-tetrahydro-benzothiazole-4-carboxylic acid ethyl ester (5 mmol) and sodium hydroxide (20 mmol) in methanol/water (4:1, 10 ml) is stirred overnight at room temperature. The pH is set at 5 by adding 25% hydrochloric acid and the precipitated product is filtered off. In this way the title compound is obtained (671 mg) in a yield of 56%: $t_R$ 0.64 min (LC-1); ESI-MS (+/−): m/z 241.49 $[M+H]^+$/239.37 $[M-H]^-$.

Example C-31

2-guanidino-4,5,6,7-tetrahydro-benzothiazole-4-carboxylic acid benzylamide and its formate 2-guanidino-4,5,6,7-tetrahydro-benzothiazole-4-carboxylic acid (0.1 mmol), diisopropylethylamine (0.2 mmol), O-(benzotriazol-1-yl)-N,N,N',N'-tetramethyluronium-hexafluorophosphate (0.1 mmol) and benzylamine (0.2 mmol) are dissolved in dimethylformamide (0.5 ml) and stirred overnight at room temperature. After removal of the solvent in a vacuum the residue is dispersed in ethyl acetate (1 ml) and 1M aqueous caustic soda solution (0.5 ml). The phases are separated, the organic phase is dried over sodium sulphate, the solvent is evaporated off and the pure title compound is obtained using preparative HPLC (Waters Prep LC equipped with a Waters 600 Controller, Waters 2767 Sample Manager, Waters 996 mass spectrometer and photodiode-array detector).

Analogously to Example C-31 the compounds of Examples C-32 to C-41 listed in Table 3 are produced by reaction of 2-guanidino-4,5,6,7-tetrahydro-benzothiazole-4-carboxylic acid with the corresponding amines in the presence of a coupling reagent such as O-(benzotriazol-1-yl)-N,N,N',N'-tetramethyluronium-hexafluorophosphate.

Example C-42

2-guanidino-4,5,6,7-tetrahydro-benzothiazole-6-carboxylic acid ethyl ester

Analogously to the preparation of Example C-01, 3-bromo-4-oxo-cyclohexane carboxylic acid ethyl ester is reacted with 2-imino-4-thiobiuret to form the title compound.

3-bromo-4-oxo-cyclohexane carboxylic acid ethyl ester (Starting Product for Example C-42)

The bromination of 4-oxo-cyclohexane carboxylic acid ethyl ester takes place in a manner similar to that described above for the preparation of 2-bromo-4-isopropyl-cyclohexanone. The title compound is reacted as a crude product without further characterization.

2-guanidino-4,5,6,7-tetrahydro-benzothiazole-6-carboxylic acid

Analogously to the preparation of 2-guanidino-4,5,6,7-tetrahydro-benzothiazole-4-carboxylic acid, 2-guanidino-4,5,6,7-tetrahydro-benzothiazole-6-carboxylic acid ethyl ester is saponified to form the title compound: $t_R$ 2.49 min (LC-1); ESI-MS (+/−): m/z 241.04 [M+H]$^+$/238.39 [M−2H]$^-$.

In a similar way to Example C-31 the compounds of Examples C-43 to C-46 listed in Table 3 are produced by reaction of 2-guanidino-4,5,6,7-tetrahydro-benzothiazole-4-carboxylic acid with the corresponding amines in the presence of a coupling reagent such as O-(benzotriazol-1-yl)-N,N,N',N'-tetramethyluronium-hexafluorophosphate.

Example C-47

N-(tetrahydro-benzothiazole-2-yl-4-spiro-cyclohexane)-guanidine and its formate Analogously to the preparation of Example C-01, 2-bromo-spiro[5.5]undecan-1-one is reacted with 2-imino-4-thiobiuret to form the title compound.

2-bromo-spiro[5,5]undecan-1-one (Starting Product for Example C-47)

The bromination of spiro[5.5]undecan-1-one takes place in a manner similar to that described above for the preparation of 2-bromo-4-isopropyl-cyclohexanone. The title compound is reacted as a crude product without further characterization.

Spiro[5.5]undecan-1-one (Precursor-Product for Example C-47)

Dibromopentane (5 mmol) is added to a solution of cyclohexanone (5 mmol) and potassium-tert-butanolate (10 mmol) in toluene (7.5 ml) and the reaction mixture is refluxed for 48 hours. After cooling to room temperature 25% hydrochloric acid is added and extraction is carried out with diethyl ether. The combined organic phases produce, after drying over sodium sulphate, removal of the solvent in a vacuum and chromatography of the residue using silica gel (ethyl acetate/heptane, 1:5) pure spiro[5.5]undecan-1-one (*Tetrahedron* 1964, 20, 2553-2573): $t_R$ 1.90 min. (LC-2); ESI-MS (+): m/z 167.27 [M+H]$^+$.

Example C-48

N-(6-phenyl-4,5,6,7-tetrahydro-benzothiazole-2-yl-4-spiro-cyclohexane)-guanidine and its hydrobromide salt The title compound is produced starting from 4-phenyl-spiro[5.5]undecan-1-one instead of spiro[5.5]undecan-1-one in a similar way to N-(tetrahydro-benzothiazole-2-yl-4-spiro-cyclohexane)-guanidine.

4-phenyl-spiro[5.5]undecan-1-one (Precursor-Product for Example C-48)

The preparation of the title compound takes place in a manner similar to that described above for the preparation of spiro[5.5]undecan-1-one: $t_R$ 1.92 min (LC-2); ESI-MS(+): m/z 243.36 [M+H]$^+$. $^1$H NMR (ppm,CDCl$_3$): 7.3 (5H); 3.25 (1H); 2.8 (1H); 2.35 (1H); 2.2 (2H); 1.95 (3H); 1.75 (2H); 1.65 (2H); 1.4 (4H); 1.15 (1H).

4,4-diphenylcyclohexanone (Precursor-Product for Example C-49)

The preparation of 4,4-diphenylcyclohexanone takes place in a manner similar to that described above for the preparation of 4,4-dimethylcyclohexanone: $t_R$ 3.68 min (LC-1); ESI-MS (−): m/z 249.00 [M−H]$^-$.

2-bromo-4,4-diphenylcyclohexanone (Starting Product for Example C-49)

The bromination of 4,4-diphenylcyclohexanone takes place in a manner similar to that described above for the preparation of 2-bromo-4-isopropyl-cyclohexanone. The title compound is reacted as a crude product without further characterization.

3-bromo-4-oxo-1-phenyl-cyclohexane carboxylic acid ethyl ester (Starting Product for Example C-50)

The bromination of 4-oxo-1-phenyl-cyclohexane carboxylic acid ethyl ester takes place in a manner similar to that described above for the preparation of 2-bromo-4-isopropyl-cyclohexanone. The title compound is reacted as a crude product without further characterization.

3-bromo-4-oxo-1-phenyl-cyclohexanecarbonitrile (Starting Product for Example C-51)

The bromination of 4-oxo-1-phenyl-cyclohexanecarbonitrile takes place in a manner similar to that described above for the preparation of 2-bromo-4-isopropyl-cyclohexanone. The title compound is reacted as a crude product without further characterization.

3-bromo-4-arylcyclohexanone (Starting Product[s] for Examples C-52 to C-66)

The bromination of the 4-arylcyclohexanone derivatives (precursor stages for Examples C-52 to C-66) takes place in a manner similar to that described above for the preparation of 2-bromo-4-isopropyl-cyclohexanone. The title compound is reacted as a crude product without further characterization.

Preparation of the 4-arylcyclohexanone derivatives (precursor-products for Examples C-54 to C-66):

1,4-dioxaspiro[4,5]dec-7-en-8-yl-trifluormethane-sulphonic acid ester 1,4-dioxaspiro[4.5]decan-8-one (1 mmol), dissolved in tetrahydrofuran (2 ml), is added to a solution, cooled to −78° C., of lithium-bis-(trimethylsilyl)-amide (1M in tetrahydrofuran, 1.1 mmol) in dry tetrahydrofuran. The mixture is stirred for another 1.5 hours at −78° C. and then a solution of N-phenyl-trifluormethanesulphonimide (1.07 mmol) in tetrahydrofuran (2 ml) is added. Then the mixture is stirred overnight at room temperature and the solvent is then removed in a vacuum. After drying of the residue in a vacuum 1,4-dioxaspiro[4.5]dec-7-en-8-yl-trifluormethane-sulphonic acid ester is obtained, which is immediately reacted again without additional purification (*Tetrahedron* 1999, 55, 14479-14490): $^1$H NMR (ppm,CDCl$_3$): 5.65 (1H); 4 (4H); 2.55 (2H); 2.4 (2H); 1.9 (2H).

4-(4-fluorophenyl)-cyclohexanone (Precursor-Product for Example C-54)

a) 8-(4-fluorophenyl)-1,4-dioxaspiro[4.5]dec-7-ene

In an argon-charged flask, 2M sodium carbonate (4.8 mmol), 1,2-dimethoxyethane (8 ml), 4-fluorophenylboric acid (2.8 mmol), lithium chloride (6 mmol), 1,4-dioxaspiro[4.5]dec-7-en-8-yl-trifluormethane-sulphonic acid ester (2 mmol) and tetrakis(triphenyl-phosphine)palladium (0.1 mmol) are combined and stirred overnight at 80° C. The reaction mixture is concentrated in a vacuum and the residue is dispersed in dichloromethane/2M aqueous sodium carbonate solution. The aqueous phase is extracted with dichloromethane. The combined organic phases are then dried over sodium sulphate and the solvent is evaporated off in a vacuum. From the residue, after column chromatography using silica gel (ethyl acetate/heptane 1:4), pure 8-(4-fluorophenyl)-1,4-dioxaspiro[4.5]dec-7-ene is isolated (*Synthesis* 1993, 735-762): t$_R$ 3.61 min (LC-1); ESI-MS(+): m/z 235.34 [M+H]$^+$. $^1$H NMR (ppm,CDCl$_3$): 7.35 (2H); 6.95 (2H); 5.9 (1H); 4.05 (4H); 2.65 (2H); 2.45 (2H); 1.9 (2H).

b) 8-(4-fluorophenyl)-1,4-dioxaspiro[4.5]decane 8-(4-fluorophenyl)-1,4-dioxaspiro[4.5]dec-7-ene is hydrogenated using Pd/C with hydrogen. After filtering-off of the catalyst over celite and evaporating-off of the solvent, 8-(4-fluorophenyl)-1,4-dioxaspiro[4.5]decane is obtained in a quantitative yield: t$_R$ 3.65 min (LC-1); ESI-MS(+): m/z 237.26 [M+H]$^+$.

c) 4-(4-fluorophenyl)-cyclohexanone 8-(4-fluor-phenyl)-1,4-dioxaspiro[4.5]decane (2 mmol) is dissolved in dioxane (6.5 ml) and treated with 3 ml 50% aqueous sulphuric acid accompanied by stirring at room temperature for 5 hours. After dilution with water (12 ml) extraction is carried out twice with dichloromethane. The raw title compound is obtained from the combined organic phases after drying over sodium sulphate and evaporating-off of the solvent in a vacuum (*Tetrahedron* 1998, 54, 15509-15524): t$_R$ 3.44 min (LC-1); ESI-MS(+): m/z 193.29 [M+H]$^+$.

The preparation of the precursor-products for Examples C-55 to C-66 takes place in a manner similar to that described above for the preparation of 4-(4-fluorophenyl)-cyclohexanone.

4-o-tolyl-cyclohexanone (Precursor-Product for Example C-55)

$^1$H NMR (ppm,CDCl$_3$): 7.3 (2H); 7.1 (2H); 3.15 (1H); 2.45 (4H); 2.35 (3H); 2.1 (2H); 1.85 (2H); 1.65 (2H); 1.4 (4H); 1.15 (1H).

4-(2-ethyl-phenyl)-cyclohexanone (Precursor-Product for Example C-56)

t$_R$ 3.62 min (LC-1); ESI-MS (+): m/z 203.29 [M+H]$^+$.

4-(3,4-dimethoxyphenyl)-cyclohexanone (Precursor-Product for Example C-57)

t$_R$ 3.43 min (LC-1); ESI-MS (+): m/z 235.28 [M+H]$^+$.

4-(4-cyanophenyl)-cyclohexanone (Precursor-Product for Example C-58)

t$_R$ 1.92 min (LC-2); ESI-MS (+): m/z 200.33 [M+H]$^+$.

4-(3,5-bis-trifluormethylphenyl)-cyclohexanone (Precursor-Product for Example C-59)

t$_R$ 2.46 min (LC-2); ESI-MS (+): m/z 311.29 [M+H]$^+$.

4-p-tolyl-cyclohexanone (Precursor-Product for Example C-60)

t$_R$ 2.11 min (LC-2); ESI-MS (+): m/z 189.32 [M+H]$^+$.

4-m-tolyl-cyclohexanone (Precursor-Product for Example C-61)

t$_R$ 2.12 min (LC-2); ESI-MS (+): m/z 189.32 [M+H]$^+$.

4-(3-methoxy-phenyl)-cyclohexanone (Precursor-Product for Example C-62)

t$_R$ 2.08 min (LC-2); ESI-MS (+): m/z 205.35 [M+H]$^+$.

4-(4-chloro-phenyl)-cyclohexanone (Precursor-Product for Example C-63)

t$_R$ 2.26 min (LC-2); ESI-MS (+): m/z 209.23 [M+H]$^+$.

4-(3-fluorophenyl)-cyclohexanone (Precursor-Product for Example C-64)

t$_R$ 2.11 min (LC-2); ESI-MS (+): m/z 193.26 [M+H]$^+$.

4-thiophene-2-yl-cyclohexanone (Precursor-Product for Example C-65)

t$_R$ 2.05 min (LC-2); ESI-MS (+): m/z 219.29 [M+H]$^+$.

4-benzo[1,3]dioxol-5-yl-cyclohexanone (Precursor-Product for Example C-66)

t$_R$ 2.05 min (LC-2); ESI-MS (+): m/z 181.23 [M+H]$^+$.

2-bromo-5,5-dimethyl-cyclohexanone (Starting Product for Example C-67); 2-bromo-5-ethyl-5-methyl-cyclohexanone (Starting Product for Example C-68) and 2-bromo-5-methyl-5-phenyl-cyclohexanone (Starting Product for Example C-69)

The bromination of 3,3-dimethyl-cyclohexanone, 3-ethyl-3-methyl-cyclohexanone, and 3-methyl-3-phenyl-cyclohexanone respectively (precursor stages of Examples C-67 to C-69) takes place in a manner similar to that described above for the preparation of 2-bromo-4-isopropyl-cyclohexanone. The title compounds are reacted as crude products without further characterization.

2-bromo-5,5-dimethyl-4-phenyl-cyclohexanone (Starting Product for Example C-70)

The bromination of 3,3-dimethyl-4-phenyl-cyclohexanone takes place in a manner similar to that described above for the preparation of 2-bromo-4-isopropyl-cyclohexanone. The title compound is reacted as a crude product without further characterization.

3,3-dimethyl-4-phenyl-cyclohexanone (Precursor Stage of Example C-70)

Lithium chloride (0.6 mmol) and copper iodide (0.3 mmol) are introduced first under argon in dry tetrahydrofuran (18 ml). At 0° C. 3-methyl-4-phenylcyclohex-2-enone (3 mmol) is added and stirring continues for another 10 min at this temperature. Then a solution of methylmagnesium bromide (3.6 mmol) is slowly added dropwise and the reaction mixture is maintained at 0° C. for 3 hours accompanied by stirring. The reaction is stopped by adding saturated aqueous ammonium chloride solution. The mixture is extracted with diethyl ether. The title compound is obtained from the combined organic phases after drying over sodium sulphate and evaporating-off of the solvent in a vacuum (J. Organom. Chem. 1995, 502, $C_5$-$C_7$): $t_R$ 2.36 min (LC-2); ESI-MS (+): m/z 203.35 [M+H]$^+$.

2-bromo-3-methyl-cyclohexanone (Starting Product for Example C-71)

A solution of N-bromosuccinimide (0.48 mmol) and sodium acetate (0.04 mmol) in THF/water (1:1, 5.2 ml) is cooled to 0° C. and trimethyl-(3-methyl-cyclohex-1-enyloxy)-silane (0.4 mmol, 80% pure) is added dropwise. The reaction mixture is heated to room temperature and stirring is continued overnight. After addition of water extraction is carried out with ethyl acetate. The title compound is obtained from the combined organic phases after drying over sodium sulphate and evaporating-off of the solvent in a vacuum (JOC 1997, 62, 19, 6692-6696).

Trimethyl-(3-methyl-cyclohex-1-enyloxy)-silane (Precursor-Product for Example C-71)

Lithium chloride (2 mmol) and copper iodide (1 mmol) are introduced first under argon in tetrahydrofuran (5.6 ml) and cooled to −78° C. Cyclohex-2-enone (1 mmol) and trimethylsilyl chloride (1.1 mmol) are added and the solution is stirred for another 10 min. Then a solution of methylmagnesium bromide (1.2 mmol) is slowly added dropwise. After stirring for 3 hours at −78° C. saturated aqueous ammonium chloride solution is added and extraction is carried out with ether. The combined organic phases are dried over sodium sulphate and the solvent is removed in a vacuum. The crude product obtained contains according to LC-MS 80% trimethyl-(3-methyl-cyclohex-1-enyloxy)-silane and 20% of the starting compound and is used in the subsequent reaction without further purification (J. Organom. Chem. 1995, 502, $C_5$-$C_7$): $^1$H NMR (ppm, CDCl$_3$): 4.75 (1H); 2.25 (1H); 1.95 (2H); 1.75 (2H); 1.05 (1H); 0.95 (3H); 0.2 (9H).

2-bromo-6-phenyl-cycloheptanone (Starting Product for Example C-72)

The bromination of 3-phenylcycloheptanone takes place in a manner similar to that described above for the preparation of 2-bromo-4-isopropyl-cyclohexanone. The title compound is reacted as a crude product without further characterization.

2-tert-butyl-6-chloro-4-phenyl-cyclohexanone (Starting Product for Example C-73)

The chlorination of 2-tert-butyl-4-phenyl-cyclohexanone takes place in a manner similar to that described above for the preparation of 2-tert-butyl-6-chloro-cyclohexanone. The title compound is reacted as a crude product without further characterization.

2-tert-butyl-4-phenyl-cyclohexanone (Precursor Stage for Example C-73)

a) Trimethyl-(4-phenyl-cyclohex-1-enyloxy)-silane sodium iodide (12.4 mmol) dissolved in acetonitrile (12.4 ml), is added dropwise at room temperature to a solution of 4-phenylcyclohexanone (10 mmol) in hexane (10 ml), followed by triethylamine (12.4 mmol) and trimethylchlorosilane (12.4 mmol). After stirring for two hours cold pentane and ice water are added. The aqueous phase is extracted with hexane. The combined organic phases are washed with ice water, dried over sodium sulphate and the solvent is removed in a vacuum. Trimethyl-(4-phenyl-cyclohex-1-enyloxy)-silane (1.8 g) is obtained in pure form in a yield of 73% (Tetrahedron 1987, 43, 9, 2075-2088): $t_R$ 2.29 min (LC-2); ESI-MS (+): m/z 247.27 [M+H]$^+$.

b) 2-tert-butyl-4-phenyl-cyclohexanone

Trimethyl-(4-phenyl-cyclohex-1-enyloxy)-silane (7.27 mmol) and tert-butyl chloride (7.85 mmol) are introduced first in dichloromethane under nitrogen and cooled to −45° C. A solution, also cooled to −45° C., of titanium tetrachloride (7.63 mmol) in dichloromethane (3.6 ml) is added, and stirring is continued for 3 hours at this temperature. The reaction mixture is diluted with dichloromethane and washed with ice water. The organic phase is dried over sodium sulphate and the solvent is removed in a vacuum. Column chromatography (ethyl acetate/heptane 1:4) of the residue produces the title compound (250 mg) in a yield of 15% (Angew Chem Int Ed Engl 1978, 17, 1, 48-49). $^1$H NMR (ppm, CDCl$_3$): 7.35 (5H); 3.15 (1H); 2.55 (1H); 2.4 (3H); 2.25 (1H); 2 (1H); 1.8 (1H); 1.05 (9H).

Example N-01

2-guanidino-6,7-dihydro-4H-thiazolo[5,4-c]pyridine-5-carboxylic acid tert-butyl ester Analogously to the preparation of Example C-01, 3-bromo-4-oxo-piperidine-1-carboxylic acid tert-butyl ester is reacted with 2-imino-4-thiobiuret to form the title compound. $t_R$ 2.55 min (LC-1); ESI-MS (+): m/z 298.25 [M+H]$^+$.

3-bromo-4-oxo-piperidine-1-carboxylic acid tert-butyl ester (Starting Product for Example N-01)

The bromination of 4-oxo-piperidine-1-carboxylic acid tert-butyl ester takes place in a manner similar to that described above for the preparation of 2-bromo-4-isopropyl-cyclohexanone. The title compound is reacted as a crude product without further characterization.

N-(4,5,6,7-tetrahydro-thiazolo[5,4-c]pyridine-2-yl)-guanidine (Splitting-Off of the Protective Group from the Product According to Example N-01, 2-guanidino-6,7-dihydro-4H-thiazolo[5,4-c]pyridine-5-carboxylic acid tert-butyl ester)

2-guanidino-6,7-dihydro-4H-thiazolo[5,4-c]pyridine-5-carboxylic acid tert-butyl ester (9.6 mmol) is suspended in a solution of ethanol (10 ml) and concentrated hydrochloric acid (3.8 ml) and stirred for 3 hours at room temperature. After filtration, the product is precipitated by adding ethyl acetate to the clear solution. The white precipitate is filtered off, washed with ethyl acetate and then dried in a vacuum. The title compound is obtained in pure form (1.63 g) as dihydrochloride salt in a yield of 62%: $t_R$ 0.83 min (LC-1); ESI-MS (−): m/z 232.23 [M−H]$^−$.

Example N-02

N-(5-hexyl-4,5,6,7-tetrahydro-thiazolo[5,4-c]pyridine-2-yl)-guanidine 1-bromohexane (0.11 mmol) is added to a suspension of N-(4,5,6,7-tetrahydro-thiazolo[5,4-c]pyridine-2-yl)-guanidine (0.1 mmol) and caesium carbonate (0.22 mmol) in dimethylformamide (0.3 ml) and the reaction mixture is stirred overnight at room temperature. After adding 2M caustic soda solution (1 ml) the mixture is extracted with ethyl acetate, the combined organic phases are dried over sodium sulphate and then concentrated by evaporation, the title compound being obtained in pure form.

Analogously to Example N-02 the compounds of Examples N-03 to N-10 listed in Table 4 are produced by reaction of N-(4,5,6,7-tetrahydro-thiazolo[5,4-c]pyridine-2-yl)-guanidine with the corresponding alkylhalides ("R'-reagents").

Example N-07

N-(5-benzyl-5,6,7,8-tetrahydro-4H-thiazolo[4,5-c]azepine-2-yl)-guanidine

Using an alternative method, analogously to the preparation of Example 1,1-benzyl-4-bromo-azepan-3-one is reacted with 2-imino-4-thiobiuret to form the title compound.

1-benzyl-azepan-3-one (Precursor-Product of Example N-07)

a) 5-(benzyl-ethoxycarbonylmethyl-amino)-pentanoic acid

N-benzylglycine ethyl ester (1.87 ml) and 5-bromovaleric acid ethyl ester (1.92 ml) are dissolved in dimethylformamide (100 ml) and stirred in the presence of potassium carbonate (1.66 g) for 2 days at room temperature. The reaction is quenched with saturated aqueous ammonium chloride solution, and extraction is carried out with ethyl acetate. After drying over sodium sulphate the combined organic phases are concentrated by evaporation. From the obtained residue, 5-(benzyl-ethoxycarbonylmethyl-amino)-pentanoic acid is isolated in a yield of 30% by chromatography using silica gel (ethyl acetate/heptane 1:5).

b) 1-benzyl-azepan-3-one

A suspension of potassium tert-butylate (336 mg) in toluene (2.5 ml) is refluxed for 10 min. Then 5-(benzyl-ethoxycarbonylmethyl-amino)-pentanoic acid (695 mg) in toluene (1 ml) is slowly added to the suspension and when the addition is complete the mixture is refluxed for another 1.5 hours. After cooling to room temperature 25% hydrochloric acid (1 ml) is added. The organic phase is separated off and washed with 25% hydrochloric acid (4×1 ml). The combined hydrochloric-acid aqueous phases are then refluxed for 5 hours. After cooling to room temperature the solution is made alkaline (pH 11) with 2N caustic soda solution and extraction is carried out with ethyl acetate. The combined organic phases are concentrated by evaporation after drying over sodium sulphate. The obtained residue produces, after chromatography using silica gel (ethyl acetate/heptane 1:5) the desired title compound (197 mg) in a yield of 45% (*Bull. Chem. Soc. Jpn.* 1956, 29, 631-632; DE2206385).

1-benzyl-4-bromo-azepan-3-one (Starting Product for Example N-07)

The bromination of 1-benzyl-azepan-3-one takes place in a manner similar to that described above for the preparation of 2-bromo-4-isopropyl-cyclohexanone. The title compound is reacted as a crude product without further characterization.

Example N-11

N-(pentanoyl-4,5,6,7-tetrahydro-thiazolo[5,4-c]pyridine-2-yl)-guanidine

Diisopropylethylamine (0.22 mmol) and then pentanoyl chloride (0.11 mmol) are added to a stirred suspension of N-(4,5,6,7-tetrahydro-thiazolo[5,4-c]pyridine-2-yl)-guanidine-dihydrochloride (0.1 mmol) in dimethylformamide (0.7 ml) and the reaction mixture is stirred for another 16 hours at room temperature. After the addition of 2M caustic soda solution (1 ml) extraction is carried out with ethyl acetate. The combined organic phases produce the pure title compound after drying over sodium sulphate and concentrating to dryness.

Analogously to Example N-11, the compounds of Examples N-13 to N-33 listed in Table 4 are produced by reaction of N-(4,5,6,7-tetrahydro-thiazolo[5,4-c]pyridine-2-yl)-guanidine with the corresponding acid chlorides ("R'-reagents").

Example N-12

N-(5-but-3-enoyl-4,5,6,7-tetrahydro-thiazolo[5,4-c]pyridine-2-yl)-guanidine Diisopropylethylamine (0.22 mmol), vinyl acetic acid (0.11 mmol) and benzotriazolyloxy-tris-(dimethylamino)phosphonium-hexafluorophosphate (0.11 mmol) are added successively to a stirred suspension of N-(4,5,6,7-tetrahydro-thiazolo[5,4-c]pyridine-2-yl)-guanidine-dihydrochloride (0.1 mmol) in dimethylformamide (0.7 mL), and the reaction mixture is stirred for 16 hours at room temperature. After the addition of 2M caustic soda solution (1 ml) there is extraction with ethyl acetate. The combined organic phases produce the pure title compound after drying over sodium sulphate and concentrating to dryness.

Analogously to Example N-12 the compounds of Examples N-19 to N-21 listed in Table 4 are realized by reaction of N-(4,5,6,7-tetrahydro-thiazolo[5,4-c]pyridine-2-yl)-guanidine with the corresponding carboxylic acids ("R'-reagents") in the presence of benzotriazolyloxy-tris-(dimethylamino)phosphonium-hexafluorophosphate as coupling reagent.

Example N-22

2-guanidino-6,7-dihydro-4H-thiazolo[5,4-c]pyridine-5-carboxylic acid benzyl ester Benzyl chloroformate is added to a stirred suspension of N-(4,5,6,7-tetrahydro-thiazolo[5,4-c]pyridine-2-yl)-guanidine (0.1 mmol) and diisopropylethylamine (0.22 mmol) in dimethylformamide (0.7 ml) and the mixture is stirred for another 3 hours at room temperature. After the addition of saturated aqueous sodium carbonate solution extraction is carried out with ethyl acetate; the combined organic phases produce the pure title compound after drying over sodium sulphate and complete evaporation of the solvent.

Analogously to Example N-22 the compound of Example N-23 listed in Table 4 is produced by reaction of N-(4, 5, 6, 7-tetrahydro-thiazolo[5,4-c]pyridine-2-yl)-guanidine with butyl chloroformate ("R'-reagent").

Example N-24

N-[5-(propane-2-sulphonyl)-4,5,6,7-tetrahydro-thiazolo[5,4-c]pyridine-2-yl)]-guanidine Propane-2-sulphonyl chloride is added to a stirred suspension of N-(4,5,6,7-tetrahydro-thiazolo[5,4-c]pyridine-2-yl)-guanidine (0.1 mmol) and diisopropylethylamine (0.22 mmol) in dimethylformamide (0.7 ml) and the mixture is stirred for another 16 hours at room temperature. After the addition of 2M caustic soda solution (1 ml) extraction is carried out with ethyl acetate; the combined organic phases produce [from] the pure title compound after drying over sodium sulphate and complete evaporation of the solvent.

Analogously to Example N-24 the compounds of Examples N-25 and N-26 listed in Table 4 are produced by reaction of N-(4,5,6,7-tetrahydro-thiazolo[5,4-c]pyridine-2-yl)-guanidine with the corresponding sulphonyl chlorides ("R'-reagents").

Example N-27

2-guanidino-6,7-dihydro-4H-thiazolo[5,4-c]pyridine-5-carboxylic acid phenyl amide Diisopropylethylamine (0.2 mmol) and, after 5 min, phenyl isocyanate (0.11 mmol) are added to a suspension of N-(4,5,6,7-tetrahydro-thiazolo[5,4-c]pyridine-2-yl)-guanidine dihydrochloride (0.1 mmol) in dimethylformamide (0.5 ml). The reaction mixture is stirred for another 3 hours at room temperature. Then saturated aqueous sodium carbonate solution is added and extraction is carried out with ethyl acetate. The pure title compound is obtained after drying of the combined organic phases over sodium sulphate and removal of the solvent in a vacuum.

Analogously to Example N-27 the compounds of Examples N-28 and N-29 listed in Table 4 are produced by reaction of N-(4,5,6,7-tetrahydro-thiazolo[5,4-c]pyridine-2-yl)-guanidine dihydrochloride with the "R'-reagents" tert-butyl isocyanate, and pentyl isocyanate respectively.

Example N-30

2-guanidino-6,7-dihydro-4H-thiazolo[5,4-c]pyridine-5-thiocarboxylic acid benzyl amide Benzylamine (0.1 mmol), dissolved in dimethylformamide (0.3 ml), is added under argon to a solution of 1'-thiocarbonyldiimidazole (0.1 mmol) in dimethylformamide (0.5 ml). After stirring for 2.5 hours at room temperature a solution of N-(4,5,6,7-tetrahydro-thiazolo[5,4-c]pyridine-2-yl)-guanidine dihydrochloride (0.1 mmol) and diisopropylethylamine (0.2 mmol) in dimethylformamide are added successively to the reaction mixture. This is stirred for another 16 hours at room temperature and then quenched with saturated aqueous sodium carbonate solution. There is extraction with ethyl acetate and the combined organic phases are dried over sodium sulphate. After removal of the solvent in a vacuum the pure title compound is obtained (*Bioog. Med. Chem. Lett.* 2002, 12, 337-340).

Analogously to Example N-30 the compounds of Examples N-31 to N-33 listed in Table 4 are produced by reaction of N-(4,5,6,7-tetrahydro-thiazolo[5,4-c]pyridine-2-yl)-guanidine dihydrochloride with the corresponding amines in the presence of 1'-thiocarbonyldiimidazole.

Preparative LC-MS

Preparative separations of mixtures of substances are carried out on a preparative LC-MS apparatus (Waters Prep LC-MS equipped with a Waters 600 Controller, Waters 2767 Sample Manager, Waters 996 mass spectrometer and photo-diode-array detector). An Xterra Prep MS C18 column (5 μm particle size, length 50 mm, diameter 19 mm) is used, with a linear gradient of water/0.06% formic acid (A) and acetonitrile/0.06% formic acid (B) and a flow rate of 20 ml/min.

Analytical Methods

The $^1$H-NMR-spectra are measured on a Varian Oxford 300 spectrometer at 300 K; the chemical shift δ is given in ppm deep field shifted from the tetramethylsilane signal as reference, with the residual signals of deuterated dimethyl sulphoxide (δ(H) 2.49 ppm), deuterated chloroform (δ(H) 7.24 ppm) and deuterium oxide serving as internal standard.

TABLE 2

1H-NMR data of selected compounds of Formula I.

| Example | Chemical shift in ppm (Integral) | Solvent |
|---|---|---|
| C-02 | 8(4H); 2.65(3H); 2.15(1H); 1.85(2H); 1.4(1H); 1(3H) | DMSO-$d_6$ |
| C-05 | 6.8(4H); 2.5(4H); 2.05(1H); 1.85(1H); 1.65(1H); 1.3(6H), 0.95(3H) | DMSO-$d_6$ |
| C-06 | 6.8(4H); 2.75(1H); 2.45(4H); 1.8(2H); 1.45(2H); 1.2(6H), 0.95(3H) | $D_2O$ |
| C-09 | 8.1(4H); 7.3(4H); 7.2(1H); 2.95(2H); 2.75(3H); 2(3H) | DMSO-$d_6$ |
| C-12 | 7(4H); 2.75(1H); 2.45(1H); 2.25(1H); 1.55(1H); 1.15(1H); 1.1(3H); 1(3H); 0.85(3H) | DMSO-$d_6$ |
| C-24 | 8.3(4H); 7.4(5H); 4.35(2H); 4.25(2H); 3.55(2H); 2.9(2H); 2.1(2H) | DMSO-$d_6$ |

TABLE 2-continued

1H-NMR data of selected compounds of Formula I.

| Example | Chemical shift in ppm (Integral) | Solvent |
|---|---|---|
| C-38 | 8.1(1H); 7.65(1H); 6.9(4H); 3.5(1H); 3.3(1H); 1.95–1.5(10H); 1.15(5H) | DMSO-$d_6$ |
| C-42 | 8.1(4H); 4.1(2H); 2.85(3H); 2.65(2H); 2.1(1H); 1.85(1H); 1.15(3H) | DMSO-$d_6$ |
| C-50 | 8.1(4H); 7.3(5H); 4.05(2H); 3.45(1H); 3.1(1H); 2.65(1H); 2.4(3H); 1.05(3H) | DMSO-$d_6$ |
| C-54 | 8.1(4H); 7.35(2H); 7.1(2H); 3(2H); 2.7(3H); 2(2H) | DMSO-$d_6$ |
| C-57 | 8.1(4H); 6.85(3H); 3.75(3H); 3.7(3H); 2.95(2H); 2.7(3H); 2(2H) | DMSO-$d_6$ |
| C-71 | 2.8(1H); 2.5(2H); 1.85(2H); 1.6(1H); 1.3(1H); 1.15(3H) | $CDCl_3$ |
| N-07 | 8.3(4H); 7.4(5H); 4.35(2H); 4.25(2H); 3.55(2H); 2.9(2H); 2.05(2H) | $D_2O$ |
| N-08 | 6.8(4H); 3.05(2H); 3(2H); 2.7(3H); 2.5(2H) | DMSO-$d_6$ |
| N-13 | 6.8(4H); 4.5(2H); 3.75(2H); 2.95(1H); 2.6(1H); 2.5(1H); 1(6H) | DMSO-$d_6$ |
| N-22 | 7.3(5H); 6.8(4H); 5.1(2H); 4.45(2H); 3.7(2H); 2.55(2H) | DMSO-$d_6$ |
| N-26 | 7(4H); 4.2(2H); 3.45(2H); 2.9(3H); 2.65(2H) | DMSO-$d_6$ |
| N-29 | 6.8(4H); 6.55(1H); 4.3(2H); 3.6(2H); 3(2H); 2.5(2H); 1.4(2H); 1.25(4H); 0.85(3H) | DMSO-$d_6$ |
| N-30 | 8.35(1H); 7.25(5H); 6.8(4H); 4.85(2H); 4.8(1H); 4.1(2H); 2.6(2H) | DMSO-$d_6$ |

The compounds produced are analyzed by means of reversed-phase HPLC, on a Waters Alliance LC, equipped with a UV-detector and a MassLynx-NT mass spectrometer.

LC-1: GROM-SIL 120 ODS-4 HE HPLC column (particle size 3 μm, column length 30 mm, diameter 2 mm), with a linear gradient with water/0.06% formic acid (A) and acetonitrile/0.06% formic acid (B) of 5% to 95% B in 3 min. with a flow rate of 0.75 ml/min.

LC-2: XTerra MS C18 HPLC column (particle size 5 μm, column length 50 mm, diameter 2.1 mm), with a linear gradient with water/0.06% formic acid (A) and acetonitrile/0.06% formic acid (B) of 5% to 95% B in 2.5 min. with a flow rate of 0.75 ml/min.

TABLE 3

Analytical data for Examples C-01 to C-73

| Ex-ample | Structure | Name | Starting product | Empirical formula Molecular weight | $t_R$ [min] (HPLC method) | MS data m/z [M + H]+/[M − H]− |
|---|---|---|---|---|---|---|
| C-01 | 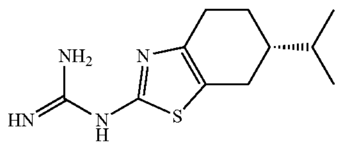 | N-(6-isopropyl-4,5,6,7-tetrahydro-benzothiazole-2-yl)-guanidine | 4-isopropyl-cyclohexanone | C11H18N4S 238.4 | 2.75 (LC-1) | 239.25/237.24 |
| C-02 | 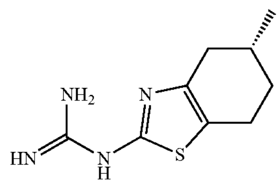 | N-(5-methyl-4,5,6,7-tetrahydro-benzothiazole-2-yl)-guanidine | 3-methyl-cyclohexanone | C9H14N4S 210.3 | 2.86 (LC-1) | 211.25/209.26 |
| C-03 | 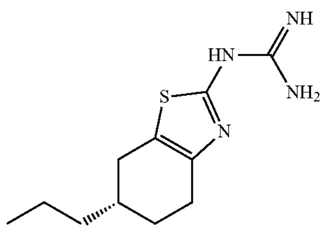 | N-(6-propyl-4,5,6,7-tetrahydro-benzothiazole-2-yl)-guanidine | 4-n-propyl-cyclohexanone | C11H18N4S 238.4 | 2.79 (LC-1) | 239.2/237.27 |
| C-04 | 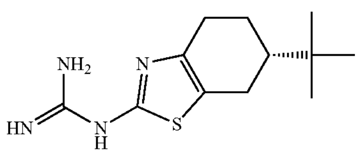 | N-(6-tert-butyl-4,5,6,7-tetrahydro-benzothiazole-2-yl)-guanidine | 4-tert-butyl-cyclohexanone | C12H20N4S 252.4 | 3.06 (LC-1) | 253.28/251.36 |

TABLE 3-continued

Analytical data for Examples C-01 to C-73

| Example | Structure | Name | Starting product | Empirical formula Molecular weight | $t_R$ [min] (HPLC method) | MS data m/z $[M + H]^+/[M - H]^-$ |
|---|---|---|---|---|---|---|
| C-05 | 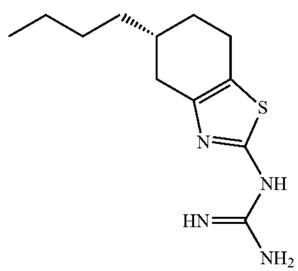 | N-(5-butyl-4,5,6,7-tetrahydro-benzothiazole-2-yl)-guanidine | 3-butyl-cyclohexanone | C12H20N4S 252.4 | 3.19 (LC-1) | 253.31/251.32 |
| C-06 | 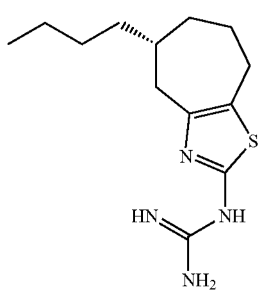 | N-(5-butyl-5,6,7,8-tetrahydro-4H-cycloheptatthiazol-2-yl)-guanidine | 3-butyl-cycloheptanone | C13H22N4S 266.4 | 3.2 (LC-1) | 267.35/265.36 |
| C-07 | 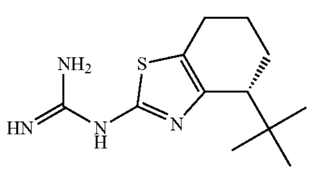 | N-(4-tert-butyl-4,5,6,7-tetrahydro-benzothiazole-2-yl)-guanidine | 2-tert-butyl-cyclohexanone | C12H20N4S 252.4 | 3.51 (LC-1) | 253.37/251.45 |

TABLE 3-continued

Analytical data for Examples C-01 to C-73

| Example | Structure | Name | Starting product | Empirical formula Molecular weight | $t_R$ [min] (HPLC method) | MS data m/z $[M + H]^+/[M - H]^-$ |
|---|---|---|---|---|---|---|
| C-08 | 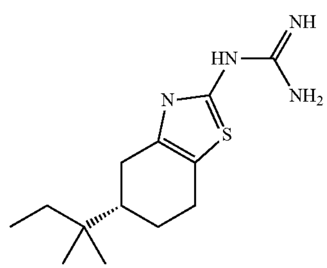 | N-[6-(1,1-dimethyl-propyl)-4,5,6,7-tetrahydro-benzothiazole-2-yl]-guanidine | 4-tert-amyl-cyclohexanone | C13H22N4S 266.4 | 2.82 (LC-1) | 267.24/265.36 |
| C-09 | 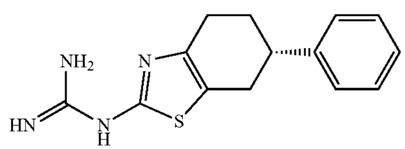 | N-(6-phenyl-4,5,6,7-tetrahydro-benzothiazole-2-yl)-guanidine | 4-phenyl-cyclohexanone | C14H16N4S 272.4 | 2.74 (LC-1) | 273.20/271.30 |
| C-10 | 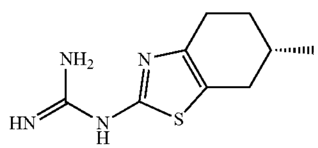 | N-(6-methyl-4,5,6,7-tetrahydro-benzothiazole-2-yl)-guanidine | 4-methyl-cyclohexanone | C9H14N4S 210.3 | 2.7 (LC-1) | 211.24/209.19 |
| C-11 | 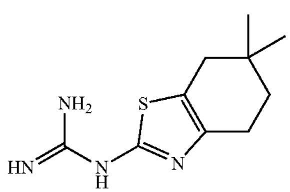 | N-(6,6-dimethyl-4,5,6,7-tetrahydro-benzothiazole-2-yl)-guanidine | 4,4-dimethyl-cyclohexanone | C10H16N4S 224.3 | 3.28 (LC-1) | 225.36/223.37 |

TABLE 3-continued

Analytical data for Examples C-01 to C-73

| Example | Structure | Name | Starting product | Empirical formula Molecular weight | $t_R$ [min] (HPLC method) | MS data m/z $[M + H]^+/[M - H]^-$ |
|---|---|---|---|---|---|---|
| C-12 | 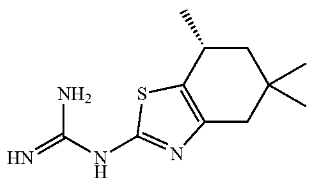 | N-(5,5,7-trimethyl-4,5,6,7-tetrahydro-benzothiazole-2-yl)-guanidine | 3,3,5-trimethyl-cyclohexanone | C11H18N4S 238.4 | 3.34 (LC-1) | 239.33/237.36 |
| C-13 | 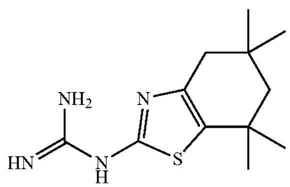 | N-(5,5,7,7-tetramethyl-4,5,6,7-tetrahydro-benzothiazole-2-yl)-guanidine | 3,3,5,5-tetramethyl-cyclohexanone | C12H20N4S 252.4 | 2.73 (LC-1) | 253.21/251.26 |
| C-14 | 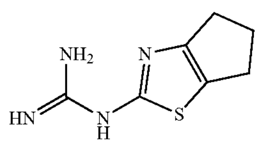 | N-(5,6-dihydro-4H-cyclopenta-thiazol-2-yl)-guanidine | cyclopentanone | C7H10N4S 182.2 | 2.83 (LC-1) | 183.31/181.32 |
| C-15 | 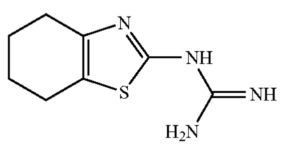 | N-(4,5,6,7-tetrahydro-benzothiazole-2-yl)-guanidine | cyclohexanone | C8H12N4S 196.3 | 2.75 (LC-1) | 197.22/195.34 |
| C-16 | 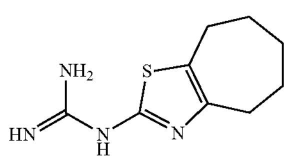 | N-(5,6,7,8-tetrahydro-4H-cycloheptathiazol-2-yl)-guanidine | cycloheptanone | C9H14N4S 210.3 | 2.89 (LC-1) | 211.25/209.26 |

TABLE 3-continued

Analytical data for Examples C-01 to C-73

| Example | Structure | Name | Starting product | Empirical formula Molecular weight | $t_R$ [min] (HPLC method) | MS data m/z $[M + H]^+/[M - H]^-$ |
|---|---|---|---|---|---|---|
| C-17 | 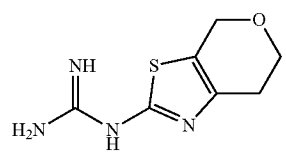 | N-(6,7-dihydro-4H-pyrano[4,3-d]thiazol-2-yl)-guanidine | tetrahydropyran-4-one | C7H10N4OS 198.2 | 1.76 (LC-1) | 199.27/197.31 |
| C-18 | 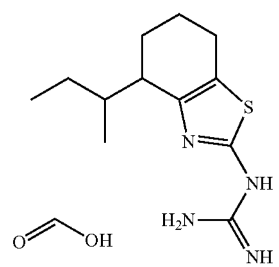 | N-(4-sec-butyl-4,5,6,7-tetrahydrobenzothiazole-2-yl)-guanidine formate | 2-sec-butylcyclohexanone | C13H22N4O2S 298.4 | 3.09 (LC-1) | 253.28/251.36 |
| C-19 | 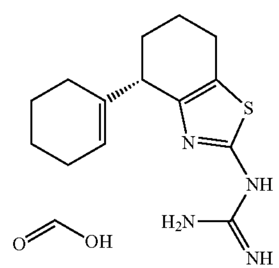 | N-(4-cyclohex-1-enyl-4,5,6,7-tetrahydrobenzothiazole-2-yl)guanidine formate | 2-(1-cyclohexenyl)cyclohexanone | C15H22N4O2S 322.4 | 3.13 (LC-1) | 277.25/275.39 |

TABLE 3-continued

Analytical data for Examples C-01 to C-73

| Example | Structure | Name | Starting product | Empirical formula Molecular weight | $t_R$ [min] (HPLC method) | MS data m/z $[M + H]^+/[M - H]^-$ |
|---|---|---|---|---|---|---|
| C-20 | 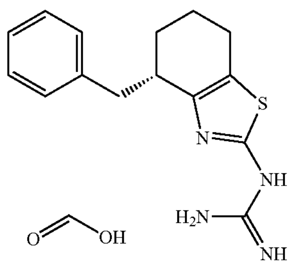 | N-(4-benzyl-4,5,6,7-tetrahydro-benzothiazole-2-yl)guanidine formate | 2-benzyl-cyclohexanone | C16H20N4O2S 332.4 | 3.09 (LC-1) | 287.25/285.27 |
| C-21 | 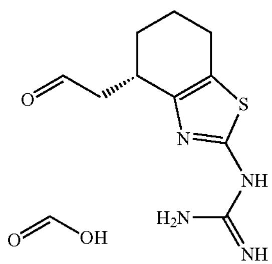 | N-(4-allyl-4,5,6,7-tetrahydro-benzothiazole-2-yl)-guanidine formate | 2-allyl-cyclohexanone | C12H18N4O2S 282.3 | 2.99 (LC-1) | 237.26/235.71 |
| C-22 | 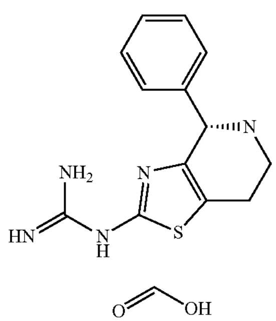 | N-(4-phenyl-4,5,6,7-tetrahydro-benzothiazole-2-yl)-guanidine formate | 2-phenyl-cyclohexanone | C15H18N4O2S 318.4 | 3.05 (LC-1) | 273.66 |

TABLE 3-continued

Analytical data for Examples C-01 to C-73

| Example | Structure | Name | Starting product | Empirical formula Molecular weight | $t_R$ [min] (HPLC method) | MS data m/z [M + H]⁺/[M − H]⁻ |
|---|---|---|---|---|---|---|
| C-23 | 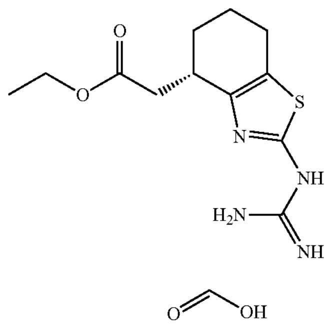 | (2-guanidino-4,5,6,7-tetrahydro-benzothiazole-4-yl)-acetic acid ethyl ester formate | ethyl(2-oxo-cyclohexyl)-acetate | C13H20N4O4S 328.4 | 1.54 (LC-2) | 283.08 |
| C-24 | 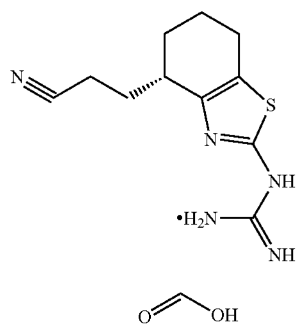 | N-[4-(2-cyano-ethyl)-4,5,6,7-tetrahydro-benzothiazole-2-yl]-guanidine formate | 2-oxo-1-cyclohexane-propionitrile | C12H17N5O2S 295.3 | 2.81 (LC-1) | 250.08 |
| C-25 | 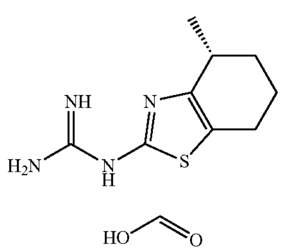 | N-(4-methyl-4,5,6,7-tetrahydro-benzothiazole-2-yl)-guanidine formate | 2-methyl-cyclohexanone | C10H16N4O2S 256.3 | 2.87 (LC-1) | 211.33 |

TABLE 3-continued

Analytical data for Examples C-01 to C-73

| Example | Structure | Name | Starting product | Empirical formula Molecular weight | $t_R$ [min] (HPLC method) | MS data m/z $[M + H]^+/[M - H]^-$ |
|---|---|---|---|---|---|---|
| C-26 | 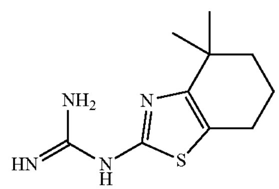 | N-(4,4-dimethyl-4,5,6,7-tetrahydro-benzothiazole-2-yl)-guanidine | 2,2-dimethyl-cyclohexanone | C10H16N4S 224.3 | 2.95 (LC-1) | 225.92 |
| C-27 | 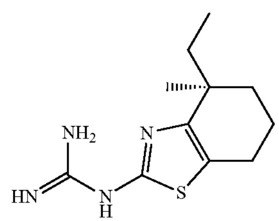 | N-(4-ethyl-4-methyl-4,5,6,7-tetrahydro-benzothiazole-2-yl)-guanidine | 2-ethyl-2-methyl-cyclohexanone | C11H18N4S 238.3 | 2.99 (LC-1) | 239.7 |
| C-28 | 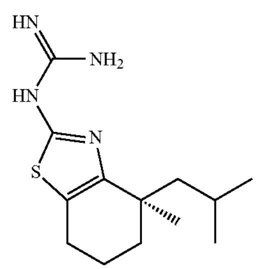 | N-(4-isobutyl-4-methyl-4,5,6,7-tetrahydro-benzothiazole-2-yl)-guanidine | 2-isobutyl-2-methyl-cyclohexanone | C13H22N4S 266.4 | 3.11 (LC-1) | 267 |

TABLE 3-continued

Analytical data for Examples C-01 to C-73

| Example | Structure | Name | Starting product | Empirical formula Molecular weight | $t_R$ [min] (HPLC method) | MS data m/z $[M + H]^+/[M - H]^-$ |
|---|---|---|---|---|---|---|
| C-29 | 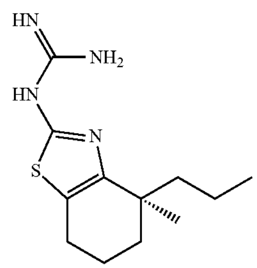 | N-(4-methyl-4-propyl-4,5,6,7-tetrahydro-benzothiazole-2-yl)-guanidine | 2-methyl-2-propyl-cyclohexanone | C12H20N4S 252.4 | 3.07 (LC-1) | 253.67 |
| C-30 | 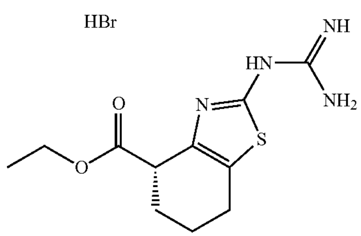 | 2-guanidino-4,5,6,7-tetrahydro-benzothiazol-4-carboxylic acid ethyl ester hydrobromide | 2-oxo-cyclohexane carboxylic acid ethyl ester | C11H17BrN4O2S 349.2 | 1.54 (LC-2) | 269.01/267.22 |
| C-31 | 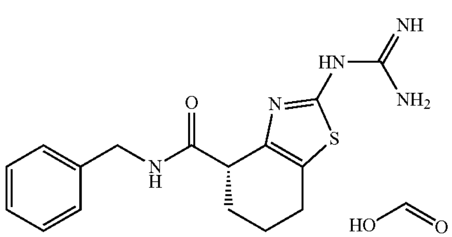 | 2-guanidino-4,5,6,7-tetrahydro-benzothiazole-4-carboxylic acid benzylamide formate | 2-guanidino-4,5,6,7-tetrahydro-benzothiazole-4-carboxylic acid | C17H21N5O3S 375.4 | 1.45 (LC-2) | 330.26/328.16 |

TABLE 3-continued

Analytical data for Examples C-01 to C-73

| Example | Structure | Name | Starting product | Empirical formula Molecular weight | $t_R$ [min] (HPLC method) | MS data m/z $[M + H]^+ / [M - H]^-$ |
|---|---|---|---|---|---|---|
| C-32 | 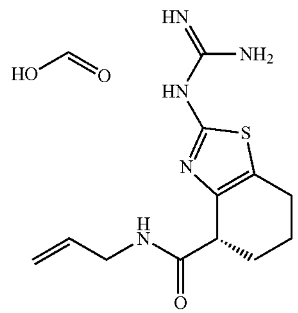 | 2-guanidino-4,5,6,7-tetrahydro-benzothiazole-4-carboxylic acid allyl amide formate | 2-guanidino-4,5,6,7-tetrahydro-benzothiazole-4-carboxylic acid | C13H19N5O3S 325.4 | 1.18 (LC-2) | 280.18/278.18 |
| C-33 | 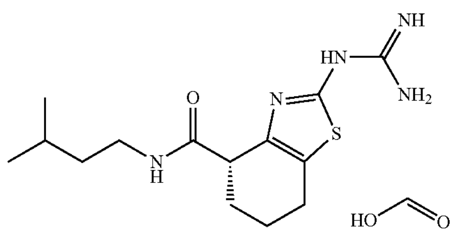 | 2-guanidino-4,5,6,7-tetrahydro-benzothiazole-4-carboxylic acid-(3-methyl-butyl)-amide formate | 2-guanadino-4,5,6,7-tetrahydro-benzothiazole-4-carboxylic acid | C15H25N5O3S 355.5 | 1.43 (LC-2) | 310.27/308.23 |
| C-34 | 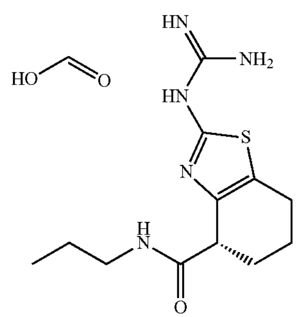 | 2-guanidino-4,5,6,7-tetrahydro-benzo-thiazol-4-carboxylic acid propylamide formate | 2-guanidino-4,5,6,7-tetrahydro-benzothiazole-4-carboxylic acid | C13H21N5O3S 327.4 | 1.25 (LC-2) | 282.19/280.21 |

TABLE 3-continued

Analytical data for Examples C-01 to C-73

| Example | Structure | Name | Starting product | Empirical formula Molecular weight | $t_R$ [min] (HPLC method) | MS data m/z [M + H]+/[M − H]− |
|---|---|---|---|---|---|---|
| C-35 | 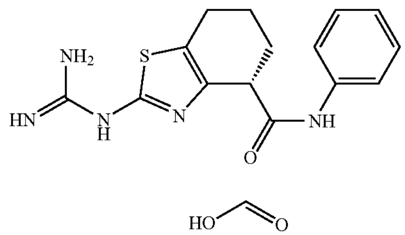 | 2-guanidino-4,5,6,7-tetrahydro-benzothiazole-4-carboxylic acid phenylamide formate | 2-guanidino-4,5,6,7-tetrahydro-benzothiazole-4-carboxylic acid | C16H19N5O3S 361.4 | 1.44 (LC-2) | 316.19/314.15 |
| C-36 | 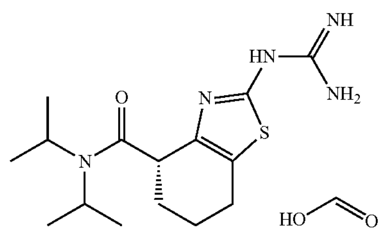 | 2-guanidino-4,5,6,7-tetrahydro-benzothiazole-4-caboxylic acid diisopropylamide formate | 2-guanidino-4,5,6,7-tetrahydro-benzothiazole-4-carboxylic acid | C16H27N5O3S 369.488 | 1.53 (LC-2) | 324.15/n.a |
| C-37 | 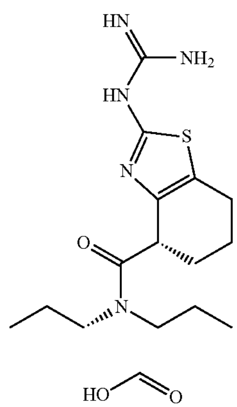 | 2-guanidino-4,5,6,7-tetrahydro-benzothiazole-4-carboxylic acid-dipropylamide formate | 2-guanidino-4,5,6,7-tetrahydro-benzothiazole-4-carboxylic acid | C16H27N5O3S 369.5 | 1.53 (LC-2) | 324.28/322.24 |

TABLE 3-continued

Analytical data for Examples C-01 to C-73

| Example | Structure | Name | Starting product | Empirical formula Molecular weight | $t_R$ [min] (HPLC method) | MS data m/z [M + H]+/[M − H]− |
|---|---|---|---|---|---|---|
| C-38 | 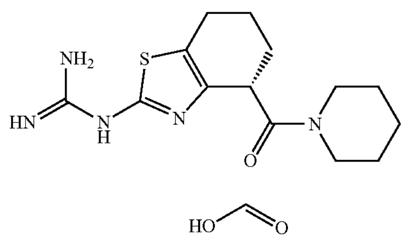 | N-[4-(piperidin-1-carbonyl)-4,5,6,7-tetrahydro-benzothiazol-2-yl]guanidine formate | 2-guanidino-4,5,6,7-tetrahydro-benzothiazole-4-carboxylic acid | C15H23N5O3S 353.4 | 1.37 (LC-2) | 308.29/306.26 |
| C-39 | 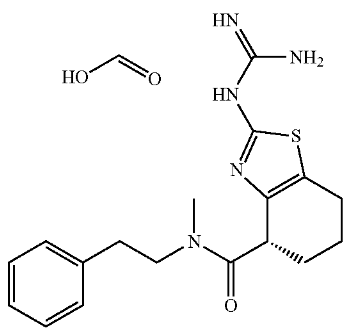 | 2-guanidino-4,5,6,7-tetrahydro-benzothiazole-4-carboxylic acid-methylphenethyl-amide formate | 2-guanidino-4,5,6,7-tetrahydro-benzothiazole-4-carboxylic acid | C19H25N5O3S 403.5 | 1.55 (LC-2) | 358.22/356.25 |
| C-40 | 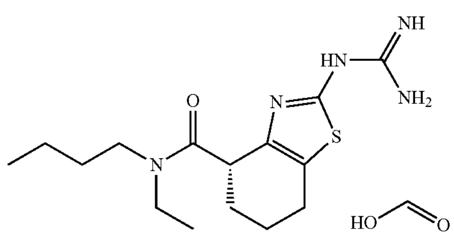 | 2-guanidino-4,5,6,7-tetrahydro-benzothiazole-4-caboxylic acid-butyl-ethyl-amide formate | 2-guanidino-4,5,6,7-tetrahydro-benzothiazole-4-carboxylic acid | C16H27N5O3S 369.5 | 1.51 (LC-2) | 324.28/322.24 |

TABLE 3-continued

Analytical data for Examples C-01 to C-73

| Example | Structure | Name | Starting product | Empirical formula Molecular weight | $t_R$ [min] (HPLC method) | MS data m/z [M + H]+/[M − H]− |
|---|---|---|---|---|---|---|
| C-41 | 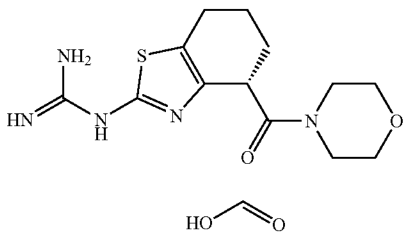 | N-[4-(morpholine-4-carbonyl)-4,5,6,7-tetrahydro-benzothiazol-2-yl-guanidine formate | 2-guanidino-4,5,6,7-tetrahydro-benzothiazole-4-carboxylic acid | C14H21N5O4S 355.4 | 1.21 (LC-2) | 310.20/308.23 |
| C-42 | 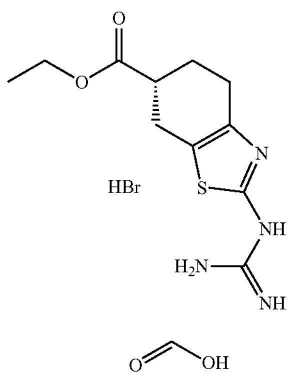 | 2-guanidino-4,5,6,7-tetrahydro-benzo-thiazol-6-carboxylic acid-ethyl ester hydrobromide | 4-oxo-cyclohexane carboxylic acid ethyl ester | C11H17BrN4O2S 349.2 | 2.76 (LC-1) | 270.59/266.22 |
| C-43 | 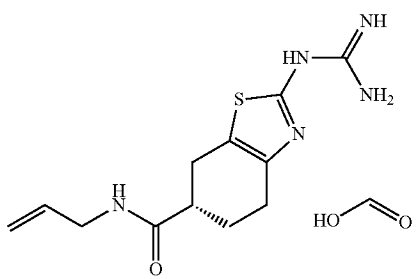 | 2-guanidino-4,5,6,7-tetrahydro-benzothiazole-6-carboxylic acid allyl amide formate | 2-guanidino-4,5,6,7-tetrahydro-benzothiazole-6-carboxylic acid | C13H19N5O3S 325.4 | 1.2 (LC-2) | 280.15/278.18 |

TABLE 3-continued

Analytical data for Examples C-01 to C-73

| Example | Structure | Name | Starting product | Empirical formula Molecular weight | $t_R$ [min] (HPLC method) | MS data m/z $[M + H]^+/[M - H]^-$ |
|---|---|---|---|---|---|---|
| C-44 | 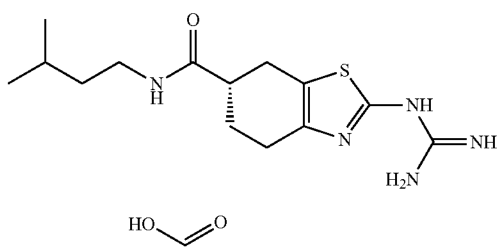 | 2-guanidino-4,5,6,7-tetrahydro-benzothiazole-6-caboxylic acid-(3-methyl-butyl)-amide formiate | 2-guanidino-4,5,6,7-tetrahydro-benzothiazole-6-carboxylic acid | C15H25N5O3S 355.5 | 1.46 (LC-2) | 310.33/308.29 |
| C-45 | 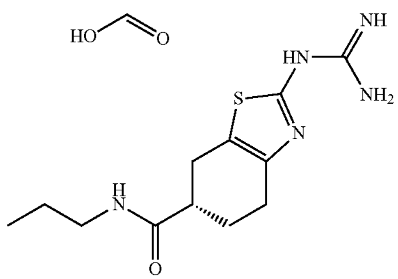 | 2-guanidino-4,5,6,7-tetrahydro-benzothiazole-6-carboxylic acid-propylamide formiate | 2-guanidino-4,5,6,7-tetrahydro-benzothiazole-6-carboxylic acid | C13H21N5O3S 327.4 | 1.27 (LC-2) | 282.12 |
| C-46 | 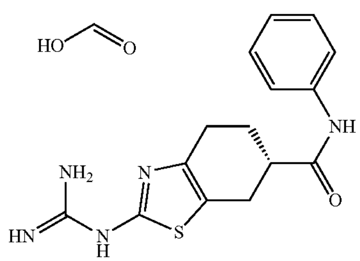 | 2-guanidino-4,5,6,7-tetrahydro-benzothiazol-6-carboxylic acid-phenylamide formiate | 2-guanidino-4,5,6,7-tetrahydro-benzothiazole-6-carboxylic acid | C16H19N5O3S 361.4 | 1.46 (LC-2) | 265.63/263.24 |

TABLE 3-continued

Analytical data for Examples C-01 to C-73

| Example | Structure | Name | Starting product | Empirical formula Molecular weight | $t_R$ [min] (HPLC method) | MS data m/z [M + H]+/[M − H]− |
|---|---|---|---|---|---|---|
| C-47 | 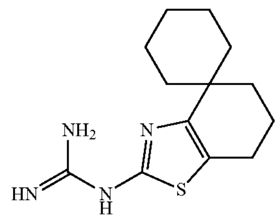 | N-(tetrahydro-benzothiazole-2-yl-4-spiro-cyclohexane)-guanidine | spiro[5.5]undec-an-1-one | C13H20N4S 264.4 | 1.69 (LC-2) | 265.63/263.24 |
| C-48 | 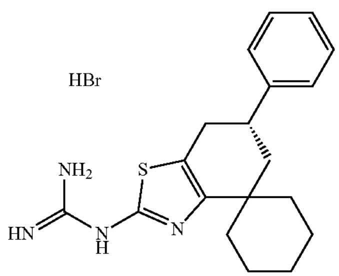 | N-(6-phenyl-4,5,6,7-tetra-hydro-benzo-thiazol-2-yl-4-spiro-cyclohexane)-guanidine hydrobromide | 4-phenyl-spiro[5.5]undec-an-1-one | C19H25BrN4S 421.4 | 1.85 (LC-2) | 341.54/339.24 |
| C-49 | 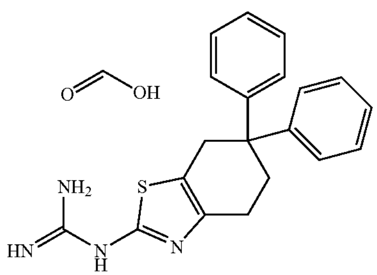 | N-(6,6-diphenyl-4,5,6,7-tetrahydro-benzothiazole-2-yl)-guanidine formate | 4,4-diphenyl-cyclohexanone | C21H22N4O2S 394.5 | 3.15 (LC-1) | 349.24/347.44 |

TABLE 3-continued

Analytical data for Examples C-01 to C-73

| Example | Structure | Name | Starting product | Empirical formula Molecular weight | $t_R$ [min] (HPLC method) | MS data m/z [M + H]⁺/[M − H]⁻ |
|---|---|---|---|---|---|---|
| C-50 | (structure: 2-guanidino-6-phenyl-4,5,6,7-tetrahydrobenzothiazole-6-carboxylic acid ethyl ester formate) | 2-guanidino-6-phenyl-4,5,6,7-tetrahydro-benzothiazol-6-carboxylic acid-ethyl ester formate | 4-oxo-1-phenyl-cyclohexane carboxylic acid ethyl ester | C18H22N4O2S 390.5 | 1.75 (LC-2) | 345.36 |
| C-51 | (structure: N-(6-cyano-6-phenyl-4,5,6,7-tetrahydro-benzothiazol-2-yl)-guanidine hydrobromide) | N-(6-cyano-6-phenyl-4,5,6,7-tetrahydro-benzothiazol-2-yl)-guanidine hydrobromide | 4-cyano-4-phenylcyclohexanone | C15H16BrN5S 378.3 | 2.92 (LC-1) | 298.1/295.97 |
| C-52 | (structure: N-[6-(4-methoxyphenyl)-4,5,6,7-tetrahydro-benzothiazol-2-yl]-guanidine hydrobromide) | N-[6-(4-methoxyphenyl)-4,5,6,7-tetrahydro-benzothiazol-2-yl]-guanidine hydrobromide | 4-(4-methoxyphenyl)cyclohexanone | C15H19BrN4OS 383.3 | 3.0 (LC-1) | 303.25/301.26 |

TABLE 3-continued

Analytical data for Examples C-01 to C-73

| Example | Structure | Name | Starting product | Empirical formula Molecular weight | $t_R$ [min] (HPLC method) | MS data m/z $[M + H]^+/[M - H]^-$ |
|---|---|---|---|---|---|---|
| C-53 | HBr | N-[6-(4-benzyloxyphenyl)-4,5,6,7-tetrahydro-benzothiazole-2-yl]-guanidine hydrobromide | 4-(4-benzyloxyphenyl)cyclohexanone | C21H23BrN4OS 459.4 | 3.24 (LC-1) | 379.26 |
| C-54 | HBr | N-[6-(4-fluorophenyl)-4,5,6,7-tetrahydro-benzothiazol-2-yl]-guanidine hydrobromide | 4-(4-fluorophenyl)-cyclohexanone | C14H16BrFN4S 371.3 | 3.04 (LC-2) | 291.26/289.33 |
| C-55 | 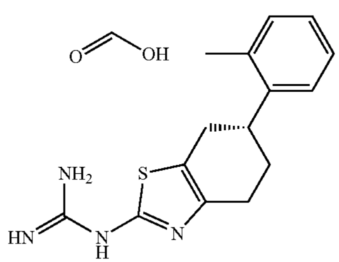 | N-(6-o-tolyl-4,5,6,7-tetrahydro-benzo-thiazol-2-yl)-guanidine formate | 4-o-tolyl-cyclohexanone | C16H20N4O2S 332.4 | 3.42 (LC-2) | 286.25 |

TABLE 3-continued

Analytical data for Examples C-01 to C-73

| Example | Structure | Name | Starting product | Empirical formula Molecular weight | $t_R$ [min] (HPLC method) | MS data m/z [M + H]+/[M − H]− |
|---|---|---|---|---|---|---|
| C-56 | 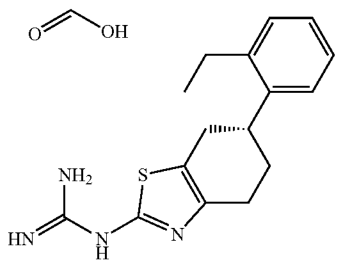 | N-[6-(2-ethyl-phenyl)-4,5,6,7-tetrahydro-benzothiazol-2-yl]-guanidine formate | 4-(2-ethyl-phenyl)-cyclo-hexanone | C17H22N4O2S 346.4 | 3.13 (LC-2) | 301.33/299.4 |
| C-57 | 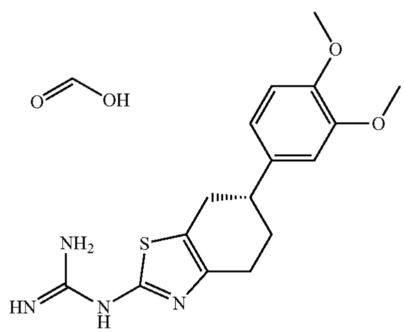 | N-[6-(3,4-dimethoxyphenyl)-4,5,6,7-tetrahydro-benzothiazole-2-yl]-guanidine formate | 4-(3,4-dimethoxyphenyl)cyclohexanone | C17H22N4O4S 378.4 | 3.44 (LC-2) | 333.2 |
| C-58 | 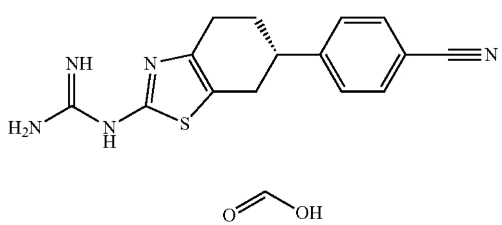 | N-[6-(4-cyanophenyl)-4,5,6,7-tetrahydro-benzothiazol-2-yl]-guanidine formate | 4-(4-oxocyclohexyl)-benzonitrile | C16H17N5O2S 343.4 | 1.59 (LC-2) | 298.17/296.26 |

TABLE 3-continued

Analytical data for Examples C-01 to C-73

| Example | Structure | Name | Starting product | Empirical formula Molecular weight | $t_R$ [min] (HPLC method) | MS data m/z $[M+H]^+/[M-H]^-$ |
|---|---|---|---|---|---|---|
| C-59 | 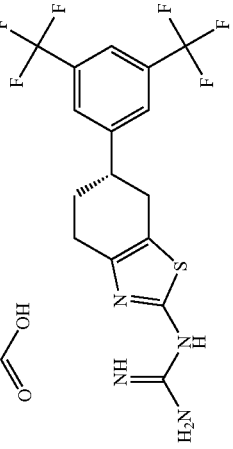 | N-[6-(3,5-bis-trifluoromethyl-phenyl)-4,5,6,7-tetrahydro-benzo-thiazol-2-yl)-guanidine formate | 4-(3,5-bis-trifluoromethyl-phenyl)-cyclohexanone | C17H16F6N4O2S 454.4 | 1.88 (LC-2) | 408.99/407.15 |
| C-60 | 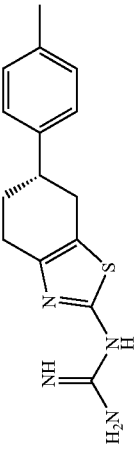 | N-(6-p-tolyl-4,5,6,7-tetrahydro-benzo-thiazol-2-yl)-guanidine formate | 4-p-tolyl-cyclohexanone | C16H20N4O2S 332.4 | 1.68 (LC-2) | 287.15 |
| C-61 | 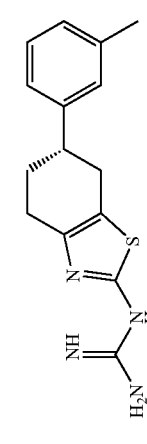 | N-(6-m-tolyl-4,5,6,7-tetrahydro-benzothiazole-2-yl)-guanidine formate | 3-m-tolyl-cyclohexanone | C16H20N4O2S 332.4 | 1.73 (LC-2) | 287.22 |
| C-62 | 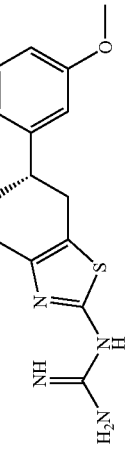 | N-[6-(3-methoxy-phenyl)-4,5,6,7-tetrahydro-benzo-thiazol-2-yl]-guanidine formate | 4-(3-methoxy-phenyl)-cyclohexanone | C16H20N4O3S 348.4 | 1.73 (LC-2) | 303.2/301.35 |

TABLE 3-continued

Analytical data for Examples C-01 to C-73

| Example | Structure | Name | Starting product | Empirical formula Molecular weight | $t_R$ [min] (HPLC method) | MS data m/z $[M + H]^+/[M - H]^-$ |
|---|---|---|---|---|---|---|
| C-63 | 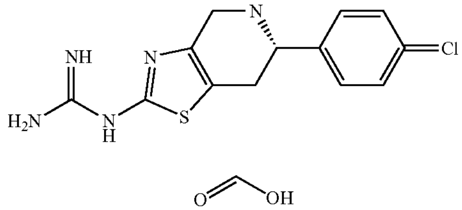 | N-[6-(4-chlorophenyl)-4,5,6,7-tetrahydro-benzothiazol-2-yl]-guanidine formate | 4-(4-chlorophenyl)-cyclohexanone | C15H17ClN4O2S 352.8 | 1.85 (LC-2) | 307.15/305.13 |
| C-64 | 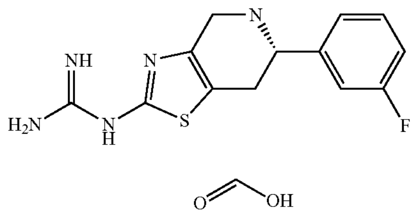 | N-[6-(3-fluorophenyl)-4,5,6,7-tetrahydro-benzo-thiazol-2-yl]-guanidine formate | 4-(3-fluorophenyl)-cyclohexanone | C15H17FN4O2S 336.4 | 1.55 (LC-2) | 290.91/289.25 |
| C-65 | 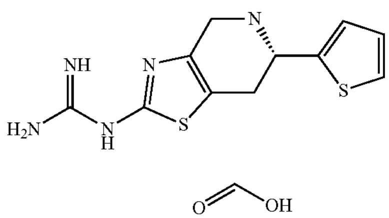 | N-(6-thiophene-2-yl-4,5,6,7-tetrahydro-benzothiazole-2-yl)-guanidine formate | 4-thiophene-2-yl-cyclohexanone | C13H16N4O2S2 324.4 | 1.61 (LC-2) | 279.13/277.72 |
| C-66 | 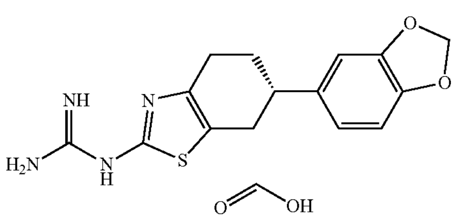 | N-(6-benzo[1,3]-dioxol-5-yl-4-4,5,6,7-tetrahydro-benzothiazol-2-yl)-guanidine formate | 4-benzo[1,3]dioxol-5-yl-cyclohexanone | C16H18N4O4S 362.4 | 1.66 (LC-2) | 317.02 |

TABLE 3-continued

Analytical data for Examples C-01 to C-73

| Example | Structure | Name | Starting product | Empirical formula Molecular weight | $t_R$ [min] (HPLC method) | MS data m/z [M + H]$^+$/[M − H]$^-$ |
|---|---|---|---|---|---|---|
| C-67 | 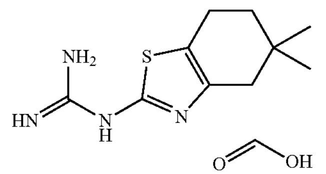 | N-(5,5-dimethyl-4,5,6,7-tetrahydro-benzo-thiazol-2-yl)-guanidine formate | 3,3-dimethyl-cyclohexanone | C11H18N4O2S 270.3 | 2.92 (LC-2) | 225.34 |
| C-68 | 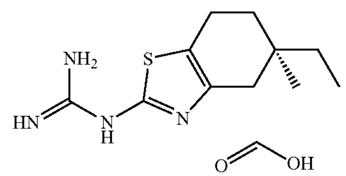 | N-(5-ethyl-5-methyl-4,5,6,7-tetrahydro-benzo-thiazol-2-yl]-guanidine formate | 3-ethyl-3-methyl-cyclohexanone | C12H20N4O2S 284.4 | 2.97 (LC-1) | 239.25/237.2 |
| C-69 | 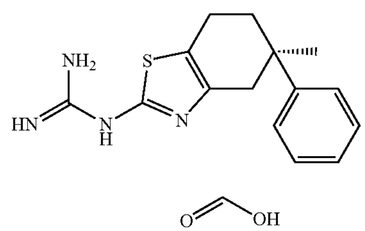 | N-(5-methyl-5-phenyl-4,5,6,7-tetrahydro-benzothiazole-2-yl)-guanidine formate | 3-methyl-3-phenyl-cyclohexanone | C16H20N4O2S 332.4 | 3.01 (LC-2) | 286.45 |
| C-70 | 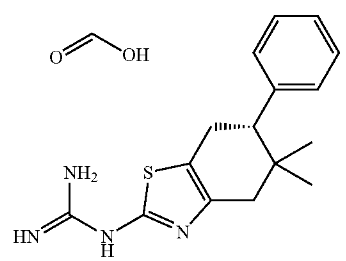 | N-(5,5-dimethyl-6-phenyl-4,5,6,7-tetrahydro-benzo-thiazol-2-yl]-guanidine formate | 3,3-dimethyl-4-phenyl-cyclohexanone | C17H22N4O2S 346.4 | 1.85 (LC-2) | 301.33/299.35 |

TABLE 3-continued

Analytical data for Examples C-01 to C-73

| Example | Structure | Name | Starting product | Empirical formula Molecular weight | $t_R$ [min] (HPLC method) | MS data m/z $[M + H]^+/[M - H]^-$ |
|---|---|---|---|---|---|---|
| C-71 | 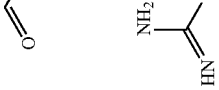 | N-(7-methyl-4,5,6,7-tetrahydro-benzo-thiazol-2-yl)-guanidine formate | 2-bromo-3-methyl-cyclohexanone | C10H16N4O2S 256.3 | 2.84 (LC-1) | 211.24 |
| C-72 | 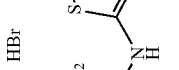 | N-(5-phenyl-5,6,7,8-tetrahydro-4H-cycloheptathiazol-2-yl]-guanidine hydrobromide | 2-bromo-6-phenyl-cycloheptanone | C15H19BrN4S 367.3 | 3.05 (LC-2) | 287.34/285.42 |
| C-73 | 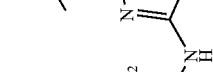 | N-(4-tert-butyl-6-phenyl-4,5,6,7-tetrahydro-benzothiazole-2-yl)-guanidine | 2-tert-butyl-6-chloro-4-phenyl-cyclohexanone | C18H24N4S 328.5 | 1.85 (LC-2) | 329.25/327.27 |

TABLE 4

Analytical data for Examples N-01 to N-33

| Example | Structure | Name | R'-reagent | Empirical formula Molecular weight | | |
|---|---|---|---|---|---|---|
| N-01 | 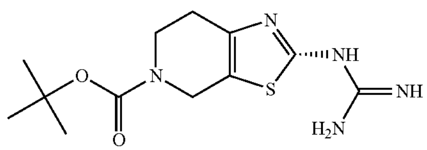 | 2-guanidino-6,7-dihydro-4H-thiazolo[5,4-c]pyridine-5-carboxylic acid tert-butyl ester | | C12H19N5O2S 297.4 | 2.88 (LC-1) | 298.22/296.29 |
| N-02 | 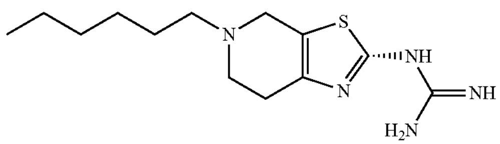 | N-(5-hexyl-4,5,6,7-tetrahydro-thiazolo[5,4-c]pyridine-2-yl)-guanidine | 1-bromohexane | C13H23N5S 281.4 | 0.94 (LC-1) | 282.18/280.33 |
| N-03 | 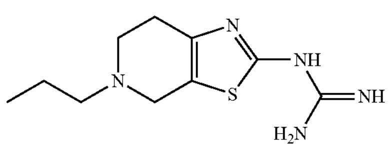 | N-(5-propyl-4,5,6,7-tetrahydro-thiazolo[5,4-c]pyridine-2-yl)-guanidine | 1-bromopropane | C10H17N5S 239.3 | 0.85 (LC-1) | 240.18/283.31 |
| N-04 | 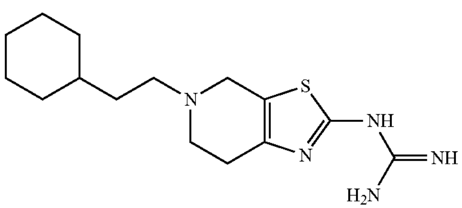 | N-[5-(2-cyclohexyl-ethyl)-4,5,6,7-tetrahydro-thiazolo[5,4-c]pyridine-2-yl)-guanidine | (2-bromethyl)-cyclohexane | C15H25N5S 307.5 | 0.95 (LC-1) | 308.28/306.42 |

TABLE 4-continued

Analytical data for Examples N-01 to N-33

| Example | Structure | Name | R'-reagent | Empirical formula Molecular weight | | |
|---|---|---|---|---|---|---|
| N-05 | 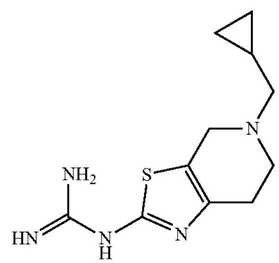 | N-(5-cyclo-propylmethyl-4,5,6,7-tetrahydro-thiazolo[5,4-c]pyridine-2-yl)-guanidine | bromomethyl-cyclopropane | C11H17N5S 251.3 | 0.86 (LC-1) | 252.16/250.25 |
| N-06 | 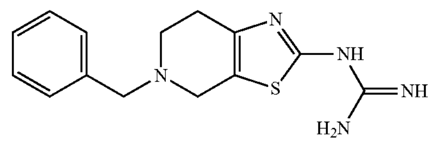 | N-(5-benzyl-4,5,6,7-tetrahydro-thiazolo[5,4-c]pyridine-2-yl)-guanidine | benzyl bromide | C14H17N5S 287.4 | 2.67 (LC-1) | 288.22/286.16 |
| N-07 | 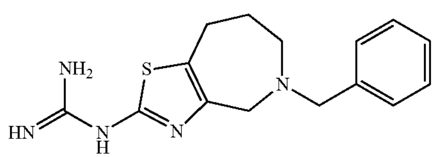 | N-(5-benzyl-5,6,7,8-tetrahydro-4H-thiazolo[4,5-c]azepine-2-yl)-guanidine | benzyl bromide | C15H19N5S 301.4 | 0.9 (LC-1) | 302.12/300.02 |
| N-08 | 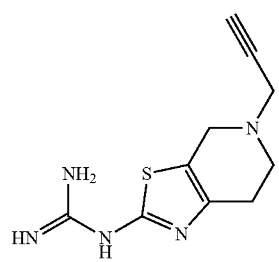 | N-(5-prop-2-ynyl-4,5,6,7-tetra-hydro-thiazolo[5,4-c]pyridine-2-yl)-guanidine | propargyl bromide | C10H13N5S 235.3 | 0.83 (LC-1) | 236.16/234.25 |

TABLE 4-continued

Analytical data for Examples N-01 to N-33

| Example | Structure | Name | R'-reagent | Empirical formula Molecular weight | | |
|---|---|---|---|---|---|---|
| N-09 | 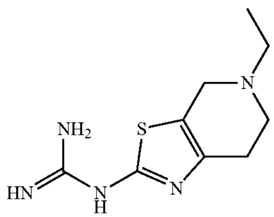 | N-(5-ethyl-4,5,6,7-tetrahydro-thiazolo[5,4-c]pyridine-2-yl)-guanidine | 1-bromomethane | C9H15N5S 225.3 | 0.86 (LC-1) | 226.20/227.07 |
| N-10 | 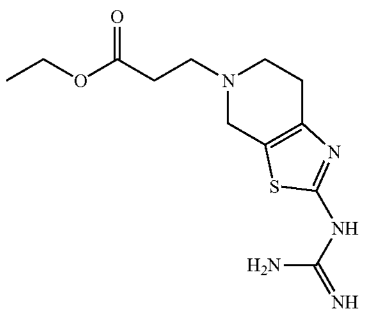 | 3-(2-guanidino-6,7-dihydro-4H-thiazolo[5,4-c]pyridine-5-yl)-propionic acid ethyl ester | ethyl-3-bromopropionate | C12H19N5O2S 297.4 | 0.84 (LC-1) | 298.18/296.35 |
| N-11 | 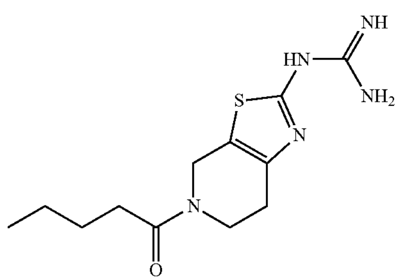 | N-(5-pentanoyl-4,5,6,7-tetrahydro-thiazolo[5,4-c]pyridine-2-yl)-guanidine | pentanoyl chloride | C12H19N5OS 281.4 | 2.46 (LC-1) | 282.21/280.32 |

TABLE 4-continued

Analytical data for Examples N-01 to N-33

| Example | Structure | Name | R¹-reagent | Empirical formula Molecular weight | |
|---|---|---|---|---|---|
| N-12 | 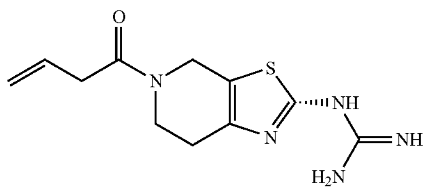 | N-(5-but-3-enoyl-4,5,6,7-tetra-hydro-thiazolo[5,4-c]pyridine-2-yl)-guanidine | vinylacetic acid | C11H15N5OS 265.3 | 0.82 (LC-1) 266.21/264.29 |
| N-13 | 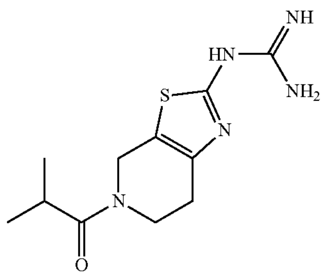 | N-(5-isobutyryl-4,5,6,7-tetrahydro-thiazolo[5,4-c]pyridine-2-yl)-guanidine | isobutyryl chloride | C11H17N5OS 267.3 | 0.81 (LC-1) 268.20/266.32 |
| N-14 | 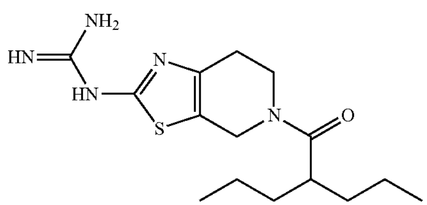 | N-[5-(2-propyl-pentanoyl)-4,5,6,7-tetrahydro-thiazolo[5,4-c]pyridine-2-yl)-guanidine | 2-propyl-pentanoyl-chloride | C15H25N5OS 323.5 | 2.56 (LC-1) 324.28/322.31 |
| N-15 | 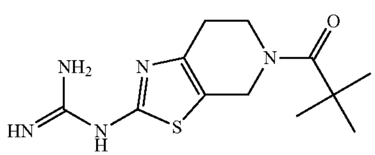 | N-[5-(2,2-dimethyl-propionyl)-4,5,6,7-tetrahydro-thiazolo[5,4-c]pyridine-2-yl)-guanidine | 2,2-dimethyl-propionyl chloride | C12H19N5OS 281.4 | 2.47 (LC-1) 282.18/280.31 |

TABLE 4-continued

Analytical data for Examples N-01 to N-33

| Example | Structure | Name | R'-reagent | Empirical formula Molecular weight | | |
|---|---|---|---|---|---|---|
| N-16 | 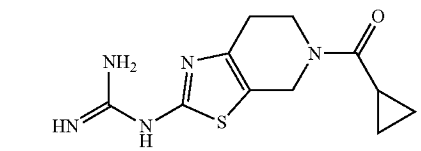 | N-(5-cyclopropane-carbonyl-4,5,6,7-tetrahydro-thiazolo[5,4-c]pyridine-2-yl)-guanidine | Cyclopropane-carbonyl chloride | C11H15N5OS 265.3 | 0.82 (LC-1) | 266.19/264.24 |
| N-17 | 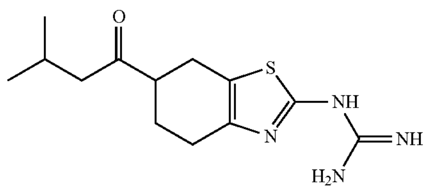 | N-[5-(3-methyl-butyryl)-4,5,6,7-tetrahydro-thiazolo[5,4-c]pyridine-2-yl)-guanidine | 3-methyl-butyryl-chloride | C12H19N5OS 281.4 | 0.83 (LC-1) | 282.25/280.33 |
| N-18 | 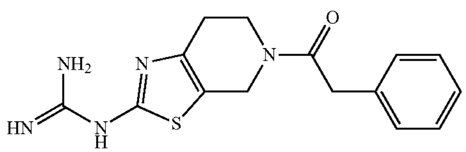 | N-[5-(2-phenlacetyl)-4,5,6,7-tetrahydro-thiazolo[5,4-c]pyridine-2-yl)-guanidine | phenylacetyl chloride | C15H17N5OS 315.4 | 2.49 (LC-1) | 316.15/314.25 |
| N-19 | 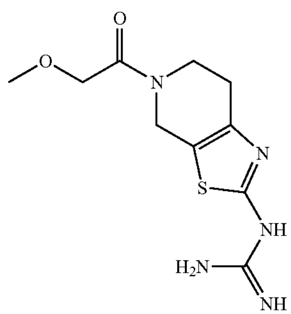 | N-[5-(2-methoxy-acetyl)-4,5,6,7-tetrahydro-thiazolo[5,4-c]pyridine-2-yl]-guanidine | methoxyacetic acid | C10H15N5O2S 269.3 | 0.83 (LC-1) | 270.20/268.34 |

TABLE 4-continued

Analytical data for Examples N-01 to N-33

| Example | Structure | Name | R'-reagent | Empirical formula Molecular weight | | |
|---|---|---|---|---|---|---|
| N-20 | 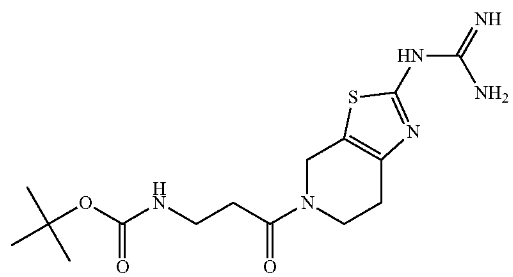 | [3-(2-guanidino-6,7-dihydro-4H-thiazolo[5,4-c]pyridine-5-yl)-3-oxopropyl]carbamic acid tert-butylester | boc-beta-alanine | C15H24N6O3S 368.5 | 0.81 (LC-1) | 369.13/367.27 |
| N-21 | 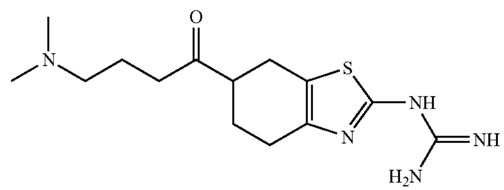 | N-[5-(4-dimethylamino-butyryl)-4,5,6,7-tetrahydro-thiazolo[5,4-c]pyridine-2-yl)-guanidine | 4-dimethylamino butanoic acid | C13H22N6OS 310.4 | 0.82 (LC-1) | 311.16/309.15 |
| N-22 | 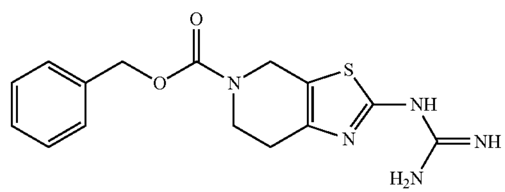 | 2-guanidino-6,7-dihydro-4H-thiazolo[5,4-c]pyridine-5-carboxylic acid benzyl ester | benzyl chloroformate | C15H17N5O2S 331.4 | 2.7 (LC-1) | 322.17/330.24 |
| N-23 | 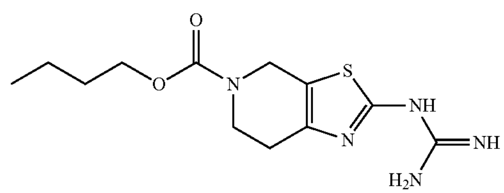 | 2-guanidino-6,7-dihydro-4H-thiazolo[5,4-c]pyridine-5-carboxylic acid butyl ester | butyl chloroformate | C12H19N5O2S 297.4 | 2.67 (LC-1) | 298.25/296.28 |

TABLE 4-continued

Analytical data for Examples N-01 to N-33

| Example | Structure | Name | R'-reagent | Empirical formula Molecular weight | | |
|---|---|---|---|---|---|---|
| N-24 | 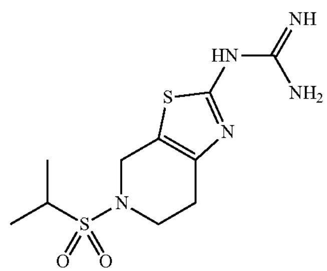 | N-[5-(propane-2-sulphonyl)-4,5,6,7-tetrahydro-thiazolo[5,4-c]pyridine-2-yl)-guanidine | 2-propanesulphonyl chloride | C10H17N5O2S2 303.4 | 0.81 (LC-1) | 304.08/302.25 |
| N-25 | 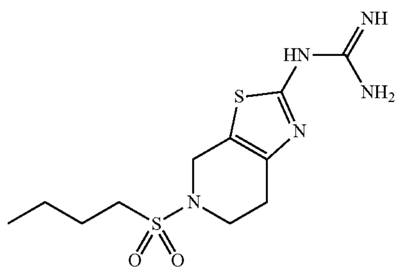 | N-[5-(butane-1-sulphonyl)-4,5,6,7-tetrahydrothiazolo[5,4-c]pyridine-2-yl)-guanidine | 1-butanesulphonyl chloride | C11H19N5O2S2 317.4 | 0.84 (LC-1) | 318.11/316.28 |
| N-26 | 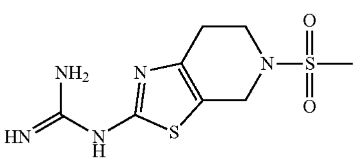 | N-(5-methanesulphonyl-4,5,6,7-tetrahydrothiazolo[5,4-c]pyridine-2-yl)-guanidine | methanesulphonyl chloride | C8H13N5O2S2 275.3 | 0.83 (LC-1) | 267.11/274.25 |
| N-27 | 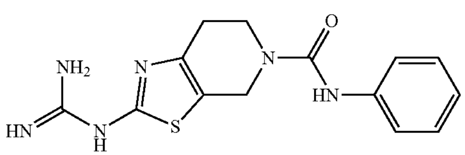 | 2-guanidino-6,7-dihydro-4H-thiazolo[5,4-c]pyridine-5-carboxylic acid phenyl amide | phenyl isocyanate | C14H16N6OS 316.4 | 2.76 (LC-1) | 317.19/315.33 |

TABLE 4-continued

Analytical data for Examples N-01 to N-33

| Example | Structure | Name | R'-reagent | Empirical formula Molecular weight | | |
|---|---|---|---|---|---|---|
| N-28 | 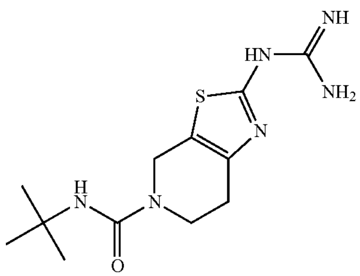 | 2-guanidino-6,7-dihydro-4H-thiazolo[5,4-c]pyridine-5-carboxylic acid tert-butyl amide | tert-butyl isocyanate | C12H20N6OS 296.4 | 2.73 (LC-1) | 297.25/295.4 |
| N-29 | 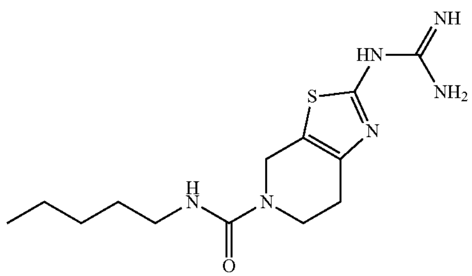 | 2-guanidino-6,7-dihydro-4H-thiazolo[5,4-c]pyridine-5-carboxylic acid pentyl amide | pentyl isocyanate | C13H22N6OS 310.4 | 2.81 (LC-1) | 311.23/309.37 |
| N-30 | 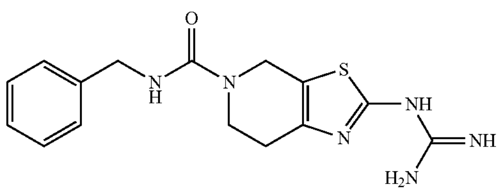 | 2-guanidino-6,7-dihydro-4H-thiazolo[5,4-c]pyridine-5-thiocarboxylic acid benzyl amide | benzylamine | C15H18N6S2 346.5 | 2.91 (LC-1) | 246.82/345.09 |

TABLE 4-continued

Analytical data for Examples N-01 to N-33

| Example | Structure | Name | R'-reagent | Empirical formula Molecular weight | | |
|---|---|---|---|---|---|---|
| N-31 | 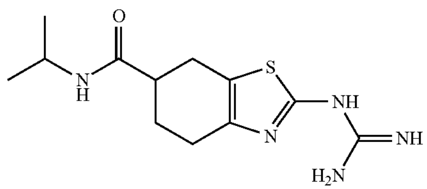 | 2-guanidino-6,7-dihydro-4H-thiazolo[5,4-c]pyridine-5-thiocarboxylic acid isopropyl amide | isopropylamine | C11H18N6S2 298.4 | 2.94 (LC-1) | 298.86/296.29 |
| N-32 | 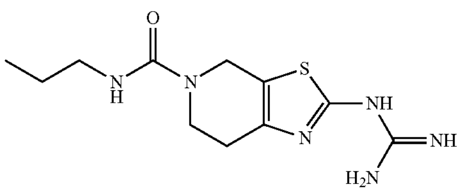 | 2-guanidino-6,7-dihydro-4H-thiazolo[5,4-c]thiocarboxylic acid propylamide | propylamine | C11H18N6S2 298.4 | 2.78 (LC-1) | 299.11/291.7 |
| N-33 | 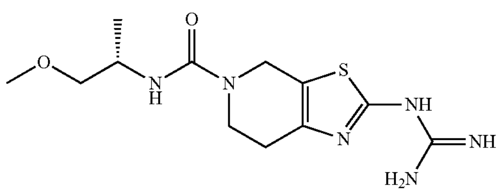 | 2-guanidino-6,7-dihydro-4H-thiazolo[5,4-c]pyridine-5-thiocarboxylic acid-(2-methoxy-1-methyl-ethyl) amide | 2-amino-1-methoxypropane | C12H20N6OS2 328.4 | 2.72 (LC-1) | 329.38/326.93 |

The invention claimed is:
1. A compound of formula I

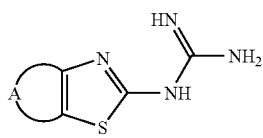

(I)

wherein A is a three to six carbon atom chain, wherein
(i) A does not comprise double bonds; and
(ii) at least one of the carbon atoms of A is substituted by one or more:
methyl, ethyl, n-propyl, isopropyl, n-butyl, isobutyl, sec-butyl, tert-butyl, 1,1-dimethylpropyl, allyl or cyclohex-1-enyl groups; or
phenyl, O-tolyl, m-tolyl, p-tolyl, 2-ethylphenyl, 3-fluorophenyl, 4-fluorophenyl, 4-chlorophenyl, 4-cyanophenyl, 4-benzyloxyphenyl, 3-methoxyphenyl, 4-methoxyphenyl, 3,4-dimethoxyphenyl, 3,4-methylenedioxyphenyl or bis-3,5-trifluoromethylphenyl groups; or
thiophene-2-yl or benzyl groups; or
cyano or cyanoethyl groups; or
pentamethylene groups linked at each end to a single carbon atom;
or a pharmaceutically acceptable salt thereof.

2. The compound according to claim 1, wherein one carbon atom of A is substituted by a phenyl group and a cyano group.

3. The compound according to claim 1, wherein the compound is
N-(5-ethyl-5-methyl-4,5,6,7-tetrahydro-benzothiazole-2-yl)-guanidine or its formate;
N-(4-tert-butyl-4,5,6,7-tetrahydro-benzothiazole-2-yl)-guanidine;
N-(6-isopropyl-4,5,6,7-tetrahydro-benzothiazole-2-yl)-guanidine;
N-(5-butyl-5,6,7,8-tetrahydro-4H-cycloheptathiazol-2-yl)-guanidine;
N-(4-ethyl-4-methyl-4,5,6,7-tetrahydro-benzothiazole-2-yl)-guanidine;
N-[6-(3,4-dimethoxyphenyl)-4,5,6,7-tetrahydro-benzothiazole-2-yl]-guanidine or its formate;
N-(5-butyl-4,5,6,7-tetrahydro-benzothiazole-2-yl)-guanidine;
N-(6-phenyl-4,5,6,7-tetrahydro-benzothiazole-2-yl)-guanidine;
N-(6-propyl-4,5,6,7-tetrahydro-benzothiazole-2-yl)-guanidine;
N-(4-cyclohex-1-enyl-4,5,6,7-tetrahydro-benzothiazole-2-yl)-guanidine or its formate;
N-(4-sec-butyl-4,5,6,7-tetrahydro-benzothiazole-2-yl)-guanidine or its formate; or
N-(4-isobutyl-4-methyl-4,5,6,7-tetrahydro-benzothiazole-2-yl)-guanidine.

4. The compound according to claim 1, wherein the compound is
N-(6-tert-butyl-4,5,6,7-tetrahydro-benzothiazole-2-yl)-guanidine;
N-[6-(1,1-dimethyl-propyl)-4,5,6,7-tetrahydro-benzothiazole-2-yl]-guanidine;
N-[6-(3-methoxy-phenyl)-4,5,6,7-tetrahydro-benzothiazole-2-yl]-guanidine or its formate;
N-(6-thiophene-2-yl-4,5,6,7-tetrahydro-benzothiazole-2-yl)-guanidine or its formate;
N-[6-(4-fluorophenyl)-4,5,6,7-tetrahydro-benzothiazole-2-yl]-guanidine or its hydrobromide;
N-(4-allyl-4,5,6,7-tetrahydro-benzothiazole-2-yl)-guanidine or its formate;
N-[6-(3-fluorophenyl)-4,5,6,7-tetrahydro-benzothiazole-2-yl]-guanidine or its formate;
N-(6-cyano-6-phenyl-4,5,6,7-tetrahydro-benzothiazole-2-yl)-guanidine or its hydrobromide;
N-(4-phenyl-4,5,6,7-tetrahydro-benzothiazole-2-yl)-guanidine or its formate; or
N-(6,6-diphenyl-4,5,6,7-tetrahydro-benzothiazole-2-yl)-guanidine or its formate.

5. The compound according to claim 1, wherein the compound is
N-[6-(4-methoxy-phenyl)-4,5,6,7-tetrahydro-benzothiazole-2-yl]-guanidine or its hydrobromide;
N-(5-phenyl-5,6,7,8-tetrahydro-4H-cycloheptathiazol-2-yl)-guanidine or its hydrobromide;
N-(6-benzo[1,3]dioxol-5-yl-4,5,6,7-tetrahydro-benzothiazole-2-yl)-guanidine or its formate;
N-[6-(4-cyanophenyl)-4,5,6,7-tetrahydro-benzothiazole-2-yl]-guanidine or its formate;
N-(4-benzyl-4,5,6,7-tetrahydro-benzothiazole-2-yl)-guanidine or its formate;
N-(5-methyl-5-phenyl-4,5,6,7-tetrahydro-benzothiazole-2-yl)-guanidine or its formate;
N-[6-(3,5-bis-trifluoromethylphenyl)-4,5,6,7-tetrahydro-benzothiazole-2-yl]-guanidine or its formate;
N-(6-o-tolyl-4,5,6,7-tetrahydro-benzothiazole-2-yl)-guanidine or its formate;
N-(6-m-tolyl-4,5,6,7-tetrahydro-benzothiazole-2-yl)-guanidine or its formate;
N-[6-(2-ethyl-phenyl)-4,5,6,7-tetrahydro-benzothiazole-2-yl]-guanidine or its formate;
N-[6-(4-chlorophenyl)-4,5,6,7-tetrahydro-benzothiazole-2-yl]-guanidine or its formate;
N-[6-(4-benzyloxy-phenyl)-4,5,6,7-tetrahydro-benzothiazole-2-yl]-guanidine or its hydrobromide;
N-(6-phenyl-4,5,6,7-tetrahydro-benzothiazole-2-yl-4-spiro-cyclohexane)-guanidine or its hydrobromide; or
N-(6-p-tolyl-4,5,6,7-tetrahydro-benzothiazole-2-yl)-guanidine or its formate.

6. The compound according to claim 1, wherein the compound is N-[4-(2-cyano-ethyl)-4,5,6,7-tetrahydro-benzothiazole-2-yl]-guanidine or its formate.

7. A pharmaceutical composition, comprising the compound of claim 1.

8. A medicinal product, comprising the compound of claim 1 and an inert carrier.

9. A compound of formula I

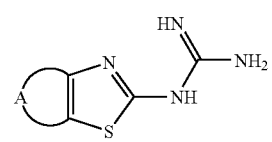

I wherein A is a three to six carbon atom chain which may be interrupted by oxygen and together with the thiazole ring can form a 5,6-dihydro-4H-cyclopentathiazole, 4,5,6,7-tetrahydrobenzothiazole, 5,6,7,8-tetrahydro-4H-cycloheptathiazole, or 6,7-dihydro-4H-pyrano[4,3-d]thiazole skeleton, wherein at least one of the carbon atoms of A is substituted by one or more:

methyl, ethyl, n-propyl, isopropyl, n-butyl, isobutyl, sec-butyl, tert-butyl, 1,1-dimethylpropyl, allyl or cyclohex-1-enyl groups; or phenyl, O-tolyl, m-tolyl, p-tolyl, 2-ethylphenyl, 3-fluorophenyl, 4-fluorophenyl, 4-chlorophenyl, 4-cyanophenyl, 4-benzyloxyphenyl, 3-methoxyphenyl, 4-methoxyphenyl, 3,4-dimethoxyphenyl, 3,4-methylenedioxyphenyl or bis-3,5-trifluoromethylphenyl groups; or thiophene-2-yl or benzyl groups; or cyano or cyanoethyl groups; or pentamethylene groups linked at each end to a single carbon atom;

or a pharmaceutically acceptable salt thereof.

10. A pharmaceutical composition, comprising the compound of claim 9.

11. A medicinal product, comprising the compound of claim 9 and an inert carrier.

12. A compound of formula I

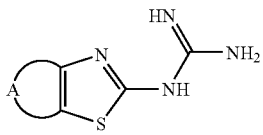

wherein A is a three to six carbon atom chain, wherein
(i) A does not comprise double bonds; and
(ii) at least one of the carbon atoms of A is substituted by one or more methyl groups;

or a pharmaceutically acceptable salt thereof.

13. The compound according to claim 12, wherein the compound is
N-(5,5-dimethyl-4,5,6,7-tetrahydro-benzothiazole-2-yl)-guanidine or its formate;
N-(6,6-dimethyl-4,5,6,7-tetrahydro-benzothiazole-2-yl)-guanidine;
N-(5-methyl-4,5,6,7-tetrahydro-benzothiazole-2-yl)-guanidine; or
N-(4-methyl-4-propyl-4,5,6,7-tetrahydro-benzothiazole-2-yl)-guanidine.

14. The compound according to claim 12, wherein the compound is
N-(7-methyl-4,5,6,7-tetrahydro-benzothiazole-2-yl)-guanidine or its formate;
N-(4,4-dimethyl-4,5,6,7-tetrahydro-benzothiazole-2-yl)-guanidine;
N-(4-methyl-4,5,6,7-tetrahydro-benzothiazole-2-yl)-guanidine or its formate; or
N-(6-methyl-4,5,6,7-tetrahydro-benzothiazole-2-yl)-guanidine.

15. A pharmaceutical composition, comprising the compound of claim 12.

16. A medicinal product, comprising the compound of claim 12 and an inert carrier.

17. The compound according to claim 1, wherein at least one of the carbon atoms of A is substituted by one or more:
ethyl, n-propyl, isopropyl, n-butyl, isobutyl, sec-butyl, tert-butyl, 1,1-dimethylpropyl, allyl or cyclohex-1-enyl groups; or phenyl, o-tolyl, m-tolyl, p-tolyl, 2-ethylphenyl, 3-fluorophenyl, 4-fluorophenyl, 4-chlorophenyl, 4-cyanophenyl, 4-benzyloxyphenyl, 3-methoxyphenyl, 4-methoxyphenyl, 3,4-dimethoxyphenyl, 3,4-methylenedioxyphenyl or bis-3,5-trifluoromethylphenyl groups; or thiophene-2-yl or benzyl groups; or cyano or cyanoethyl groups; or pentamethylene groups linked at each end to a single carbon atom.

18. The compound according to claim 1, wherein one carbon atom of A is substituted by two phenyl groups.

* * * * *